(12) United States Patent
Meimetis et al.

(10) Patent No.: US 10,517,965 B2
(45) Date of Patent: Dec. 31, 2019

(54) BIOORTHOGONAL TURN-ON PROBES

(71) Applicant: The General Hospital Corporation, Boston, MA (US)

(72) Inventors: Labros Meimetis, Somerville, MA (US); Jonathan Carlson, Jamaica Plain, MA (US); Ralph Weissleder, Peabody, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/889,647

(22) PCT Filed: May 6, 2014

(86) PCT No.: PCT/US2014/036977
§ 371 (c)(1),
(2) Date: Nov. 6, 2015

(87) PCT Pub. No.: WO2014/182704
PCT Pub. Date: Nov. 13, 2014

(65) Prior Publication Data
US 2016/0121002 A1    May 5, 2016

Related U.S. Application Data

(60) Provisional application No. 61/819,913, filed on May 6, 2013.

(51) Int. Cl.
| | |
|---|---|
| *A61B 5/00* | (2006.01) |
| *A61B 8/00* | (2006.01) |
| *A61B 10/00* | (2006.01) |
| *A61K 49/00* | (2006.01) |
| *C07F 5/02* | (2006.01) |
| *C07D 405/10* | (2006.01) |
| *C07D 455/03* | (2006.01) |
| *C07D 491/052* | (2006.01) |

(52) U.S. Cl.
CPC ...... *A61K 49/0052* (2013.01); *A61K 49/0021* (2013.01); *A61K 49/0039* (2013.01); *A61K 49/0056* (2013.01); *A61K 49/0058* (2013.01); *C07D 405/10* (2013.01); *C07D 455/03* (2013.01); *C07D 491/052* (2013.01); *C07F 5/022* (2013.01)

(58) Field of Classification Search
CPC ............ A61K 49/0039; A61K 49/0021; A61K 49/0052
USPC .......................................................... 424/9.6
See application file for complete search history.

(56) References Cited

U.S. PATENT DOCUMENTS

| | | | | |
|---|---|---|---|---|
| 5,830,912 A | * | 11/1998 | Gee | ...... C07D 311/16 514/457 |
| 5,955,604 A | * | 9/1999 | Tsien | ...... C07D 501/00 435/18 |
| 2005/0249668 A1 | | 11/2005 | Weissleder et al. | |
| 2006/0269942 A1 | | 11/2006 | Kolb et al. | |
| 2008/0181847 A1 | | 7/2008 | Robillard et al. | |
| 2011/0097735 A1 | * | 4/2011 | Mao | ...... C07C 309/47 435/7.2 |

FOREIGN PATENT DOCUMENTS

| | | |
|---|---|---|
| WO | WO 2006/026368 | 3/2006 |
| WO | WO 2007/144200 | 12/2007 |
| WO | WO 2012-012612 | 1/2012 |

OTHER PUBLICATIONS

Jose et al. Tetrahedron Lett. 50 (2009) 6442-6445.*
Devaraj et al. Angew. Chem. Int. Ed. 20-10, 49, 2869-2872.*
Kim et al. J. Phys. Chem. A 2006, 110, 20-27.*
International Search Report and Written Opinion dated Nov. 24, 2014 in international application No. PCT/US2014/036977, 14 pgs.
PubChem. Compound Summary for AGN-PC-049EZT. Create Date: Feb. 20, 2008. [retrieved on Oct. 28, 2014]. Retrieved from the Internet. <URL: https://pubchem.ncbi.nlm.nih.gov/compound/23816053?from=summary>.
Devaraj et al. Fast and Sensitive Pretargeted Labeling of Cancer Cells via Tetrazine/Trans-Cyclooctene Cycloaddition. Angew Chem Int Ed Engl. 48(38): 7013-7016,2009.
Agasti et al., "Dual imaging and photoactivatable nanoprobe for controlled cell tracking," Small, Jan. 2013, 9:222-227.
Atkins and Bliss, "Substituted coumarins and azacoumarins. Synthesis and fluorescent properties," J. Org. Chem., 1978, 43:1975-1980.
Balcar et al., "Reaktivität von stickstoff-heterocyclen genenüber cyclooctin als dienophile," Tet Lett., 1983, 24:1481-1484 (with English abstract).
Baskin and Bertozzi, "Bioorthogonal Click Chemistry: Covalent Labeling in Living Systems," QSAR Comb. Sci., Dec. 2007, 26:1211-1219.
Baskin et al., "Copper-free click chemistry for dynamic in vivo imaging," PNAS, Oct. 2007, 104:16793-7.
Bates et al., "Multicolor Super-resolution Imaging with Photo-switchable Fluorescent Probes," Science, Sep. 2007, 317:1749-1753.
Blackman et al., "Tetrazine ligation: fast bioconjugation based on inverse-electron-demand Diels-Alder reactivity," J. Am. Chem. Soc., Oct. 2008, 130:13518-9.

(Continued)

*Primary Examiner* — Michael G. Hartley
*Assistant Examiner* — Sean R Donohue
(74) *Attorney, Agent, or Firm* — Fish & Richardson P.C.

(57) ABSTRACT

This present application relates to fluorescent tetrazine-containing compounds consisting of a single pi-system. For example, a compound of Formula (I): or a salt thereof, wherein: F is a fluorophore, L is a conjugated linker, and Tz is a substituted or unsubstituted tetrazine; wherein the linker bridges the Tz and F moieties in a single conjugated pi-system. Also provided herein are methods of using the compounds provided herein for biomedical imaging.

3 Claims, 13 Drawing Sheets

(56) References Cited

OTHER PUBLICATIONS

Blom et al., "Preparative LC-MS Purification: Improved Compound-Specific Method Optimization," J. Combi. Chem., 2004, 6(6):874-883.

Boyce and Bertozzi, "Bringing chemistry to life," Nat. Methods, Jul. 2011, 8:638-642.

Budin et al., "Bioorthogonal Probes for Polo-Like Kinase 1 Imaging and Quantification," Angew. Chem., Sep. 2011, 123:9550-9553.

Bura and Ziessel, "Water-soluble phosphonate-substituted BODIPY derivatives with tunable emission channels," Org. Letters, Jun. 2011, 13(12):3072-3075.

Cramer and Mitchison, "Moving and stationary actin filaments are involved in spreading of postmitotic PtK2 cells," J. Cell Biol., Aug. 1993, 122(4):833-43.

Crosby and Demas, "Measurement of photoluminescence quantum yields. Review," The Journal of Physical Chemistry, Apr. 1971, 75(8):991-1024.

Devaraj et al., "Fast and Sensitive Pretargeted Labeling of Cancer Cells through a Tetrazine/trans-Cyclooctene Cycloaddition," Angew. Chem., 2009, 121:7147-7150.

Devaraj et al., "Tetrazine-Based Cycloadditions: Application to Pretargeted Live Cell Imaging," Bioconjug. Chem., Dec. 2008, 19:2297-9.

Droumaguet et al., "Fluorogenic click reaction," Chem. Soc. Rev., 2010, 39:1233-1239.

Eaton, "Reference materials for fluorescence measurement," Pure and Applied Chemistry, Jan. 1988, 60(7):1107-1114.

Graziano, "Rate enhancement of Diels-Alder reactions in aqueous Solutions," J. Phys. Org. Chem., 2004, 17:100-101.

Hangauer and Bertozzi, "A FRET-based Fluorogenic Phosphine for Live Cell Imaging with the Staudinger Ligation," Angew. Chem. Int. Ed. Engl., 2008, 47:2394-7 (Author Manuscript).

Hangauer and Bertozzi, "A FRET-Based Fluorogenic Phosphine for Live-Cell Imaging with the Staudinger Ligation," Angew. Chem., Mar. 2008, 47: 2394-2397.

Haun et al., "Bioorthogonal chemistry amplifies nanoparticle binding and enhances the sensitivity of cell detection," Nat. Nanotech., Sep. 2010, 5:660-665.

International Preliminary Report on Patentability in International Application No. PCT/US2014/036977, dated Nov. 19, 2015, 8 pages.

Jiang et al., "Development of mono- and di-AcO substituted BODIPYs on the boron center," Org. Letters, Jan. 2012, 14(1):248-251.

Kwart and King, "The reverse Diels-Alder or retrodiene reaction," Chem. Rev., 1968, 68:415-447.

Lang et al., "Genetically encoded norbornene directs site-specific cellular protein labelling via a rapid bioorthogonal reaction," Nat. Chem., Feb. 2012, 4:298-304.

Laughlin et al., "In Vivo Imaging of Membrane-Associated Glycans in Developing Zebrafish," Science, May 2008, 320:664-7.

Lemieux et al., "A Fluorogenic Dye Activated by the Staudinger Ligation," J. Am. Chem. Soc., Apr. 2003, 125:4708-9.

Li et al., "Syntheses and Spectral Properties of Functionalized, Water-Soluble BODIPY Derivatives," J. Org. Chem., 2008, 73:1963-1970.

Liu et al., "Diels-Alder Cycloaddition for Fluorophore Targeting to Specific Proteins inside Living Cells," J. Am. Chem. Soc., 2012, 134:792-795.

Loudet and Burgess, "BODIPY Dyes and Their Derivatives: Syntheses and Spectroscopic Properties," Chem. Rev., 2007, 107:4891-4932.

Magde et al., "Fluorescence Quantum Yields and Their Relation to Lifetimes of Rhodamine 6G and Fluorescein in Nine Solvents: Improved Absolute Standards for Quantum Yields," Photochemistry and Photobiology, Apr. 2002, 75(4):327-334.

Neef and Schultz, "Selective Fluorescence Labeling of Lipids in Living Cells," Angew. Chem. Int. Ed. Engl., 2009, 48:1498-500.

Neuteboom et al., "Solvent Mediated Intramolecular Photoinduced Electron Transfer in a Fluorene-Perylene Bisimide Derivative," Phys. Chem. A., Nov. 2006, 110:12363-12371.

Ning et al., "Visualizing Metabolically Labeled Glycoconjugates of Living Cells by Copper-Free and Fast Huisgen Cycloadditions," Angewandte Chemie—International Edition, 2008, 47:2253-2255.

Niu et al., "Water-soluble BODIPY derivatives," Org. Letters, May 2009, 11(10):2049-2052.

Patterson et al., "Superresolution Imaging using Single-Molecule Localization," Annu. Rev. Phys. Chem., 2010, 61:345.

Peturssion et al., "Protecting Groups in Carbohydrate Chemistry," J. Chem. Educ., 1997, 74(11):1297.

Pipkorn et al., "Inverse-electron-demand Diels-Alder reaction as a highly efficient chemoselective ligation procedure: Synthesis and function of a BioShuttle for temozolomide transport into prostate cancer cell," J. Pept. Sci., Mar. 2009, 15:235-41.

Prescher and Bertozzi, "Chemistry in living systems," Nat. Chem. Biol., 2005, 1:13-21.

Reiner et al., "Bioorthogonal Small-Molecule Ligands for PARP1 Imaging in Living Cells," Chembiochem, Nov. 2010, 11:2374-2377.

Rideout et al., "Hydrophobic acceleration of Diels-Alder reactions," J. Am. Chem. Soc., 1980, 102:7816-7817.

Sauer et al., "Umsetzungen von 1.2.4.5-Tetrazinen mit Olefinen. Zur Struktur von Dihydropyridazinen," Chem. Ber., 1965, 998:1435-1445 (with English translation).

Schiedel et al., "Single-Compound Libraries of Organic Materials: Parallel Synthesis and Screening of Fluorescent Dyes," Angew. Chem. Int. Ed., Dec. 2001, 40:4677-4680.

Shieh et al., "Fluorogenic Azidofluoresceins for Biological Imaging," J. Am. Chem. Soc., 2012, 134:17428.

Sivakumar et al., "A Fluorogenic 1,3-Dipolar Cycloaddition Reaction of 3-Azidocoumarins and Acetylenes," Org Lett, 2004, 6:4603-6.

Tahtaoui et al., "Convenient method to access new 4,4-dialkoxy and 4,4-diaryloxy-diaza-s-indacene dyes: Synthesis and spectroscopic evaluation," J. Org. Chem., 2007, 72:269-272.

Thalhammer et al., "The reactivity of simple open chain and cyclic dienophiles in Diels-Alder-reactions with inverse electronic supply," Tet. Lett., Jan. 1990, 31(47):6851-6854 9 (with English summary).

Thompson et al., "Chapter Two—Molecules and Methods for Super-Resolution Imaging," Methods Enzymol., 2010 475:27-59.

Ulrich et al., "The chemistry of fluorescent bodipy dyes: versatility unsurpassed," Angew. Chem. Int. Ed., 2008, 47:1184-1201.

Xie and Schultz, "A chemical toolkit for proteins—an expanded genetic code," Nat. Rev. Mol. Cell Biol., Oct. 2006, 7:775-782.

Yang et al, "Live-Cell Imaging of Cyclopropene Tags with Fluorogenic Tetrazine Cycloadditions," Angew. Chem., Jul. 2012, 124:7594-7597.

Yang et al., "Bioorthogonal Imaging of Aurora Kinase A in Live Cells," Angew. Chem., 2012, 124:6702-6707.

Yao et al., "Fluorophore Targeting to Cellular Proteins via Enzyme-Mediated Azide Ligation and Strain-Promoted Cycloaddition," J. Am. Chem. Soc., 2012, 134:3720-3728.

Zhou and Fahrni, "A Fluorogenic Probe for the Copper(I)-Catalyzed Azide-Alkyne Ligation Reaction: Modulation of the Fluorescence Emission via 3(n,π*)-1(π,π*) Inversion," J. Am. Chem. Soc., 2004, 126:8862-3.

Zhu et al., "Highly Water-soluble Neutral BODIPY Dyes with Controllable Fluorescence Quantum Yields," Org. Letters, Feb. 2011, 13(3):438-441.

Ziessel et al., "The chemistry of BODIPY: A new El Dorado for fluorescence tools," New J. Chem., 2007, 31:496-501.

\* cited by examiner

A

B

BIOORTHOGONAL TURN-ON PROBES

CROSS-REFERENCE TO RELATED APPLICATIONS

This application is a U.S. National Phase Application under 35 U.S.C. § 371 of International Patent Application No. PCT/US2014/036977, filed on May 6, 2014, which claims priority to U.S. Application Ser. No. 61/819,913, filed on May 6, 2013, both of which are incorporated by reference in their entirety.

TECHNICAL FIELD

This present application relates to fluorescent tetrazine-containing compounds consisting of a single pi-system. Also provided herein are methods of using the compounds provided herein for biomedical imaging.

BACKGROUND

Visualizing biomolecular processes has been enhanced by combining fluorophores with bioorthogonal chemistry, resulting in new tools to study the complex biochemical milieu of living cells and organisms. (N. K. Devaraj, et al., *Angew. Chem.* 2009, 121, 7147-7150; M. Boyce and C. R. Bertozzi, *Nat. Methods* 2011, 8, 638; and C. L. Droumaguet and C. Wang, Q. Wang, *Chem. Soc. Rev.* 2010, 39, 1233.) The resulting probes have been applied to image glycosylation and phospholipid uptake, cellular proteins, and intracellular drug distribution. (P. Shieh, et al., *J. Am. Chem. Soc.* 2012, 134, 17428; S. T. Laughlin, et al., *Science* 2008, 320, 664; M. J. Hangauer and C. R. Bertozzi, *Angew. Chem.* 2008, 120, 2353; J. Yang, et al, *Angew. Chem.* 2012, 124, 7594-7597; K. Lang, et al., *Nat. Chem.* 2012, 4, 298; D. S. Liu, et al., *J. Am. Chem. Soc.* 2012, 134, 792; N. K. Devaraj, et al., *Bioconjug. Chem.* 2008, 19, 2297; J. Z. Yao, et al., *J. Am. Chem. Soc.* 2012, 134, 3720; K. S. Yang, et al., *Angew. Chem.* 2012, 124, 6702-6707; G. Budin, et al., *Angew. Chem.* 2011, 123, 9550-9553; T. Reiner, et al, *Chembiochem* 2010, 11, 2374.)

Bioorthogonal "click" chemistries are widely used in chemical biology for a myriad of applications such as activity based protein profiling, crosslinking of proteins, monitoring cell proliferation, generation of novel enzyme inhibitors, monitoring the synthesis of newly formed proteins, protein target identification, and studying glycan processing. Perhaps the most fascinating applications involve using these bioorthogonal chemistries to assemble molecules in the presence of living systems such as live cells or even whole organisms (Baskin et al., 2007, Proc Natl Acad Sci USA, 104, 16793-7; Laughlin et al., 2008, Science, 320, 664-7; Prescher and Bertozzi, 2005, Nat Chem Biol, 1, 13-21; Neef and Schultz, 2009, Angew Chem Int Ed Engl, 48, 1498-500; Ning et al., 2008, Angewandte Chemie-International Edition, 47, 2253-2255). These latter applications require that the chemistry be non-toxic and possess kinetics that allow fast reaction to occur with micromolar concentrations of reagents in a time span of minutes to hours.

To fulfill these criteria, various "copper-free" click chemistries have been reported, such as the strain-promoted azide-alkyne cycloaddition and the Staudinger ligation, to react with azides on the surface of live cells both in culture and in in vivo systems such as mice and zebrafish (Prescher and Bertozzi, 2005, Nat Chem Biol, 1, 13-21). However, to date, the application of "click" chemistry in living systems, has been largely limited to extracellular targets and no technique has shown reliable ability to specifically label and image intracellular targets (Baskin and Bertozzi, 2007, QSAR Comb. Sci., 26, 1211-1219). The reasons for this are likely several. In addition to fulfilling the stability, toxicity, and chemoselectivity requirements of "click" chemistry, intracellular live cell labeling requires reagents that can easily pass through biological membranes and kinetics that enable rapid labeling even with the low concentrations of agent that make it across the cell membrane. Additionally, a practical intracellular bioorthogonal coupling scheme would need to incorporate a mechanism by which the fluorescent tag increases in fluorescence upon covalent reaction to avoid visualizing accumulated but unreacted imaging probes (i.e. background). This "turn-on" would significantly increase the signal-to-background ratio, which is particularly relevant to imaging targets inside living cells since a stringent washout of unreacted probe is not possible.

In previous years a number of elegant probes have been introduced whose fluorescence increases after azide-alkyne cycloaddition or staudinger ligation coupling reactions (Sivakumar et al., 2004, Org Lett, 6, 4603-6; Zhou and Fahmi, 2004, J Am Chem Soc, 126, 8862-3; Hangauer and Bertozzi, 2008, Angew Chem Int Ed Engl, 47, 2394-7; Lemieux et al., 2003, J Am Chem Soc, 125, 4708-9). Most of these strategies either require a reactive moiety intimately attached to the fluorophore thus requiring synthesis of new fluorophore scaffolds or take advantage of a FRET based activation requiring appendage of an additional molecule that can act as an energy transfer agent. Furthermore, most probes utilizing these popular coupling schemes have to date been unable to label intracellular targets in live cells.

The bioorthogonal Diels-Alder reaction is compatible with aqueous environments and has second order rate constants that are known to be enhanced up to several hundred-fold in aqueous media in comparison to organic solvents. (Rideout D C et al., 1980, *J Am Chem Soc* 102:7816-7817; Graziano G, 2004, *J Phys Org Chem* 17:100-101). Many Diels-Alder reactions are reversible, therefore, they may not be suitable for biological labeling. (Kwart et al., 1968, *Chem Rev* 68:415-447), however, the inverse electron demand Diels-Alder cycloaddition of olefins with tetrazines results in irreversible coupling giving dihydropyridazine products. During this reaction, dinitrogen is released in a retro Diels-Alder step. (Sauer J et al., 1965, *Chem Ber* 998:1435-1445). A variety of tetrazines and dienophiles including cyclic and linear alkenes or alkynes have been studied in this reaction. Selection of the appropriate reaction partners, allows for tuning of the coupling rate by several orders of magnitude. (Balcar J et al., 1983, *Tel Lett* 24:1481-1484; Thalhammer F et al., 1990, *Tel Lett* 47:6851-6854). See also US 2006/0269942, WO 2007/144200, and US 2008/0181847.

SUMMARY

In some previously described fluorophores, the capacity of in situ chemical conjugation has been paired with fluorogenic turn-on, whereby fluorophore emission increases upon reaction with its bioorthogonal counterpart ("turn-on" probes). See, e.g., N. K. Devaraj, et al., *Angew. Chem.* 2009, 121, 7147-7150. This has the very attractive feature of reducing background fluorescence when doing in vivo imaging, potentially allowing real time imaging, without washing or clearance steps. Existing methods that exploit azide-phosphine, azide-alkyne, or inverse electron demand Diels- Alder tetrazine cycloadditions have not provided probes with high fluorescence turn-on ratios and fast kinetics without using a catalyst.

Provided herein are compounds of Formula (I) or (II):

F-L-Tz        (I)

F-Tz          (II)

or a salt thereof,
wherein:
F is a fluorophore;
L is a conjugated linker; and
Tz is a substituted or unsubstituted tetrazine;
wherein the linker bridges the Tz and F moieties in a single conjugated pi-system.

Compound of Formula (I) or (II) can be reacted with a dienophile to prepare compounds of Formula (III) or (IV):

F-L-Z         (III)

F-Z           (IV)

or a salt thereof,
wherein:
F is a fluorophore;
L is a conjugated linker; and
Z is a moiety comprising the reaction product of a diene and a dienophile, wherein the diene is a tetrazine or a derivative thereof;
wherein the linker bridges the Z and F moieties in a single conjugated pi-system.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 7A shows fluorogenic imaging of EGFR expression on both fixed and live A431 cells. FIG. 7B are fluorogenic live-cell images of intracellular nanoparticles internalized by RAW 264.7 cells.

FIG. 12A shows mitochondrial imaging of OVCA-429 cells with RFP-tagged mitochondria were incubated with an anti-mitochondria-TCO antibody, rinsed briefly, and then imaged after addition of 100 nm HELIOS-388H in PBS. FIG. 12B shows actin imaging of COS-1 cells incubated with phalloidin-TCO (1 µg/mL) and DRAQ5 nuclear counterstain (1 µM, BioStatus), rinsed briefly, and then imaged upon addition of the indicated HELIOS probe at 100 nM. Control images were collected at matched dye concentrations in the absence of phalloidin-TCO.

DETAILED DESCRIPTION

Definitions

Figure 1:
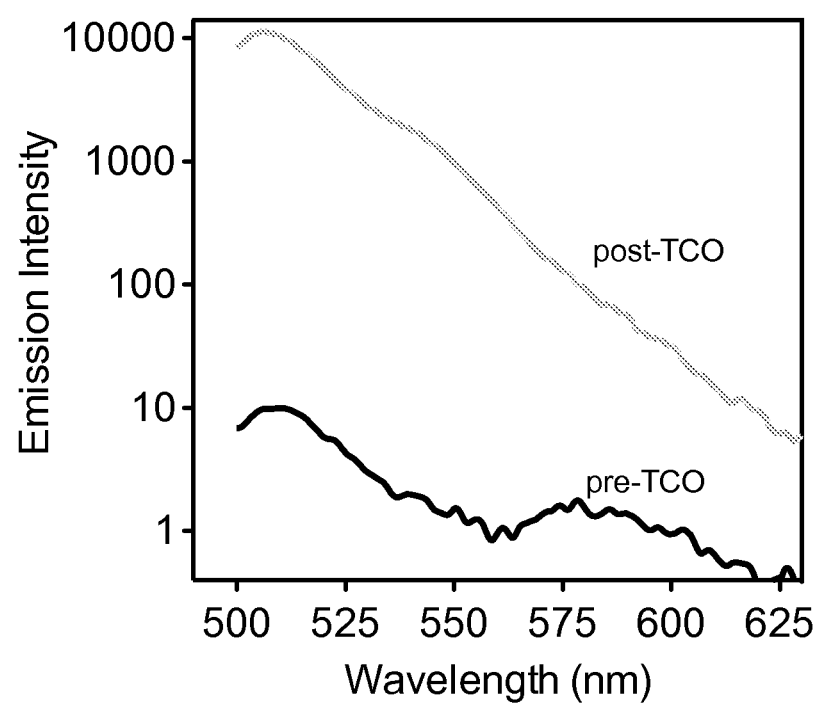
FIG. 1 is a fluorescence emission spectra for compound 4b in acetonitrile at baseline (black) and after addition of TCO (green); excitation at 490 nm.

For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about", whether or not the term is explicitly used, unless explicitly stated otherwise. As used herein, the singular forms "a," "an," and "the" include plural referents unless the context clearly dictates otherwise.

The term "alkyl" includes straight-chain alkyl groups (e.g., methyl, ethyl, propyl, butyl, pentyl, hexyl, heptyl, octyl, nonyl, decyl, etc.) and branched-chain alkyl groups (e.g., isopropyl, tert-butyl, isobutyl, etc.). In certain embodiments, a straight chain or branched chain alkyl has twelve or fewer carbon atoms in its backbone (e.g., $C_1$-$C_{12}$ for straight chain; $C_3$-$C_{12}$ for branched chain). The term $C_1$-$C_{12}$ includes alkyl groups containing 1 to 12 carbon atoms.

The term "alkenyl" includes aliphatic groups that may or may not be substituted, as described above for alkyls, containing at least one double bond and at least two carbon atoms. For example, the term "alkenyl" includes straight-chain alkenyl groups (e.g., ethenyl, propenyl, butenyl, pentenyl, hexenyl, heptenyl, octenyl, nonenyl, and decenyl) and branched-chain alkenyl groups. In certain embodiments, a straight chain or branched chain alkenyl group has twelve or fewer carbon atoms in its backbone (e.g., $C_2$-$C_{12}$ for straight chain; $C_3$-$C_{12}$ for branched chain). The term $C_2$-$C_{12}$ includes alkenyl groups containing 2 to 12 carbon atoms.

The term "alkynyl" includes unsaturated aliphatic groups analogous in length and possible substitution to the alkyls described above, but which contain at least one triple bond and two carbon atoms. For example, the term "alkynyl"

includes straight-chain alkynyl groups (e.g., ethynyl, propynyl, butynyl, pentynyl, hexynyl, heptynyl, octynyl, nonynyl, and decynyl) and branched-chain alkynyl groups. In certain embodiments, a straight chain or branched chain alkynyl group has twelve or fewer carbon atoms in its backbone (e.g., $C_2$-$C_{12}$ for straight chain; $C_3$-$C_{12}$ for branched chain). The term $C_2$-$C_{12}$ includes alkynyl groups containing 2 to 12 carbon atoms.

The term "alkoxy" is used in its conventional sense, and refers to alkyl groups linked to molecules via an oxygen atom. In some embodiments, an alkoxy has twelve or fewer carbon atoms in its backbone (e.g., a $C_1$-$C_{12}$ alkoxy). For example, $C_1$-$C_{10}$, $C_1$-$C_8$, $C_1$-$C_6$, $C_1$-$C_4$, $C_1$-$C_3$, or $C_1$-$C_2$. Non-limiting examples of an alkoxy group include methoxy, ethoxy, propoxy, butoxy, and hexoxy.

The terms "halo" or "halogen", used alone or in combination with other terms, refers to fluoro, chloro, bromo and iodo.

The term "haloalkyl" refers to an alkyl group in which one or more of the hydrogen atoms has been replaced by a halogen atom. The term "$C_n$-$C_m$ haloalkyl" refers to a $C_n$-$C_m$ alkyl group having n to m carbon atoms, and from at least one up to {2(n to m)+} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_n$-$C_m$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "amino" refers to a group of formula —$NH_2$.

The term "carbamyl" refers to a group of formula —C(O)$NH_2$.

The term "carbonyl", employed alone or in combination with other terms, refers to a —C(=O)— group, which also may be written as C(O).

The term "oxo" refers to oxygen as a divalent substituent, forming a carbonyl group, or attached to a heteroatom forming a sulfoxide or sulfone group, or an N-oxide group.

The term "aromatic" refers to a carbocycle or heterocycle having one or more polyunsaturated rings having aromatic character (i.e., having (4n+2) delocalized π (pi) electrons where n is an integer).

The term "carbocyclyl" includes a cyclic aliphatic group which may be saturated or unsaturated. For example, carbocyclyl groups include cyclopropyl, cyclopentyl, cyclohexyl, cycloheptyl, and cyclooctyl. In some embodiments, carbocyclyls have from 3-8 carbon atoms in their ring structure, for example, they can have 3, 4, 5 or 6 carbons in the ring structure.

In general, the term "aryl" includes groups, including 5- and 6-membered single-ring aromatic groups, such as benzene and phenyl. Furthermore, the term "aryl" includes multicyclic aryl groups, e.g., tricyclic, bicyclic, such as naphthalene and anthracene.

The term "heteroaryl" includes groups, including 5- and 6-membered single-ring aromatic groups, that have from one to four heteroatoms, for example, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "heteroaryl" includes multicyclic heteroaryl groups, e.g., tricyclic, bicyclic, such as benzoxazole, benzodioxazole, benzothiazole, benzoimidazole, benzothiophene, methylenedioxyphenyl, quinoline, isoquinoline, napthyridine, indole, benzofuran, purine, benzofuran, quinazoline, deazapurine, indazole, or indolizine.

The term "heterocyclyl" includes non-aromatic groups, including but not limited to, 3- to 10-membered single or multiple non-aromatic rings having one to five heteroatoms, for example, oxetane, piperazine, pyrrolidine, piperidine, or homopiperazine.

The term "substituted" means that an atom or group of atoms replaces hydrogen as a "substituent" attached to another group. For aryl and heteroaryl groups, the term "substituted", unless otherwise indicated, refers to any level of substitution, namely mono, di, tri, tetra, or penta substitution, where such substitution is permitted. The substituents are independently selected, and substitution may be at any chemically accessible position. In some cases, two sites of substitution may come together to form a 3-10 membered carbocyclyl or heterocyclyl ring.

Substituents include, but are not limited to, $Cy^1$, $C_{1-6}$ alkyl, $C_{2-6}$ alkenyl, $C_{2-6}$ alkynyl, halo, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR_{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$;

each $Cy^1$ is independently $C_{6-10}$ aryl, $C_{3-10}$ carbocyclyl, 5-10 membered heteroaryl or 4-10 membered heterocyclyl, each of which is unsubstituted or substituted by 1, 2, 3, 4 or 5 substituents independently selected from $C_{1-6}$ alkyl, $C_{2-6}$ alkenyl, $C_{2-6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and oxo;

each $R^{a1}$, $R^{b1}$, $R^{c1}$, $R^{d1}$, is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl or (4-10 membered heterocyclyl)-$C_{1-4}$ alkyl, wherein said $C_{1-6}$ alkyl, $C_{2-6}$ alkenyl, $C_{2-6}$ alkynyl, $C_{6-10}$ aryl, $C_{3-10}$ carbocyclyl, 5-10 membered heteroaryl, 4-10 membered heterocyclyl, $C_{6-10}$ aryl-$C_{1-4}$ alkyl, $C_{3-10}$ carbocyclyl-$C_{1-4}$ alkyl, (5-10 membered heteroaryl)-$C_{1-4}$ alkyl and (4-10 membered heterocyclyl)-$C_{1-4}$ alkyl is optionally substituted with 1, 2, 3, 4, or 5 substituents independently selected from $C_{1-4}$ alkyl, $C_{1-4}$ haloalkyl, halo, CN, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$ and $S(O)_2NR^{c4}R^{d4}$;

each $R^{a4}$, $R^{b4}$, $R^{c4}$ and $R^{d4}$ is independently selected from H, $C_{1-4}$ alkyl, $C_{1-4}$ haloalkyl, $C_{2-4}$ alkenyl and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

Where substituent groups are specified by their conventional chemical formulas, written from left to right, they equally encompass the chemically identical substituents that would result from writing the structure from right to left, for example, —CH₂O— is equivalent to —OCH₂—. In some embodiments, one or more substituents can be a group reactive with a biologically active molecule or a detectable agent.

The abbreviation "PEG" as used herein refers to a polyethylene glycol polymer.

A "reactive moiety" as used herein refers to a reactive moiety for conjugation between the fluorophore and/or the dienophile and a biologically active compound (e.g., an antibody). Non-limiting examples of reactive moieties include hydroxyl, amine, thiol, carboxyl, aldehyde, glyoxal, dione, alkenyl, alkynyl, alkedienyl, azide, acrylamide, vinyl sulfone, hydrazide, aminoxy, maleimide, dithiopyridine, iodoacetamide,

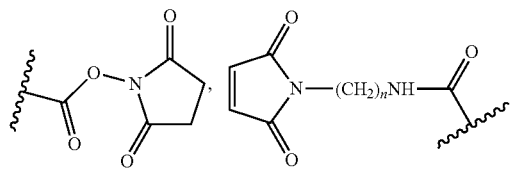

wherein n is an integer from 1 to 10, and

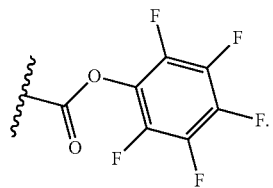 [SMILES: *C(=O)Oc1c(F)c(F)c(F)c(F)c1F]

As used herein, chemical structures which contain one or more stereocenters depicted with dashed and bold bonds (i.e., ⫶⎮) are meant to indicate absolute stereochemistry of the stereocenter(s) present in the chemical structure. As used herein, bonds symbolized by a simple line do not indicate a stereo-preference. Unless otherwise indicated, chemical structures, which include one or more stereocenters, illustrated herein without indicating absolute or relative stereochemistry encompass all possible stereoisomeric forms of the compound (e.g., diastereomers, enantiomers) and mixtures thereof (e.g., racemic mixtures). Structures with a single bold or dashed line, and at least one additional simple line, encompass a single enantiomeric series of all possible diastereomers.

Resolution of racemic mixtures of compounds can be carried out by any of numerous methods known in the art. An exemplary method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid, or the various optically active camphorsulfonic acids such as camphorsulfonic acid. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent compositions can be determined by one skilled in the art.

The term "counter anion" as used herein is intended to include any counter anions of inorganic and organic acids. Exemplary anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethanesulfonate, ethanesulfonate, benzenesulfonate, p-toluenesulfonate, p-trifluoromethylbenzenesulfonate, hydroxide, aluminates, and borates.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "salt" includes any ionic form of a compound and one or more counter-ionic species (cations and/or anions). Salts also include zwitterionic compounds (i.e., a molecule containing one more cationic and anionic species, e.g., zwitterionic amino acids). Counter ions present in a salt can include any cationic, anionic, or zwitterionic species. Exemplary anions include, but are not limited to: chloride, bromide, iodide, nitrate, sulfate, bisulfate, sulfite, bisulfite, phosphate, acid phosphate, perchlorate, chlorate, chlorite, hypochlorite, periodate, iodate, iodite, hypoiodite, carbonate, bicarbonate, isonicotinate, acetate, trichloroacetate, trifluoroacetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, trifluoromethanesulfonate, ethanesulfonate, benzenesulfonate, p-toluenesulfonate, p-trifluoromethylbenzenesulfonate, hydroxide, aluminates, and borates. Exemplary cations include, but are not limited to: monovalent alkali metal cations, such as lithium, sodium, potassium, and cesium, and divalent alkaline earth metals, such as beryllium, magnesium, calcium, strontium, and barium. Also included are transition metal cations, such as gold, silver, copper and zinc, as well as non-metal cations, such as ammonium salts.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; in some embodiments, a non-aqueous media like ether, ethyl acetate, alcohols (e.g., methanol, ethanol, isopropanol, or butanol) or acetonitrile (ACN) can be used. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salts are described, for example, in *Handbook of Pharmaceutical Salts: Properties, Selection, and Use,* Wiley-VCH, 2002.

The term "essentially pure" refers to chemical purity of a compound provided herein that may be substantially or essentially free of other components which normally accompany or interact with the compound prior to purification. By way of example only, a compound may be "essentially pure" when the preparation of the compound contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, an "essentially pure" compound may have a purity level of about 70%/0, about 75%, about 80%, about 85%, about 90%, about 95%, about 96%, about 97%, about 98%, about 99% or greater. For the purposes of this document, preparations of functionalized polymers or conjugates differing only in the length of their polymer chain are considered to be essentially pure. An essentially pure compound may be obtained using chromatographic purification methods.

As used herein, a "turn-on ratio" is a measure of the increase in fluorescence associated with probe activation and is the ratio of the fluorescence after and before activation of a compound provided herein. For example, a turn-on ratio for a compound of Formula (III) can be calculated by taking the ratio of the fluorescence intensity of a compound of Formula (III) over the fluorescence intensity of the corresponding compound of Formula (I). See, e.g., Thompson, M. A. et al., *Methods Enzymol* 2010 475: 27-59.

As used herein, "conjugated" refers to a compound having alternating single and multiple bonds and containing a system of connected p-orbitals with delocalized electrons.

Compounds

A fluorogenic probe enables the intrinsic fluorescence of a chromophore to be stably, but reversibly, suppressed. This can be accomplished by making customized modifications that directly perturb the intrinsic fluorophore, or, more generally, by linking a fluorophore to moieties that can quench its fluorescence via photoinduced electron transfer (PET) or via energy transfer, e.g. Förster resonance energy transfer (FRET). Subsequent disruption of the quenching group restores the light emission. An optimal probe of this type thus requires both highly efficient quenching and a facile, selective mechanism to modulate the quencher— either by cleavage of the linker or chemical reaction of the quencher itself.

Tetrazine-based probes achieve their fluorogenic turn-on by the latter route, as the tetrazine (Tz) chromophore can be characterized as both a quencher (via energy transfer) and a bioorthogonal reactant. First generation Tz-fluorophore probes relied on FRET, a through-space transfer mechanism that depends on distance, molecular alignment, as well as the intensity and alignment of emission-absorption bands, all of which can limit energy transfer efficiency. As a result, although they possess many desirable characteristics, including very fast, catalyst free, chemical reactivity and high brightness after turn-on, these probes were limited by fluorescence turn-on ratios of just 10-20 fold (i.e. 90-95% baseline quenching). Similar tradeoffs limit most PET-based probes in the literature, as many highly efficient quenchers have no intrinsic bioorthogonal reactivity, and reactive moieties, such as azide-modified fluorophores, have modest quenching ability and comparatively slow reaction kinetics.

In contrast, through-bond energy transfer (TBET) enables the Tz-based probes provided herein to display both exceptional turn-on and chemical reactivity. In the present system, TBET is markedly more efficient than FRET, achieving turn-on ratios of greater than $10^2$ and in some cases greater than $10^3$ (>99.9% baseline quenching). Several practical features can enhance TBET relative to FRET, including insensitivity to spectral overlap (allowing donor chromophores to excite significantly red-shifted acceptors), decreased dependence on donor acceptor dipole alignment, and accelerated energy transfer kinetics (due to the lack of a strict orientational requirement).

Many of the previously described tetrazine-based probes achieve their fluorogenic turn-on by a unique mechanism, in which the tetrazine (Tz) chromophore is both quencher and bioorthogonal reactant. In published studies, flexibly-linked Tz-fluorophore pairs—chosen for their ready synthetic accessibility—are quenched with moderate efficiency, yielding turn-on ratios on the order of 10-20 fold after reaction with dienophile targets. Although intriguing applications have been demonstrated, the limited turn-on ratios almost always result in native background during imaging applications. In some cases, a larger turn-on ratio is required for useful imaging. For example, a turn-on ratio of $10^2$ would be preferable for robust utility in cellular imaging applications, and a ratio of $10^3$ may be necessary for low abundance targets and super resolution imaging. Mechanistic observations have suggested that quenching in bichromophoric fluorophore-tetrazines occurs via Förster resonance energy transfer (FRET), offering a starting point for efforts to optimize turn-on. Although its relatively weak visible light absorbance inherently limits the range of tetrazine as a FRET acceptor, Förster theory dictates that energy transfer efficiency will be crucially dependent upon inter-chromophore distance (varying as $r^6$) and upon transition dipole alignment, which are both optimizable parameters. Without being bound by theory, an alternative way of designing more efficient turn-on probes, involves adapting through-bond energy transfer (TBET) for fluorescence quenching as is illustrated by the compounds provided herein.

Accordingly, provided herein are compounds of Formula (I):

F-L-Tz or a salt thereof,
wherein:
F is a fluorophore;
L is a conjugated linker; and
Tz is a substituted or unsubstituted tetrazine;
wherein the linker bridges the Tz and F moieties in a single conjugated pi-system.

Figure 8:
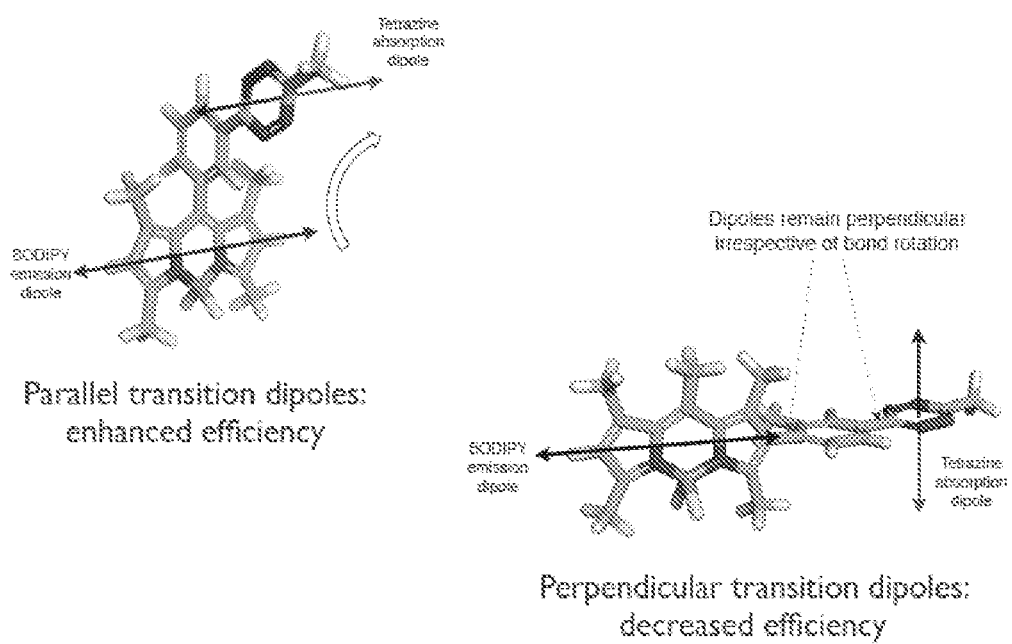
FIG. 8 illustrates a tetrazine transition dipole as collinear with or parallel to the transition dipole of the fluorophore.

The single, conjugated pi-system may, in some embodiments, be non-coplanar due to steric factors within the compound that enforce a twist in the interchromophore linkage between the F and L-Tz moieties. Such steric factors can originate from substituents on either the linker or on the fluorophore. Without being bound by theory, fluorescence can be increased when the L-Tz moiety is oriented with respect to the F moiety such that the tetrazine transition dipole is either collinear with or parallel to the transition dipole of the fluorophore (see, e.g., FIG. 8). In some embodiments, the pi-system is topologically conjugation (i.e., a single systems of alternating single and double bonds). In other embodiments, for example, when the pi-system is coplanar, the conjugation of the pi-system is both topologically and functionally (i.e., wherein the alternating single and double bonds are coplanar) conjugated.

In some embodiments, the compounds provided herein enhance spatial donor-acceptor proximity, provide predictable donor-acceptor transition dipole orientation, and/or afford the possibility of accessing alternate modes of fluorescence quenching.

A "fluorophore", as described herein, can be any small molecule that can re-emit light upon light excitation (e.g., light in the visible spectrum). For example, fluorophores can include rhodamines, fluoresceins, boron-dypyrromethanes, coumarins, pyrenes, cyanines, oxazines, acridines, auramine Os, and derivatives thereof. In some cases, derivatives include sulfonated derivatives such as sulfonated pyrenes, sulfonated coumarins, sulfonated rhodamines, and sulfonated cyanines (e.g., ALEXAFLUOR® dyes).

In particular, boron-dypyrromethanes fluorophores may include boron-dipyrromethene (BODIPY®); 4,4-difluoro-5,7-dimethyl-4-bora-3a,4a-diaza-s-indacene-3-propionic acid (BODIPY® FL); 6-((4,4-difluoro-1,3-dimethyl-5-(4-methoxyphenyl)-4-bora-3a,4a-diaza-s-indacene-2-propionyl)amino)hexanoic acid, succinimidyl ester (BODIPY® TRM-X); 6-(((4,4-difluoro-5-(2-pyrrolyl)-4-bora-3a,4a-diaza-s-indacene-3-yl)styryloxy)acetyl)aminohexanoic acid, succinimidyl ester (BODIPY® 650/665-X); 5,5-difluoro-1,3,7,9,10-pentamethyl-5H-dipyrrolo[1,2-c:2',1'-f][1,3,2]diazaborinin-4-ium-5-uide; 4,4-Difluoro-1,3,5,7-Tetramethyl-4-Bora-3a,4a-Diaza-s-Indacene-8-Propionic Acid; 4,4-Difluoro-5,7-Dimethyl-4-Bora-3a,4a-Diaza-s-Indacene-3-Propionic Acid; 4,4-Difluoro-5,7-Dimethyl-4-Bora-3a,4a-Diaza-s-Indacene-3-Pentanoic Acid; 6-((4,4-Difluoro-5,7-Dimethyl-4-Bora-3a,4a-Diaza-s-Indacene-3-Propionyl)amino)hexanoic Acid; 4,4-Difluoro-5-Phenyl-4-Bora-3a,4a-Diaza-s-Indacene-3-Propionic Acid; 4,4-Difluoro-5,7-Diphenyl-4-Bora-3a,4a-Diaza-s-Indacene-3-Propionic Acid; 6-((4,4-Difluoro-1,3-Dimethyl-5-(4-Methoxyphenyl)-4-Bora-3a,4a-Diaza-s-Indacene-2-Propionyl)amino) hexanoic Acid; 4,4-Difluoro-5-(2-Thienyl)-4-Bora-3a,4a-Diaza-s-Indacene-3-Propionic Acid; 4,4-Difluoro-5-Styryl-4-Bora-3a,4a-Diaza-s-Indacene-3-Propionic Acid; 4,4-Difluoro-5-(2-Pyrrolyl)-4-Bora-3a,4a-Diaza-s-Indacene-3-Propionic Acid; 4,4-Difluoro-5-(4-Phenyl-1,3-Butadienyl)-4-Bora-3a,4a-Diaza-s-Indacene-3-Propionic Acid; 6-(((4-(4,4-Difluoro-5-(2-Thienyl)-4-Bora-3a,4a-Diaza-s-Indacene-3-yl)phenoxy)acetyl)amino)hexanoic Acid; 6-(((4,4-Difluoro-5-((2-Thienyl)-4-Bora-3a,4a-Diaza-s-Indacene-3-yl)styryloxy)acetyl)aminohexanoic Acid; 6-(((4,4-Difluoro-5-(2-Pyrrolyl)-4-Bora-3a,4a-Diaza-s-Indacene-3-yl) Styryloxy)Acetyl)Aminohexanoic Acid; 5-butyl-4,4-difluoro-4-bora-3a,4a-diaza-s-indacene-3-nonanoic acid; 5-decyl-4,4-difluoro-4-bora-3a,4a-diaza-s-indacene-3-propionic acid; 4,4-difluoro-5,7-dimethyl-4-bora-3a,4a-diaza-s-indacene-3-dodecanoic acid; 4,4-difluoro-5,7-dimethyl-4-bora-3a,4a-diaza-s-indacene-3-hexadecanoic acid; 4,4-difluoro-5,7-dimethyl-4-bora-3a,4a-diaza-s-indacene-3-pentanoic acid; 4,4-difluoro-5,7-dimethyl-4-bora-3a,4a-diaza-s-indacene-3-undecanoic acid; 4,4-difluoro-5,7-diphenyl-4-bora-3a,4a-diaza-s-indacene-3-dodecanoic acid; 4,4-difluoro-5-methyl-4-bora-3a,4a-diaza-s-indacene-3-dodecanoic acid; 4,4-difluoro-5-octyl-4-bora-3a,4a-diaza-s-indacene-3-pentanoic acid; 4,4-difluoro-5-(4-phenyl-1,3-butadienyl)-4-bora-3a,4a-diaza-s-indacene-3-pentanoic acid; 4,4-difluoro-5-(4-phenyl-1,3-butadienyl)-4-bora-3a,4a-diaza-s-indacene-3-undecanoic acid; 4,4-difluoro-5-(2-thienyl)-4-bora-3a,4a-diaza-s-indacene-3-dodecanoic acid; 2-(4,4-difluoro-5,7-dimethyl-4-bora-3a,4a-diaza-s-indacene-3-dodecanoyl)-1-hexadecanoyl-sn-glycero-3-phosphocholine; 2-(4,4-difluoro-5,7-dimethyl-4-bora-3a,4a-diaza-s-indacene-3-pentanoyl)-1-hexadecanoyl-sn-glycero-3-phosphocholine; 2-(4,4-difluoro-5-methyl-4-bora-3a,4a-diaza-s-indacene-3-dodecanoyl)-1-hexadecanoyl-sn-glycero-3-phosphocholine; 2-(4,4-difluoro-5-octyl-4-bora-3a,4a-diaza-s-indacene-3-pentanoyl)-1-hexadecanoyl-sn-glycero-3-phosphocholine; 2-(4,4-difluoro-5-(4-phenyl-1,3-butadienyl)-4-bora-3a,4a-diaza-s-indacene-3-pentanoyl)-1-hexadecanoyl-sn-glycero-3-phosphocholine; 2-(4,4-difluoro-5,7-dimethyl-4-bora-3a,4a-diaza-s-indacene-3-pentanoyl)-1-hexadecanoyl-sn-glycero-3-phosphate; N-(4,4-difluoro-5,7-dimethyl-4-bora-3a,4a-diaza-s-indacene-3-propionyl)-1,2-dihexadecanoyl-sn-glycero-3-phosphoethanolamine; N-(4,4-difluoro-5,7-dimethyl-4-bora-3a,4a-diaza-s-indacene-3-propionyl)-1,2-dihexanoyl-sn-glycero-3-phosphoethanolamine; cholesteryl 4,4-difluoro-5,7-dimethyl-4-bora-3a,4a-diaza-s-indacene-3-dodecanoate; cholesteryl 4,4-difluoro-5-(4-methoxyphenyl)-4-bora-3a,4a-diaza-s-indacene-3-undecanoate; cholesteryl 4,4-difluoro-5-(2-pyrrolyl)-4-bora-3a,4a-diaza-s-indacene-3-undecanoate; 4,4-difluoro-1,3,5,7,8-pentamethyl-4-bora-3a,4a-diaza-s-indacene; 4,4-difluoro-1,3,5,7-tetramethyl-4-bora-3a,4a-diaza-s-indacene; N-(4,4-Difluoro-5,7-Dimethyl-4-Bora-3a,4a-Diaza-s-Indacene-3-yl)Methyl)Iodoacetamide; N-(4,4-Difluoro-1,3,5,7-Tetramethyl-4-Bora-3a,4a-Diaza-s-Indacene-2-yl)Iodoacetamide; 8-Bromomethyl-4,4-Difluoro-1,3,5,7-Tetramethyl-4-Bora-3a,4a-Diaza-s-Indacene; or salts and/or ester derivatives thereof. In some embodiments, a pharmaceutically acceptable salt includes sodium, diammonium, and triethylammonium. In some embodiments, a pharmaceutically acceptable ester derivative includes succinimidyl ester and sulfosuccinimidyl ester derivatives.

Also contemplated herein are the BODIPY compounds described in Ulrich, G. et al., Angew. Chem. Int. Ed. 2008, 47: 1184-1201; Ziessel, R. et al., New J Chem. 2007, 31: 496-501; and Loudet, A. and Burgess, K., Chem. Rev. 2007, 107: 4891-4932, Jiang, X-D et al., Org. Letters 2012 14(1): 248-251; Zhu, S. et al., Org. Letters, 2011 13(3): 438-441; Bura, T. and Ziessel, R., Org. Letters 2011 13(12): 3072-3075; Niu, S. L. et al., Org. Letters 2009 11(10): 2049-2052; Li, L. et al., JOC 2008 73: 1963-1970, and Tahtaoui, C. et al., JOC 2007 72: 269-272.

In some cases, BODIPY fluorophores can include a group having the structure:

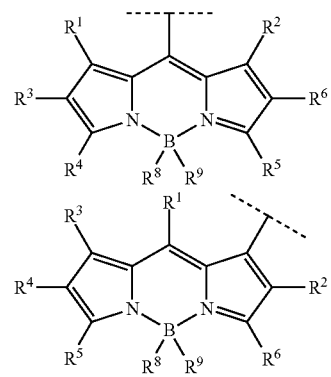

-continued

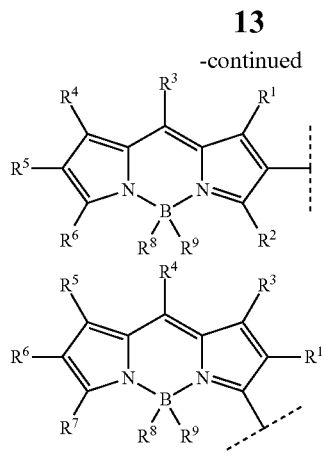

or a salt thereof,
wherein:
- $R^1$ and $R^2$ are selected from the group consisting of: H, $(C_1-C_6)$alkyl, $(C_1-C_6)$haloalkyl, $(C_2-C_6)$alkenyl, $(C_2-C_6)$alkynyl, $(C_1-C_6)$alkoxy, $-COR^{10}$, $-CO_2R^{10}$, $-SOR^{12}$, $-SO_2R^{12}$, $-NR^{10}R^{11}$, $-NO_2$, $(C_3-C_{10})$carbocyclyl, $(C_6-C_{10})$aryl, 4-10 membered heterocyclyl, and 5-10 membered heteroaryl, each of which is independently substituted or unsubstituted, and wherein if both $R^1$ and $R^2$ are present, no more than one of $R^1$ and $R^2$ is H;
- $R^3$, $R^4$, $R^5$, $R^6$, and $R^7$ are independently selected from H, $(C_1-C_6)$alkyl, $(C_1-C_6)$haloalkyl, $(C_2-C_6)$alkenyl, $(C_2-C_6)$alkynyl, $(C_1-C_6)$alkoxy, $-SO_3H$, $(C_3-C_{10})$carbocyclyl, $(C_6-C_{10})$aryl, 4-10 membered heterocyclyl, 5-10 membered heteroaryl, each of which is independently substituted or unsubstituted, and a reactive moiety;
- $R^8$ and $R^9$ are independently selected from halogen (e.g., fluorine), $(C_1-C_6)$alkyl, $(C_2-C_6)$alkynyl, $-CO_2R^{10}$, $(C_1-C_6)$alkoxy, O(4 membered heterocyclyl), $-O-(C_1-C_6)$alkyl-O(nPEG), each of which is independently substituted or unsubstituted;
- each $R^{10}$ and $R^{11}$ are independently selected from H and $(C_1-C_6)$alkyl;
- each $R^{12}$ is independently a $(C_6-C_{10})$aryl.

In some embodiments, if one of $R^1$ or $R^2$ is H, the other can be a $(C_1-C_6)$alkyl, $(C_3-C_{10})$carbocyclyl, $(C_6-C_{10})$aryl, or 5-10 membered heteroaryl. For example, phenyl, cyclohexyl, pyridyl, cyclopentyl, tert-butyl, or isopropyl. In some embodiments, $R^1$ and $R^2$ are independently selected from methyl, ethyl, isopropyl, and tert-butyl.

In some embodiments, $R^3$, $R^4$, $R^5$, $R^6$, and $R^7$ are independently selected from H, $(C_1-C_6)$alkyl, $(C_2-C_6)$alkenyl, $(C_6-C_{10})$aryl, and 5-10 membered heteroaryl, each of which is independently substituted or unsubstituted. For example, $R^3$, $R^4$, $R^5$, $R^6$, and $R^7$ can be independently selected from H, methyl, ethyl,

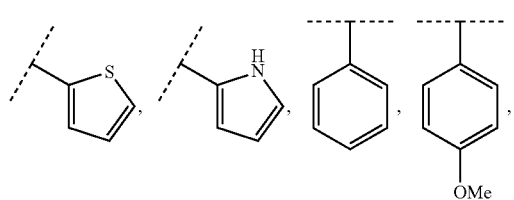

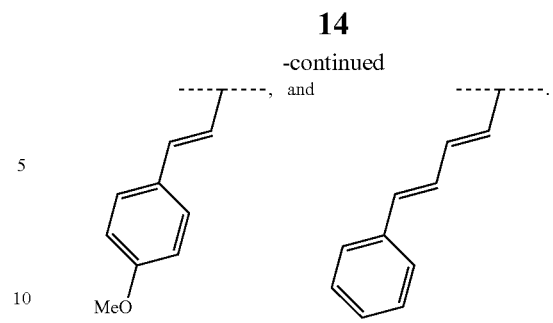

$R^8$ and $R^9$ are independently selected from halogen (e.g., fluorine), $(C_2-C_6)$alkynyl, $-CO_2R^{10}$, $(C_1-C_6)$alkoxy, O(4 membered heterocyclyl), and $-O-(C_1-C_6)$alkyl-O(nPEG), each of which is independently substituted or unsubstituted. For example, $R^8$ and $R^9$ can be independently selected from F, $-OCO_2H$, $-OCH_3$,

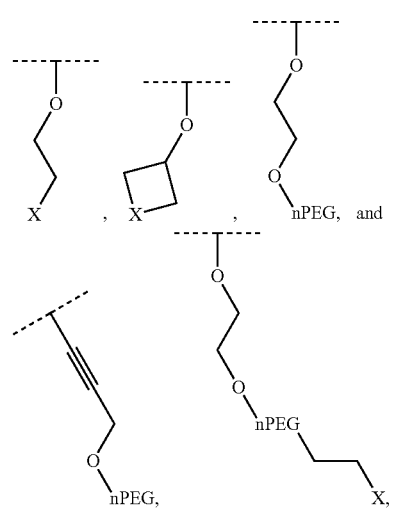

wherein X is O, N, or S, and nPEG is a polyethylene glycol polymer.

Coumarin fluorophores include, for example, 2H-chromen-2-one, umbelliferone (7-hydroxycoumarin), aesculetin (6,7-dihydroxycoumarin), herniarin (7-methoxycoumarin), psoralen, and imperatorin. In some embodiments, a coumarin fluorophore includes a group selected from:

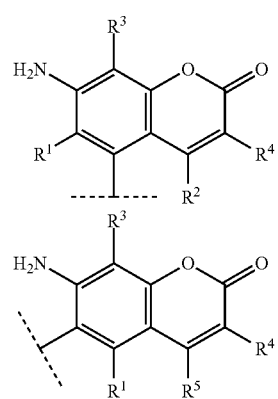

-continued

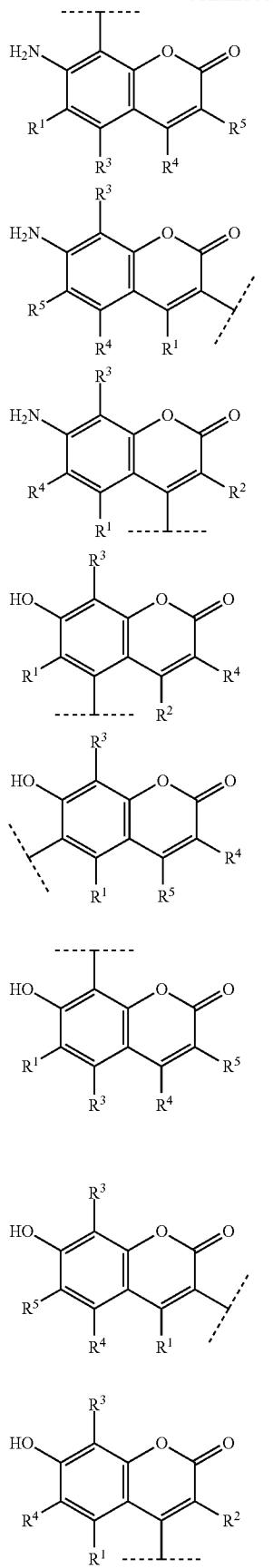

-continued

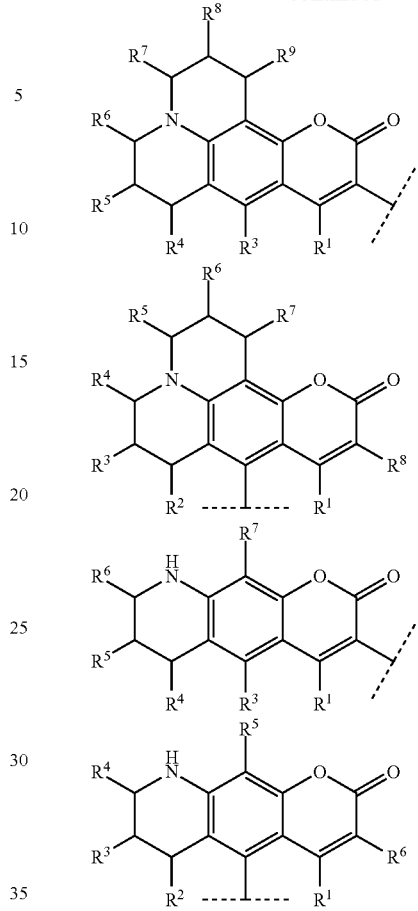

or a salt thereof,
wherein:
$R^1$ and $R^2$ are selected from the group consisting of: H, $(C_1-C_6)$alkyl, $(C_1-C_6)$haloalkyl, $(C_2-C_6)$alkenyl, $(C_2-C_6)$alkynyl, $(C_1-C_6)$alkoxy, —$COR^{10}$, —$CO_2R^{10}$, —$SOR^{12}$, —$SO_2R^{12}$, —$NR^{10}R^{11}$, —$NO_2$, $(C_3-C_{10})$carbocyclyl, $(C_6-C_{10})$aryl, 4-10 membered heterocyclyl, and 5-10 membered heteroaryl, each of which is independently substituted or unsubstituted;
$R^3$, $R^4$, $R^5$, $R^6$, $R^7$, $R^8$, and $R^9$ are independently selected from H, $(C_1-C_6)$alkyl, $(C_1-C_6)$haloalkyl, $(C_2-C_6)$alkenyl, $(C_2-C_6)$alkynyl, $(C_1-C_6)$alkoxy, —$SO_3H$, $(C_3-C_{10})$carbocyclyl, $(C_6-C_{10})$aryl, 4-10 membered heterocyclyl, 5-10 membered heteroaryl, each of which is independently substituted or unsubstituted, and a reactive moiety;
each $R^{10}$ and $R^{11}$ are independently selected from H and $(C_1-C_6)$alkyl; and
each $R^{12}$ is independently a $(C_6-C_{10})$aryl.

In some cases, wherein if both $R^1$ and $R^2$ are present, no more than one of $R^1$ and $R^2$ is H (i.e., at least one of $R^1$ and $R^2$ is not H). In some of these embodiments, if one of $R^1$ or $R^2$ is H, the other can be a $(C_1-C_6)$alkyl, $(C_3-C_{10})$carbocyclyl, $(C_6-C_{10})$aryl, or 5-10 membered heteroaryl. For example, phenyl, cyclohexyl, pyridyl, cyclopentyl, tert-butyl, or isopropyl. In some embodiments, $R^1$ and $R^2$ are independently selected from H, methyl, ethyl, isopropyl, and tert-butyl. In some embodiments, $R^3$, $R^4$, $R^5$, $R^6$, $R^7$, $R^8$, and $R^9$, when present, are H.

In some embodiments, a coumarin fluorophore is selected from the group consisting of:

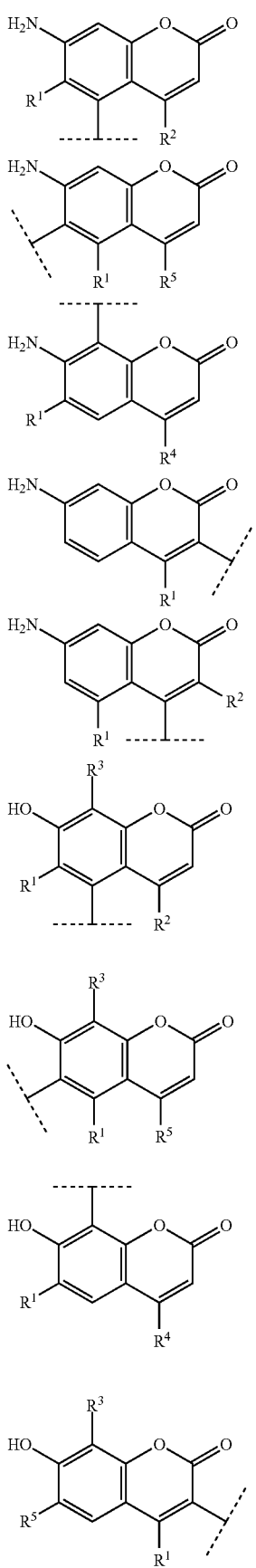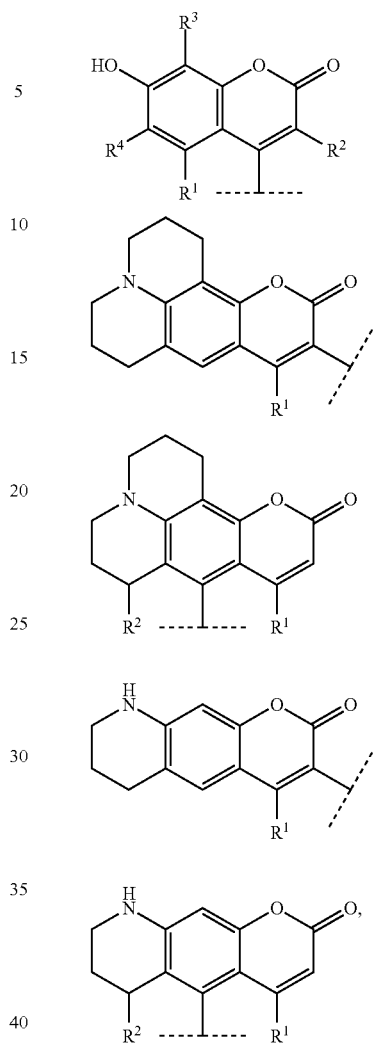
or a salt thereof.
For example, a coumarin fluorophore can include:
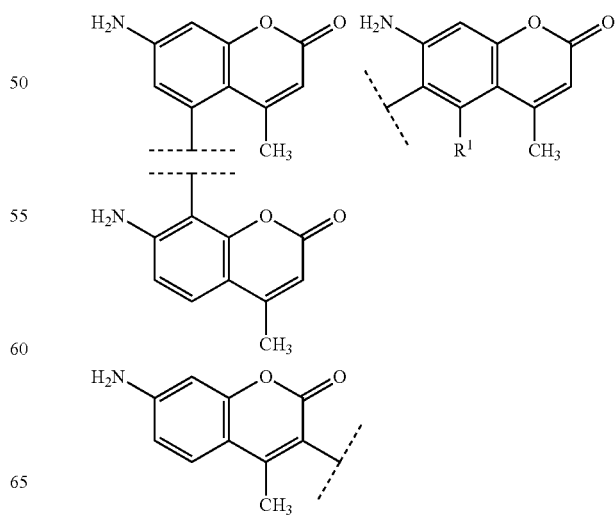

19
-continued

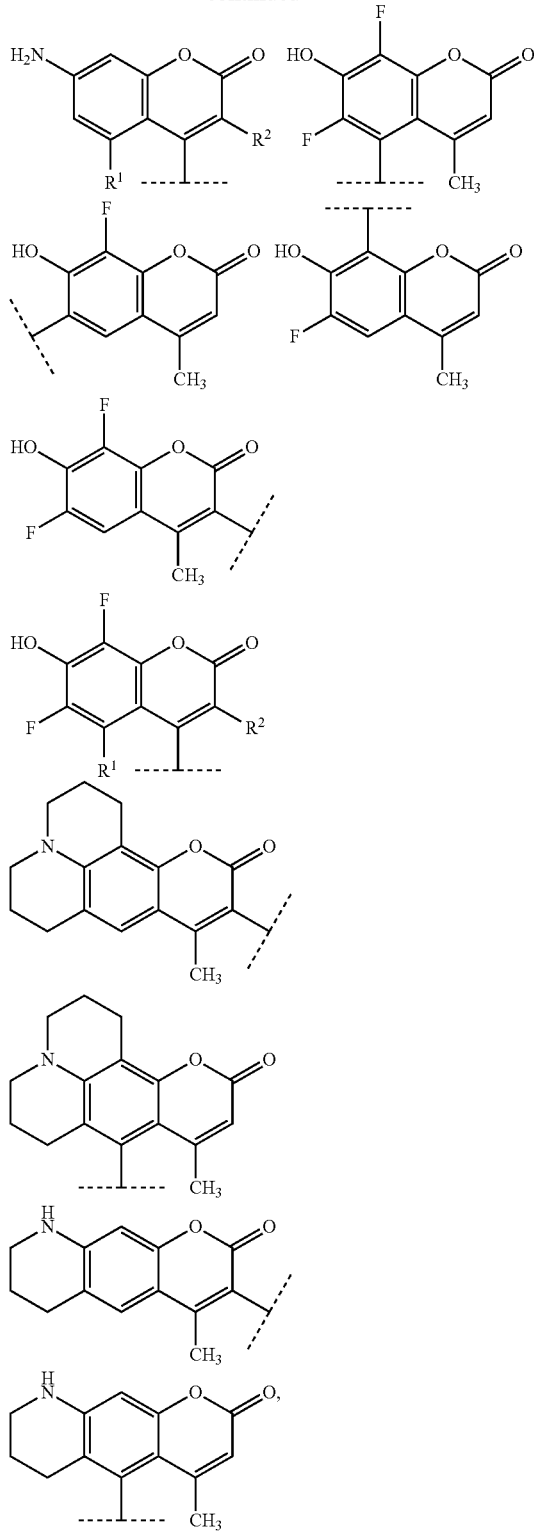

or a salt thereof.

A fluorophore can be a rhodamine fluorophore. Non-limiting examples include rhodamine, rhodamine B, rhodamine 6G, rhodamine 123, carboxytetramethylrhodamine (TAMRA), tetramethylrhodamine (TMR) and its isothiocyanate derivative (TRITC), sulforhodamine 101 (and its sulfonyl chloride form Texas Red), Rhodamine Red, Alexa 546, Alexa 555, Alexa 633, DyLight 550, and DyLight 633.

In some cases, a rhodamine fluorophore can be a group selected from:

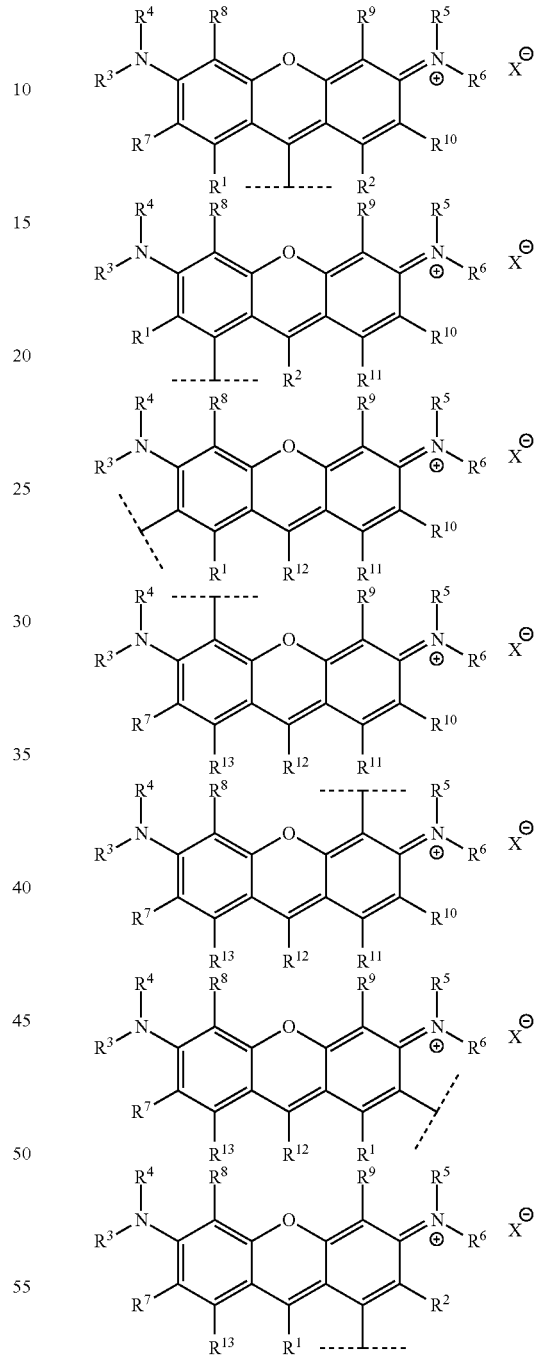

or a salt thereof,
wherein:
X is a counter anion;
$R^1$ and $R^2$ are selected from the group consisting of: H, $(C_1-C_6)$alkyl, $(C_1-C_6)$haloalkyl, $(C_2-C_6)$alkenyl, $(C_2-C_6)$alkynyl, $(C_1-C_6)$alkoxy, —$COR^{14}$, —$CO_2R^{14}$, —$SOR^{16}$, —$SO_2R^{16}$, —$NR^{14}R^{15}$, —$NO_2$, $(C_3-C_{10})$carbocyclyl, ($C_6$-$C_{10}$)aryl, 4-10 membered heterocyclyl, and 5-10 membered heteroaryl, each of which is independently substituted or unsubstituted;

$R^3$, $R^4$, $R^5$, $R^6$, $R^7$, $R^8$, $R^9$, $R^{10}$, $R^{11}$, $R^{12}$, and $R^{13}$ are independently selected from the group consisting of: H, ($C_1$-$C_6$)alkyl, ($C_1$-$C_6$)haloalkyl, ($C_2$-$C_6$)alkenyl, ($C_2$-$C_6$) alkynyl, ($C_1$-$C_6$)alkoxy, —$SO_3$, —$SO_3H$, ($C_3$-$C_{10}$)carbocyclyl, ($C_6$-$C_{10}$)aryl, 4-10 membered heterocyclyl, 5-10 membered heteroaryl, each of which is independently substituted or unsubstituted, and a reactive moiety; wherein, optionally, one or more of the pairs $R^3$ and $R^7$, $R^4$ and $R^8$, $R^5$ and $R^9$, and $R^6$ and $R^{10}$ come together to form a saturated or unsaturated ring structure with the carbons or nitrogens to which they are attached, any of which can be substituted or unsubstituted;

each $R^{14}$ and $R^{15}$ are independently selected from H and ($C_1$-$C_6$)alkyl; and each $R^{16}$ is independently a ($C_6$-$C_{10}$)aryl.

In some cases, wherein if both $R^1$ and $R^2$ are present, no more than one of $R^1$ and $R^2$ is H (i.e., at least one of $R^1$ and $R^2$ is not H). In some of these embodiments, if one of R or $R^2$ is H, the other can be a ($C_1$-$C_6$)alkyl, ($C_3$-$C_{10}$)carbocyclyl, ($C_6$-$C_{10}$)aryl, or 5-10 membered heteroaryl. For example, phenyl, cyclohexyl, pyridyl, cyclopentyl, tert-butyl, or isopropyl. In some embodiments, $R^1$ and $R^2$ are independently selected from H, methyl, ethyl, isopropyl, and tert-butyl.

Fluorescein fluorophores can include fluorescein, fluorescein isothiocyanate (FITC), 6-FAM phosphoramidite, esters of fluorescein including succinimidyl esters (NHS-fluorescein), pentafluorophenyl esters (PFP) and tetrafluorophenyl esters (TFP), eosin, carboxyfluorescein, fluorescein amidite (FAM), merbromin, erythrosine, Rose Bengal, and DyLight Fluor agents. In some embodiments, a fluorescein fluorophore is a group selected from:

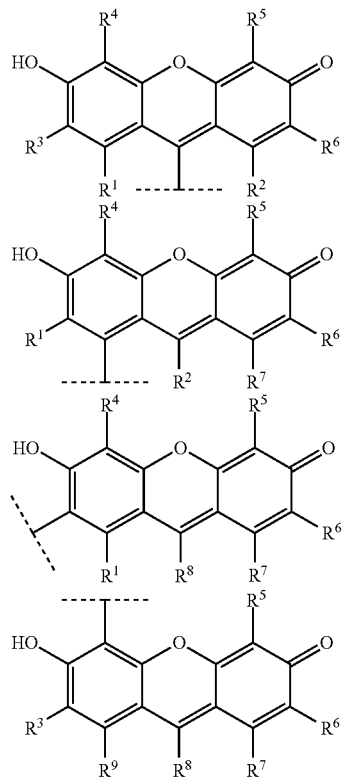

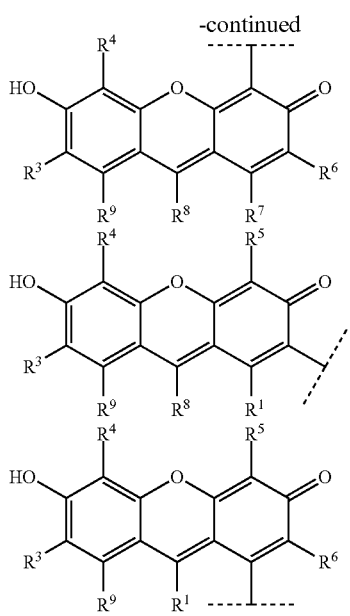

or a salt thereof,
wherein:
$R^1$ and $R^2$ are selected from the group consisting of: H, ($C_1$-$C_6$)alkyl, ($C_1$-$C_6$)haloalkyl, ($C_2$-$C_6$)alkenyl, ($C_2$-$C_6$) alkynyl, ($C_1$-$C_6$)alkoxy, —$COR^{10}$, —$CO_2R^{10}$, —$SOR^{12}$, —$SO_2R^{12}$, —$NR^{10}R^{11}$, —$NO_2$, ($C_3$-$C_{10}$)carbocyclyl, ($C_6$-$C_{10}$)aryl, 4-10 membered heterocyclyl, and 5-10 membered heteroaryl, each of which is independently substituted or unsubstituted;

$R^3$, $R^4$, $R^5$, $R^6$, $R^7$, $R^8$, and $R^9$ are independently selected from the group consisting of: H, ($C_1$-$C_6$)alkyl, ($C_1$-$C_6$) haloalkyl, ($C_2$-$C_6$)alkenyl, ($C_2$-$C_6$)alkynyl, ($C_1$-$C_6$) alkoxy, ($C_3$-$C_{10}$)carbocyclyl, ($C_6$-$C_{10}$)aryl, 4-10 membered heterocyclyl, 5-10 membered heteroaryl, each of which is independently substituted or unsubstituted, and a reactive moiety;

each $R^{10}$ and $R^{11}$ are independently selected from H and ($C_1$-$C_6$)alkyl; and each $R^{12}$ is independently a ($C_6$-$C_{10}$)aryl.

In some cases, wherein if both $R^1$ and $R^2$ are present, no more than one of $R^1$ and $R^2$ is H (i.e., at least one of $R^1$ and $R^2$ is not H). In some of these embodiments, if one of $R^1$ or $R^2$ is H, the other can be a ($C_1$-$C_6$)alkyl, ($C_3$-$C_{10}$)carbocyclyl, ($C_6$-$C_{10}$)aryl, or 5-10 membered heteroaryl. For example, phenyl, cyclohexyl, pyridyl, cyclopentyl, tert-butyl, or isopropyl. In some embodiments, $R^1$ and $R^2$ are independently selected from H, methyl, ethyl, isopropyl, and tert-butyl.

A fluorophore, as described herein, can include a combination fluorophore based on a combination of rhodamine and fluorescein. For example, a fluorophore can be selected from:

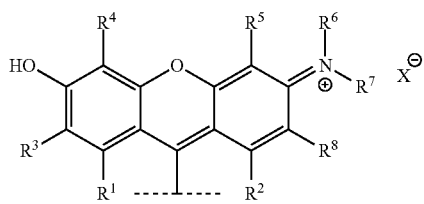

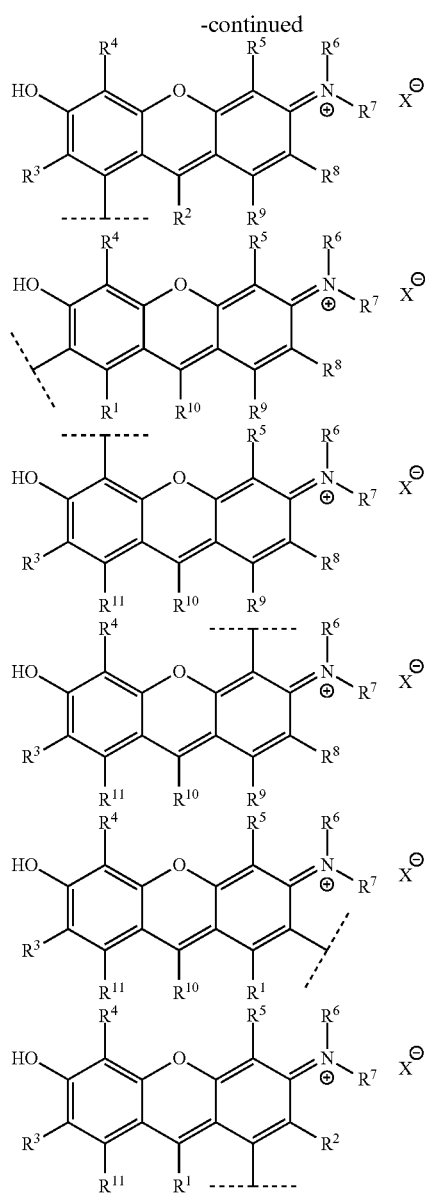

or a salt thereof,
wherein:
X is a counter anion;
R¹ and R² are selected from the group consisting of: H, (C₁-C₆)alkyl, (C₁-C₆)haloalkyl, (C₂-C₆)alkenyl, (C₂-C₆)alkynyl, (C₁-C₆)alkoxy, —COR¹², —CO₂R¹², —SOR¹⁴, —SO₂R¹⁴, —NR¹²R¹³, —NO₂, (C₃-C₁₀)carbocyclyl, (C₆-C₁₀)aryl, 4-10 membered heterocyclyl, and 5-10 membered heteroaryl, each of which is independently substituted or unsubstituted;
R³, R⁴, R⁵, R⁶, R⁷, R⁸, R⁹, R¹⁰, and R¹¹ are independently selected from the group consisting of: H, (C₁-C₆)alkyl, (C₁-C₆)haloalkyl, (C₂-C₆)alkenyl, (C₂-C₆)alkynyl, (C₁-C₆)alkoxy, —SO₃, —SO₃H, (C₃-C₁₀)carbocyclyl, (C₆-C₁₀)aryl, 4-10 membered heterocyclyl, 5-10 membered heteroaryl, each of which is independently substituted or unsubstituted, and a reactive moiety; wherein, optionally, one or more of the pairs R⁵ and R⁶, and R⁷ and R⁸ come together to form a saturated or unsaturated ring structure with the carbons or nitrogens to which they are attached, any of which can be substituted or unsubstituted;

each R¹² and R¹³ are independently selected from H and (C₁-C₆)alkyl; and
each R¹⁴ is independently a (C₆-C₁₀)aryl.

In some cases, wherein if both R¹ and R² are present, no more than one of R¹ and R² is H (i.e., at least one of R¹ and R² is not H). In some of these embodiments, if one of R¹ or R² is H, the other can be a (C₁-C₆)alkyl, (C₃-C₁₀)carbocyclyl, (C₆-C₁₀)aryl, or 5-10 membered heteroaryl. For example, phenyl, cyclohexyl, pyridyl, cyclopentyl, tert-butyl, or isopropyl. In some embodiments, R¹ and R² are independently selected from H, methyl, ethyl, isopropyl, and tert-butyl.

In some embodiments, a fluorophore can be a group selected from:

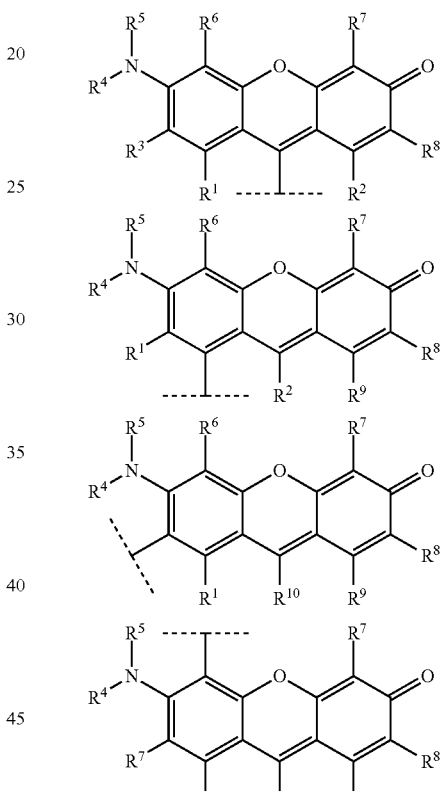

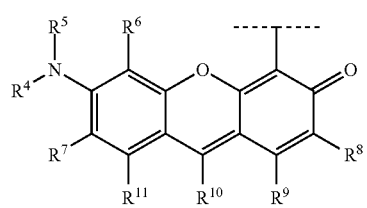

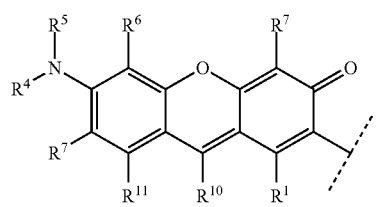

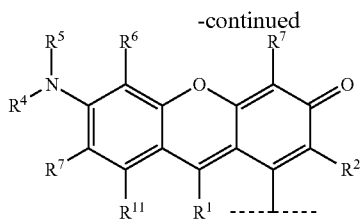

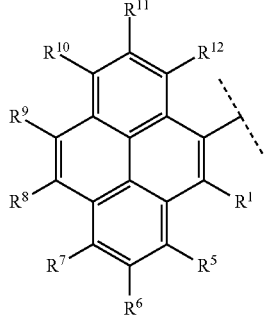

or a salt thereof, wherein:

R¹ and R² are selected from the group consisting of: H, (C₁-C₆)alkyl, (C₁-C₆)haloalkyl, (C₂-C₆)alkenyl, (C₂-C₆)alkynyl, (C₁-C₆)alkoxy, —COR¹², —CO₂R¹², —SOR¹⁴, —SO₂R¹⁴, —NR¹²R¹³, —NO₂, (C₃-C₁₀)carbocyclyl, (C₆-C₁₀)aryl, 4-10 membered heterocyclyl, and 5-10 membered heteroaryl, each of which is independently substituted or unsubstituted;

R³, R⁴, R⁵, R⁶, R⁷, R⁸, R⁹, R¹⁰, and R¹¹ are independently selected from the group consisting of: H, (C₁-C₆)alkyl, (C₁-C₆)haloalkyl, (C₂-C₆)alkenyl, (C₂-C₆)alkynyl, (C₁-C₆)alkoxy, (C₃-C₁₀)carbocyclyl, (C₆-C₁₀)aryl, 4-10 membered heterocyclyl, 5-10 membered heteroaryl, each of which is independently substituted or unsubstituted, and a reactive moiety; wherein, optionally, one or more of the pairs R⁴ and R⁷, and R⁵ and R⁶ come together to form a saturated or unsaturated ring structure with the carbons or nitrogens to which they are attached, any of which can be substituted or unsubstituted;

each R¹² and R¹³ are independently selected from H and (C₁-C₆)alkyl; and each R¹⁴ is independently a (C₆-C₁₀)aryl.

In some cases, wherein if both R¹ and R² are present, no more than one of R¹ and R² is H (i.e., at least one of R¹ and R² is not H). In some of these embodiments, if one of R¹ or R² is H, the other can be a (C₁-C₆)alkyl, (C₃-C₁₀)carbocyclyl, (C₆-C₁₀)aryl, or 5-10 membered heteroaryl. For example, phenyl, cyclohexyl, pyridyl, cyclopentyl, tert-butyl, or isopropyl. In some embodiments, R¹ and R² are independently selected from H, methyl, ethyl, isopropyl, and tert-butyl.

A fluorophore can include a pyrene fluorophore. Non-limiting examples of a pyrene fluorophore include a group selected from:

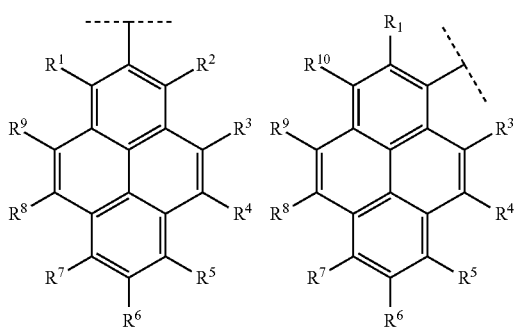

or a salt thereof, wherein:

R¹ and R² are selected from the group consisting of: H, (C₁-C₆)alkyl, (C₁-C₆)haloalkyl, (C₂-C₆)alkenyl, (C₂-C₆)alkynyl, (C₁-C₆)alkoxy, —COR¹³, —CO₂R¹³, —SOR¹⁵, —SO₂R¹⁵, —NR¹³R¹⁴, —NO₂, (C₃-C₁₀)carbocyclyl, (C₆-C₁₀)aryl, 4-10 membered heterocyclyl, and 5-10 membered heteroaryl, each of which is independently substituted or unsubstituted;

R³, R⁴, R⁵, R⁶, R⁷, R⁸, R⁹, R¹⁰, R¹¹, and R¹² are independently selected from the group consisting of: H, (C₁-C₆)alkyl, (C₁-C₆)haloalkyl, (C₂-C₆)alkenyl, (C₂-C₆)alkynyl, (C₁-C₆)alkoxy, —SO₃H, (C₃-C₁₀)carbocyclyl, (C₆-C₁₀)aryl, 4-10 membered heterocyclyl, 5-10 membered heteroaryl, each of which is independently substituted or unsubstituted, and a reactive moiety;

each R¹³ and R¹⁴ are independently selected from H and (C₁-C₆)alkyl; and each R¹⁵ is independently a (C₆-C₁₀)aryl.

In some cases, wherein if both R¹ and R² are present, no more than one of R¹ and R² is H (i.e., at least one of R¹ and R² is not H). In some of these embodiments, if one of R¹ or R² is H, the other can be a (C₁-C₆)alkyl, (C₃-C₁₀)carbocyclyl, (C₆-C₁₀)aryl, or 5-10 membered heteroaryl. For example, phenyl, cyclohexyl, pyridyl, cyclopentyl, tert-butyl, or isopropyl. In some embodiments, R¹ and R² are independently selected from H, methyl, ethyl, isopropyl, and tert-butyl.

Additional fluorophores may also be used in the compounds described herein, for example, cyanine fluorophores. For example, a fluorophore having the structure:

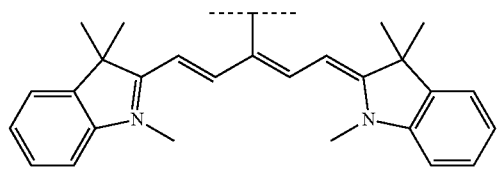

or a salt thereof. In some embodiments, the fluorophore can be an oxazine fluorophore. For example, the fluorophore can be selected from:

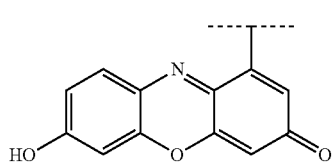

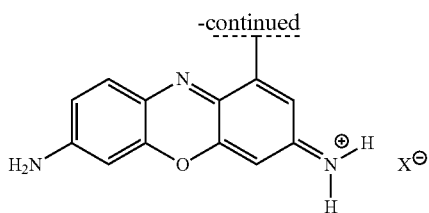

or a salt thereof, wherein X is a counter anion as described above. A fluorophore can also be an acridine fluorophore. For example, the fluorophore can be a compound having the structure:

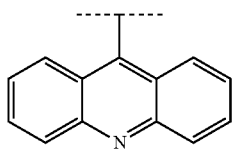

or a salt thereof. In some embodiments, a fluorophore can be an auramine O fluorophore. For example, a fluorophore can be a compound:

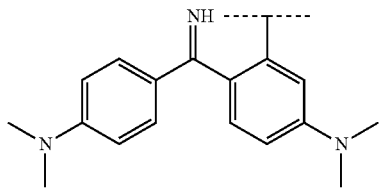

or a salt thereof. As for the fluorophores described previously, the location of attachment of the -L-Tz moiety may vary and the fluorophores may be further substituted to modify the steric and/or fluorescent characteristics of the compound.

A linker moiety can be a conjugated linker. The linker contains alternating single and multiple bonds and can be cyclic, acyclic, linear, or any combination thereof. For example, the linker can include an alkenyl, alkynyl, aryl, and/or heteroaryl moiety. In some embodiments, the linker can include an alkenyl and an aryl, an alkynyl and an aryl, an alkenyl and a heteroaryl, or an alkynyl and a heteroaryl. The structure of the linker must be such that the linker bridges and continues the conjugation of the fluorophore with that of the tetrazine so that a conjugated pi-system extends between these three moieties.

In some embodiments, a linker moiety can be an aromatic linker. For example, the aromatic linker can be a $(C_6\text{-}C_{10})$ aryl or 5-10 membered heteroaryl. In some embodiments, the aromatic linker is selected from the group consisting of:

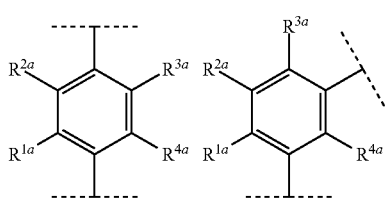

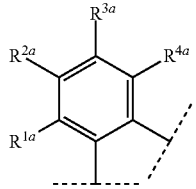

wherein:
$R^{1a}$, $R^{2a}$, $R^{3a}$, and $R^{4a}$ are selected from the group consisting of: H, $(C_1\text{-}C_6)$alkyl, $(C_1\text{-}C_6)$haloalkyl, $(C_2\text{-}C_6)$alkenyl, $(C_2\text{-}C_6)$alkynyl, $(C_1\text{-}C_6)$alkoxy, —$COR^{13}$, —$CO_2R^{13}$, —$SOR^{15}$, —$SO_2R^{15}$, —$NR^{13}R^{14}$, —$NO_2$, $(C_3\text{-}C_{10})$carbocyclyl, $(C_6\text{-}C_{10})$aryl, 4-10 membered heterocyclyl, and 5-10 membered heteroaryl, each of which is independently substituted or unsubstituted.

Additional examples of aromatic linkers include:

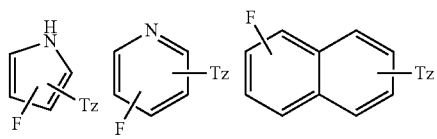

In some embodiments, a linker is

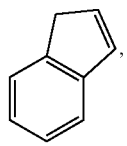

wherein the linker is substituted by F and Tz as exemplified above. As above, the linkers described herein can be further substituted to modify the sterics of the linker and the orientation of the L-Tz moiety with respect to the F moiety.

Linkers, as provided herein, can also be selected from a substituted or unsubstituted heteroaryl or heterocyclyls. Non-limiting examples include:

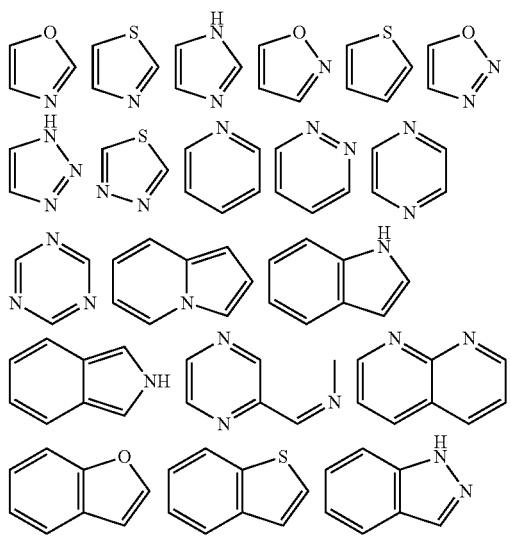

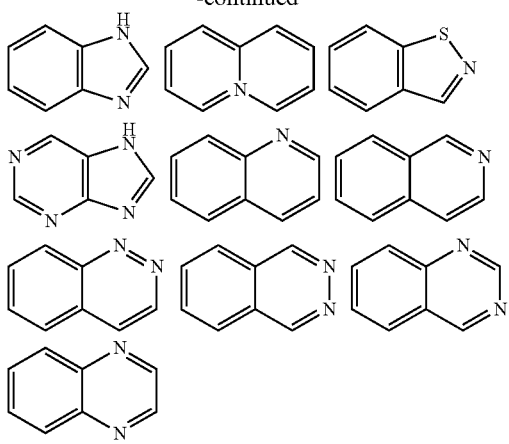

each of the above compounds is independently substituted by F and Tz (e.g., through a carbon-carbon bond). In addition, each of the compounds described above may be unsubstituted or substituted (e.g., by one or more $R_x$ as described below). In some embodiments, the heteroaryl or heterocyclic linkers provided herein can include an alkenyl or alkynyl linkage between the fluorophore and/or the tetrazine moiety.

In some embodiments, a linker can be selected from the group consisting of:

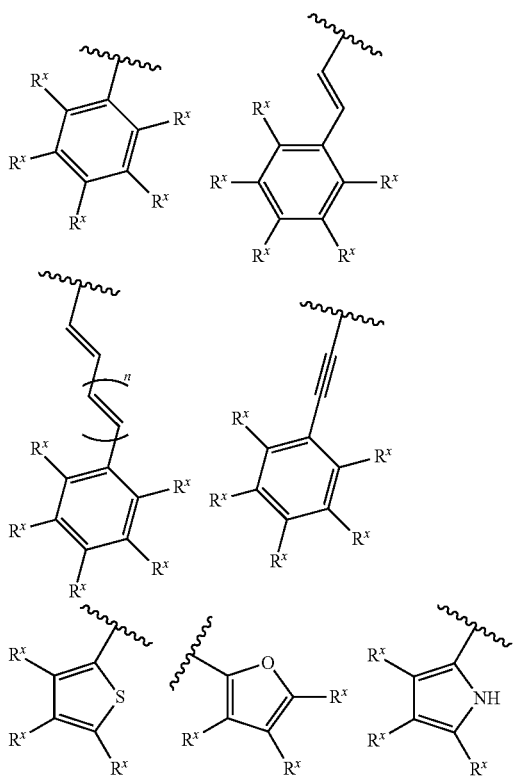

wherein n is an integer from 1 to 10 (e.g., 1 to 4); and each $R^x$ is independently selected from the group consisting of H, $(C_1\text{-}C_6)$alkyl, $(C_1\text{-}C_6)$alkoxyl, and a tetrazine moiety as provided herein. For example, each $R^x$ can be independently selected from H, methyl, ethyl, propyl, isopropyl, methoxy, and a tetrazine moiety as provided herein.

The tetrazine moiety in the compound of Formula (I) can be a substituted or unsubstituted tetrazine. In some embodiments, the tetrazine moiety is tetrazine. In other embodiments, the tetrazine is substituted with a substituent selected from $Cy^1$, $C_{1\text{-}6}$ alkyl, $C_{2\text{-}6}$ alkenyl, $C_{2\text{-}6}$ alkynyl, halo, $C_{1\text{-}6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$ and $S(O)_2NR^{c1}R^{d1}$, wherein each $Cy^1$ is independently $C_{6\text{-}10}$ aryl, $C_{3\text{-}10}$ carbocyclyl, 5-10 membered heteroaryl or 4-10 membered heterocyclyl, each of which is unsubstituted or substituted by 1, 2, 3, 4 or 5 substituents independently selected from $C_{1\text{-}6}$ alkyl, $C_{2\text{-}6}$ alkenyl, $C_{2\text{-}6}$ alkynyl, halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and oxo;

each $R^{a1}$, $R^{b1}$, $R^{c1}$, $R^{d1}$ is independently selected from H, $C_{1\text{-}6}$ alkyl, $C_{1\text{-}4}$ haloalkyl, $C_{2\text{-}6}$ alkenyl, $C_{2\text{-}6}$ alkynyl, $C_{6\text{-}10}$ aryl, $C_{3\text{-}10}$ carbocyclyl, 5-10 membered heteroaryl, 4-10 membered heterocyclyl, $C_{6\text{-}10}$ aryl-$C_{1\text{-}4}$ alkyl, $C_{3\text{-}10}$ carbocyclyl-$C_{1\text{-}4}$ alkyl, (5-10 membered heteroaryl)-$C_{1\text{-}4}$ alkyl or (4-10 membered heterocyclyl)-$C_{1\text{-}4}$ alkyl.

For example, a tetrazine can be a moiety having the structure:

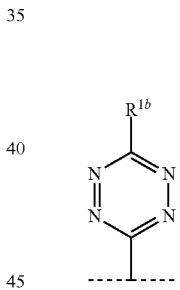

wherein:

$R^{1b}$ is selected from the group consisting of: H, $(C_1\text{-}C_6)$ alkyl, $(C_1\text{-}C_6)$haloalkyl, $(C_6\text{-}C_{10})$aryl, and 5-10 membered heteroaryl, each of which is independently substituted or unsubstituted.

For example, the tetrazine can be selected from:

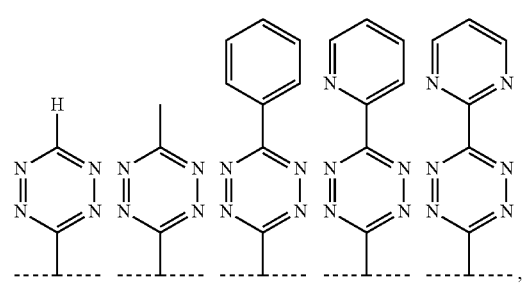

Non-limiting examples of a compound of Formula (I) include:
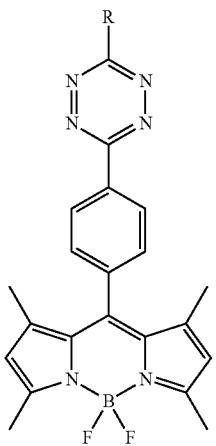
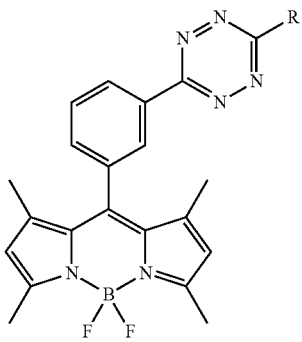
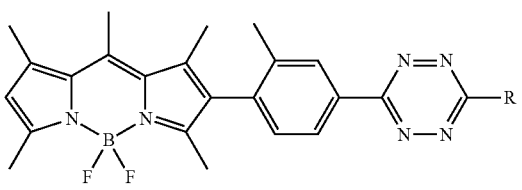
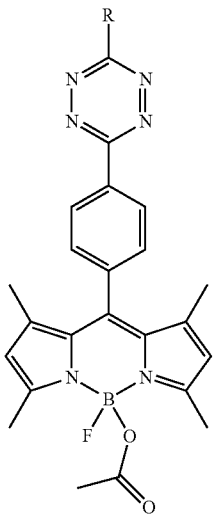
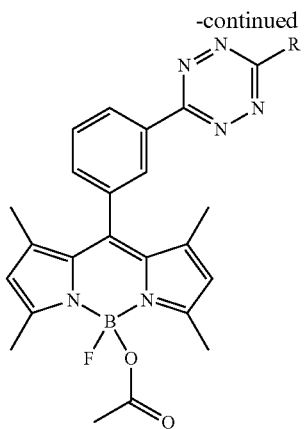
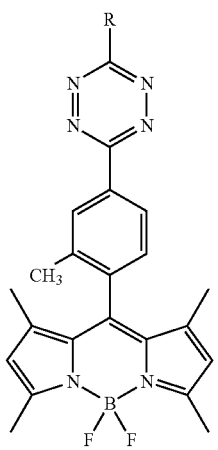
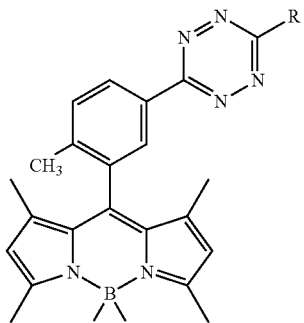
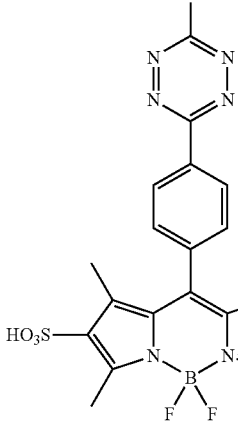

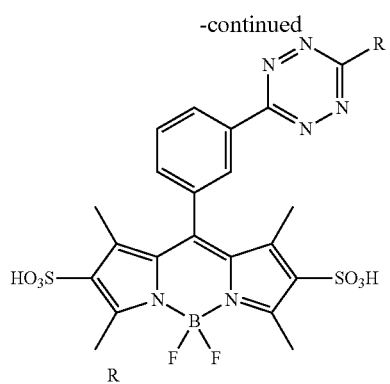
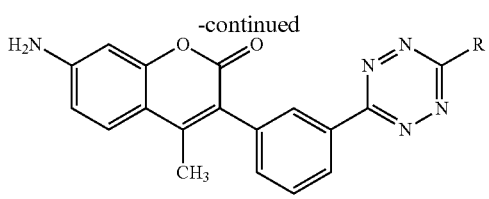
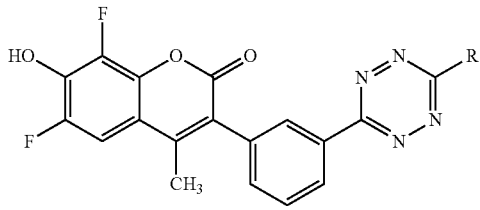
or a salt thereof, wherein each R is independently selected from H, (C$_1$-C$_6$)alkyl, (C$_1$-C$_6$)haloalkyl, (C$_6$-C$_{10}$)aryl, and 5-10 membered heteroaryl. In some embodiments, R is H or (C$_1$-C$_6$)alkyl, such as CH$_3$.
For example, a compound of Formula (I) can include:
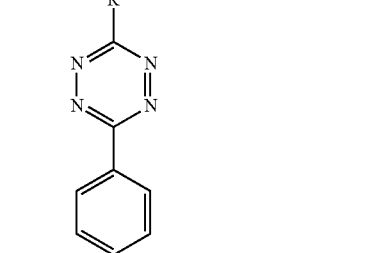
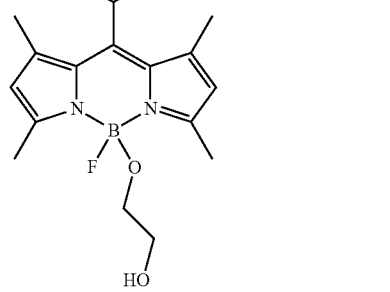
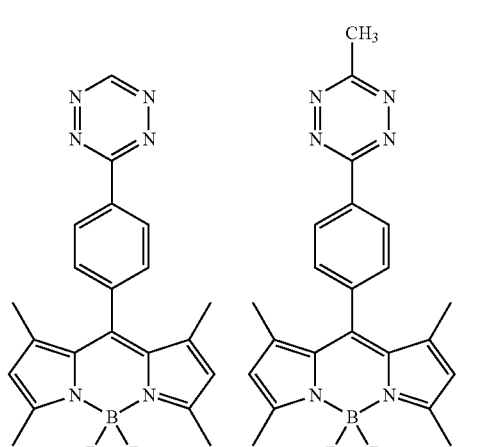
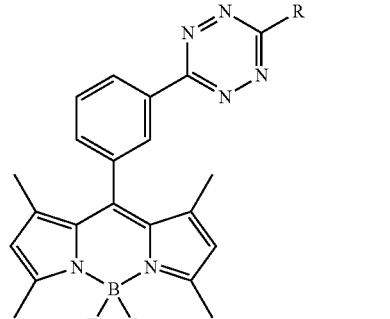
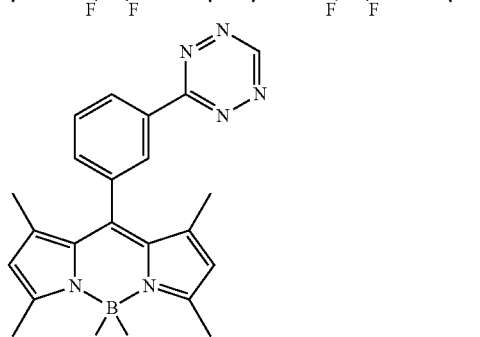
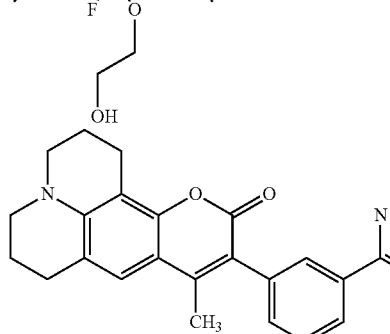
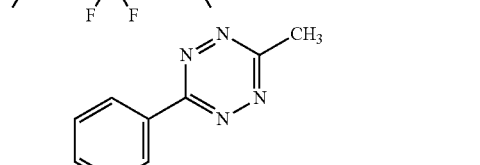
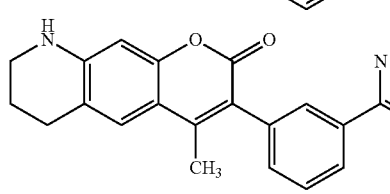
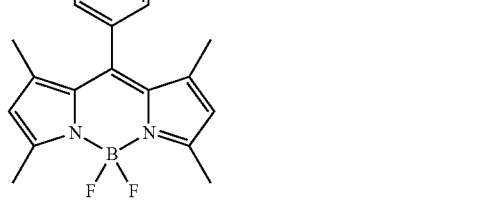

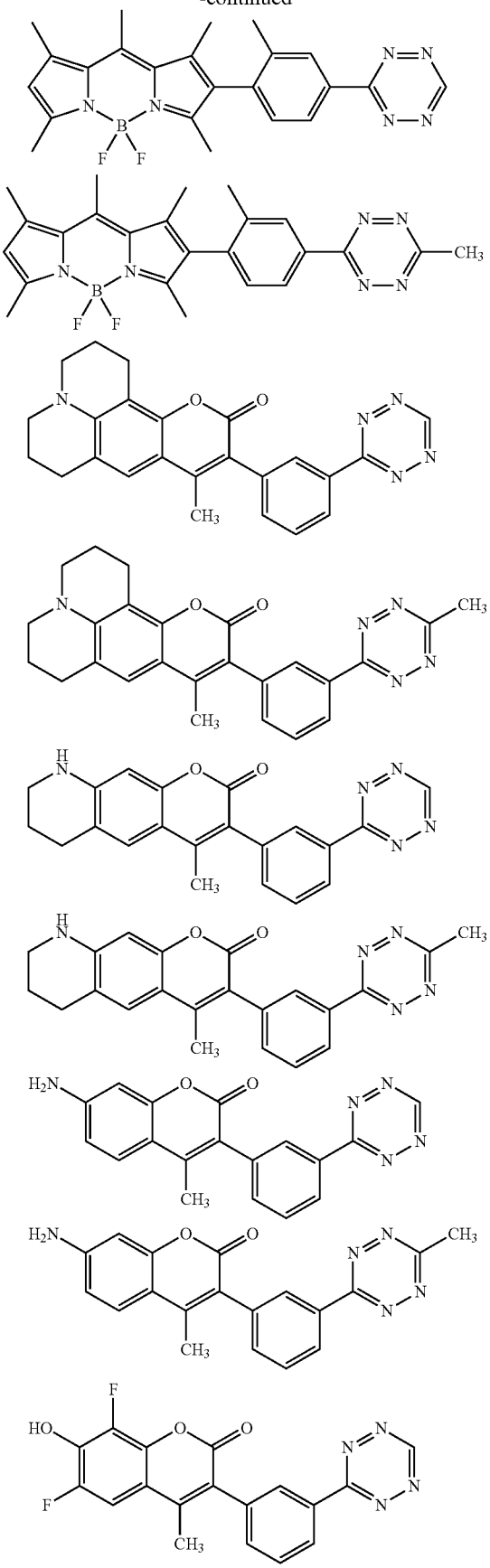

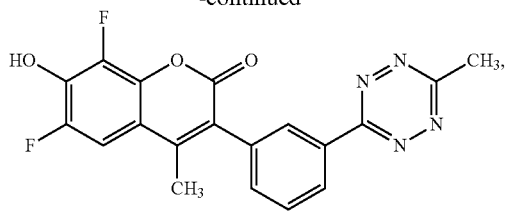

or a salt thereof.

Also provided herein is a compound of Formula (II):

F-Tz or a salt thereof, wherein F is a fluorophore and Tz is a substituted or unsubstituted tetrazine as described previously, and wherein the Tz and F moieties form a single conjugated pi-system. In some embodiments, the Tz and F moieties form a non-coplanar pi-system. For example, the Tz moiety can be oriented with respect to the F moiety such that the tetrazine transition dipole is either collinear with or parallel to the transition dipole of the fluorophore. The moieties F and Tz can be as defined for any of the embodiments described above.

Without being bound by any theory, the most TBET quenched probe may be one where the tetrazine is directly attached to the fluorophore. In non-planar compounds, the disruption in conjugation between the two systems can be provided by the fluorophore (e.g., by the steric effects of substituents on the fluorophore). In effect, the TBET connection between the two systems is the shortest possible (i.e., the single bond between the two moieties).

Non-limiting examples of a compound of Formula (II) include:

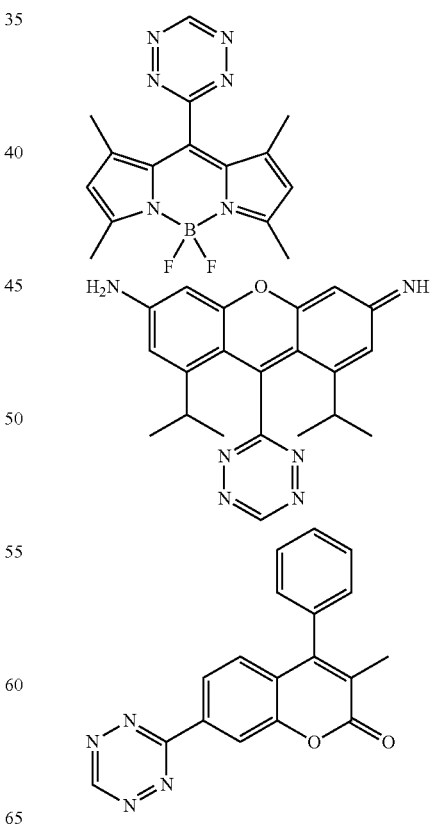

or a salt thereof.

This disclosure further provides a compound of Formula (III):

F-L-Z or a salt thereof, wherein:

F is a fluorophore;

L is a conjugated linker; and

Z is a moiety comprising the reaction product of a diene and a dienophile, wherein the diene is a tetrazine or a derivative thereof;

wherein the linker bridges the Z and F moieties in a single conjugated pi-system.

The single, conjugated pi-system may, in some embodiments, be non-coplanar due to steric factors within the compound that enforce a twist in the interchromophore linkage between the F and L-Z moieties. Such steric factors can originate from substituents on either the linker or on the fluorophore. Without being bound by theory, fluorescence can be increased when the L-Z moiety is oriented with respect to the F moiety such that the transition dipole of Z is either collinear with or parallel to the transition dipole of the fluorophore.

The fluorophore, linker, and tetrazine are as described above.

Z is a moiety formed through the reaction of a diene (e.g., tetrazine or a derivative thereof) and a dienophile using bioorthogonal chemistry. Bioconjugation methods using inverse electron demand Diels-Alder cycloadditions between tetrazines and highly strained dienophiles such as norbornene, strained cyclic alkenes, and trans-cyclooctene are known in the literature, however the tetrazine used has limited stability to aqueous media. (Blackman et al., 2008, *J Am Chem Soc*, 130, 13518-9; Devaraj et al., 2009, *Angew Chem Int Ed Engl*, 48, 7013-6; Devaraj et al., 2008, *Bioconjug Chem*, 19, 2297-9; Pipkorn et al., 2009, *J Pept Sci*, 15, 235-41).

Dienophiles useful in the compounds described herein include but are not limited to carbon containing dienophiles such as alkenes or alkynes, or compounds containing nitroso, carbonyl or imine groups. In some embodiments, the dienophile is a strained dienophile. As used herein, a "strained" dienophile has a dihedral angle that deviates from the idealized 180 degree dihedral angle. Alternatively, non-strained dienophiles (e.g., styrenes) and/or electron rich electrophiles (e.g., eneamines or vinyl ethers), can also be used with nitroso compounds. Alkenes as used herein refers to an alkyl group having one or more double carbon-carbon bonds such as an ethylene, propylene, and the like. Alkenes can also include cyclic, ring-strained alkenes such as trans-cyclooctene or norbornene carrying a double bond which induces significant ring strain and is thus highly reactive. Alkenes can also include more complex structures such as indoles and azaindoles, electron rich enamines. Heterodienophiles containing carbonyl, nitroso or imine groups can also be used. In some embodiments, the dienophile is a trans-cyclooctenol, e.g., (E)-cyclooct-4-enol. Additional examples of dienophiles include those described in Thalhammer, F. et al. *Tetrahedron Letters* 1990 31(47): 6851-6854. In some embodiments, the dienophile is a substituted or derivatized trans-cyclooctenol. For example, the hydroxyl moiety on the trans-cyclooctenol can be derivatized with a linker (e.g., a PEG linker) and/or a reactive moiety. In some embodiments, the trans-cyclooctenol is modified with a reactive moiety such as:

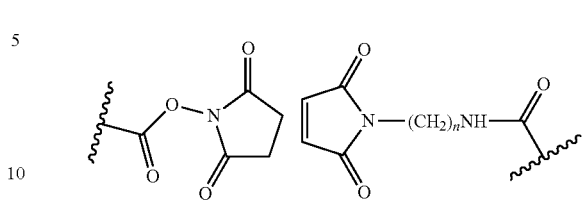

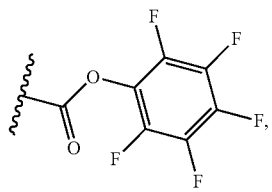

wherein n is an integer from 1 to 10; or a carbamate-linked PEG (e.g., a carbamate-linked PEGm, wherein m is an integer from 1 to 10) such as a carbamate-linked $PEG_2$ (TCOc):

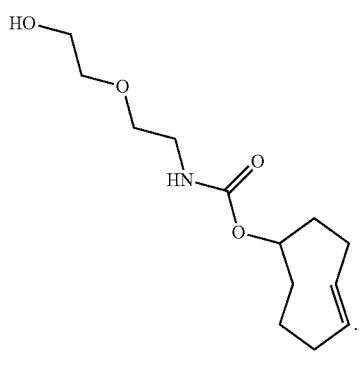

TCOc

Non-limiting examples of a compound of Formula (III) include:

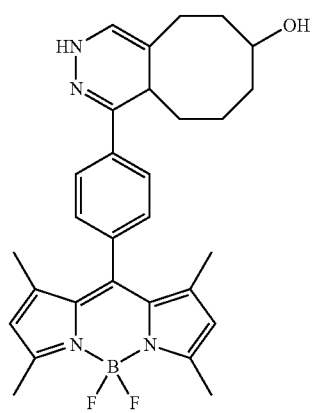

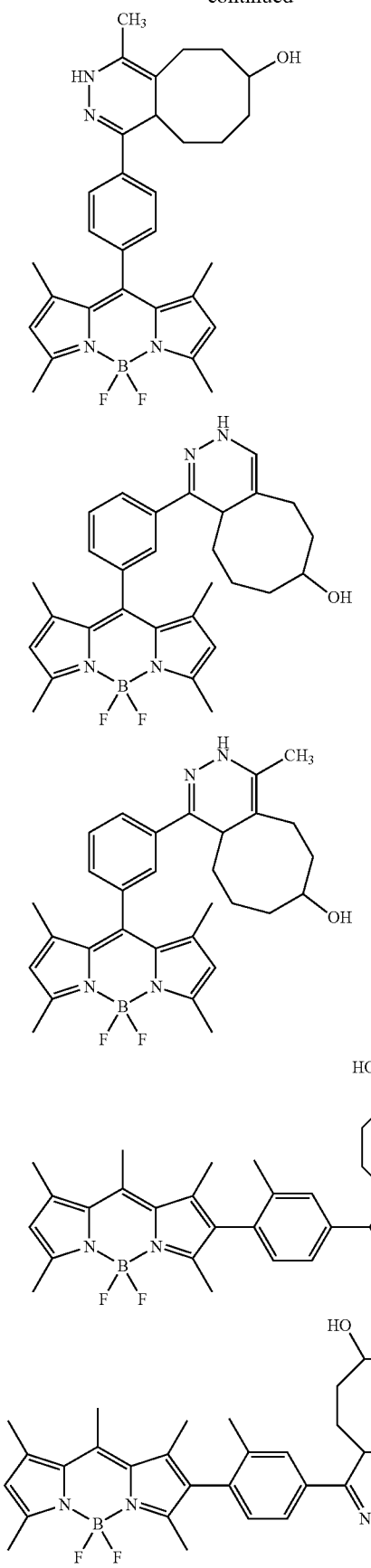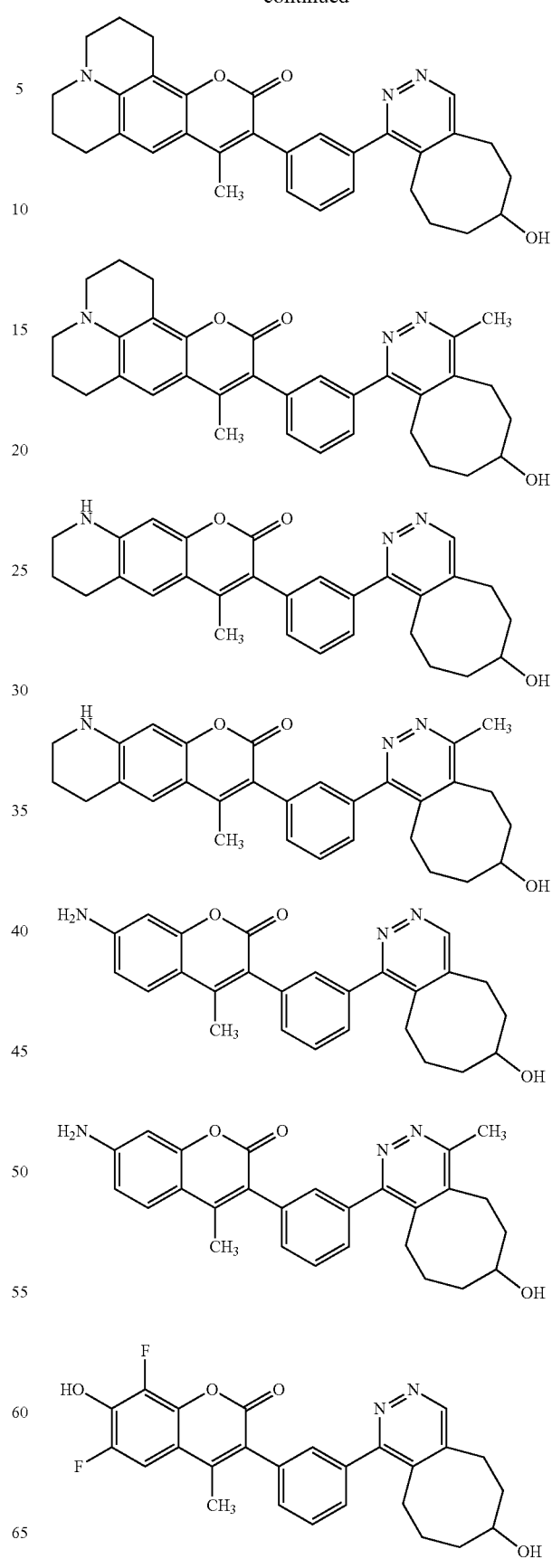

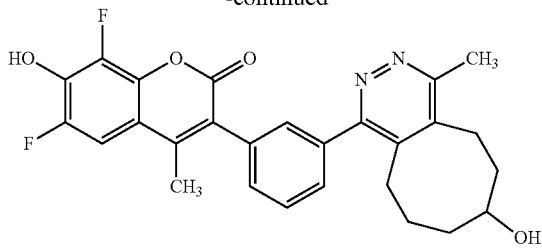

or a salt thereof.

Also provided herein is a compound of Formula (IV):

F-Z or a salt thereof, wherein F is a fluorophore and Z is a moiety comprising the reaction product of a diene and a dienophile, wherein the diene is a tetrazine or a derivative thereof as described previously, and wherein the Z and F moieties form a single conjugated pi-system.

The compounds provided herein can be referred to as Hyper Emissive Ligation-Initiated Orthogonal Sensing (HELIOS) probes. Many of the compounds provided herein are designated HELIOS XXX, where XXX refers to the absorption maximum of the "turned on" probe. This designation is used to refer to certain compounds within the present disclosure.

Synthesis

The compounds provided herein, including salts thereof, can be prepared using known organic synthesis techniques and can be synthesized according to any of numerous possible synthetic routes.

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in *Protecting Group Chemistry*, 1$^{st}$ Ed., Oxford University Press, 2000; March's Advanced Organic Chemistry: Reactions, Mechanisms, and Structure, 5$^{th}$ Ed., Wiley-Interscience Publication, 2001; and Peturssion, S. et al., "*Protecting Groups in Carbohydrate Chemistry,*" *J. Chem. Educ.*, 74(11), 1297 (1997).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" K. F. Blom, et al., *J Combi. Chem.* 6(6), 874 (2004) and normal phase silica chromatography.

In some embodiments, the compounds provided herein can be prepared as described in the Examples provided herein and as illustrated in Scheme 1.

Scheme 1.

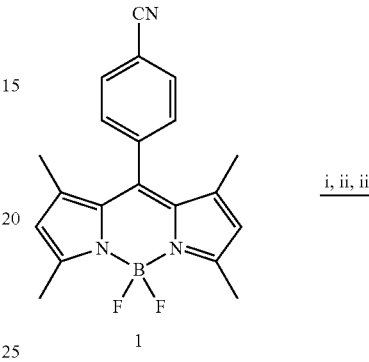

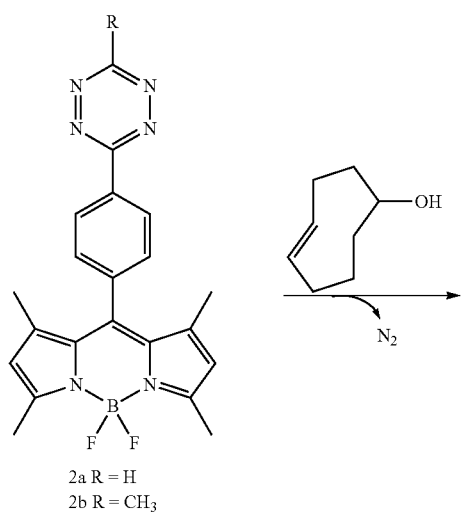

2a R = H
2b R = CH$_3$

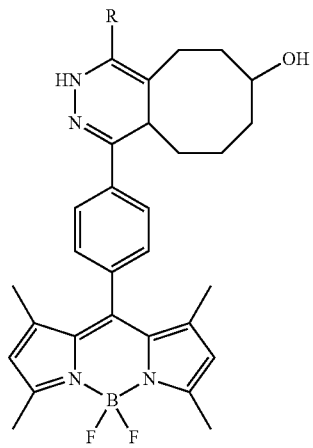

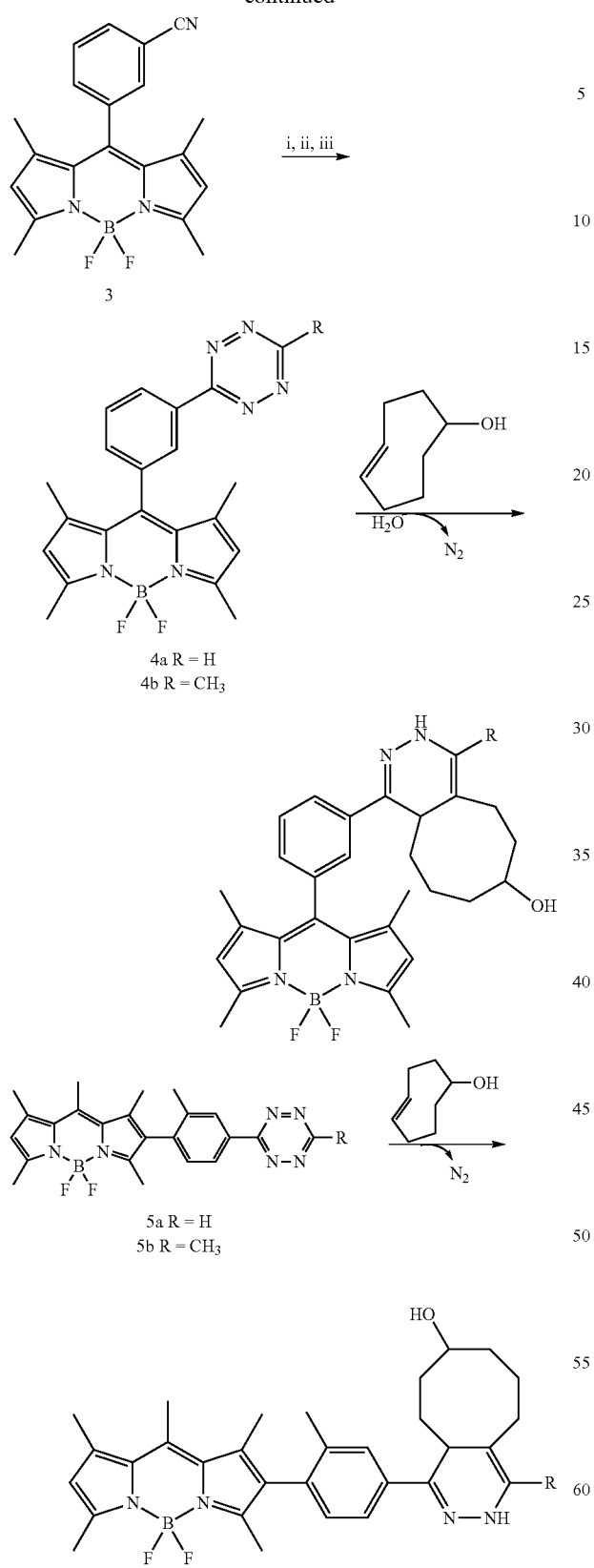
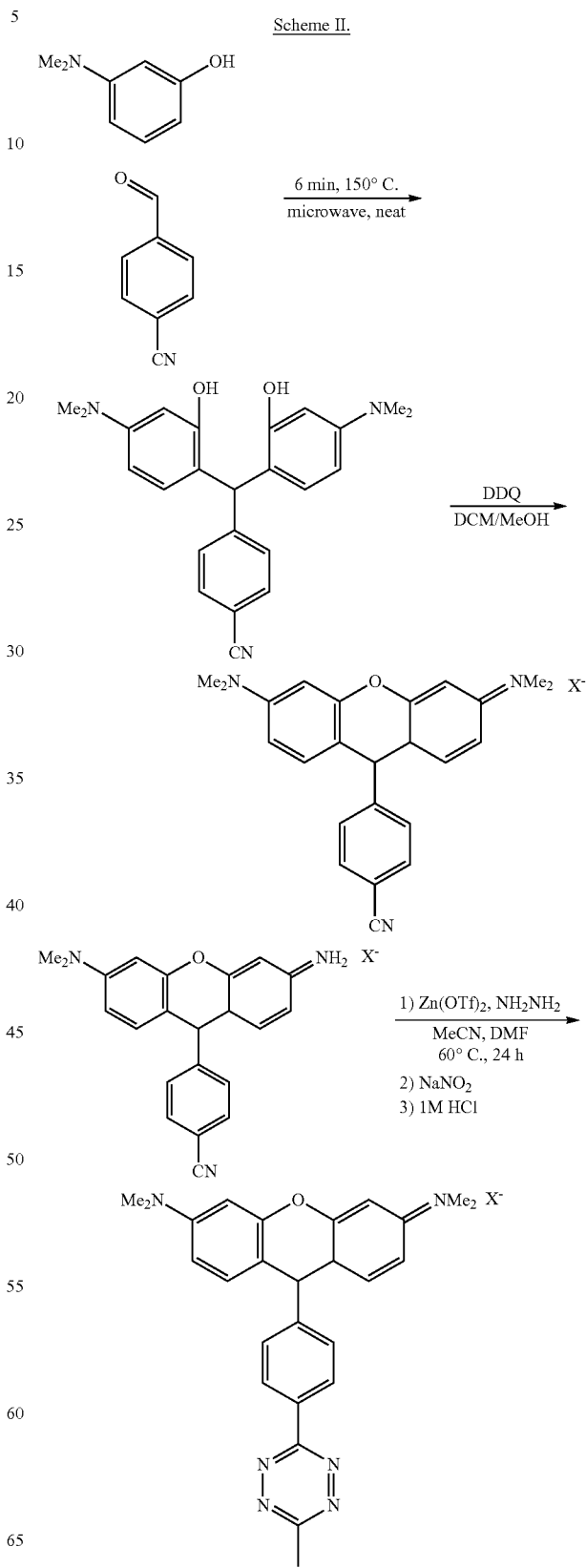
As another example, a compound as provided herein can also be prepared as illustrated in Scheme II.

45
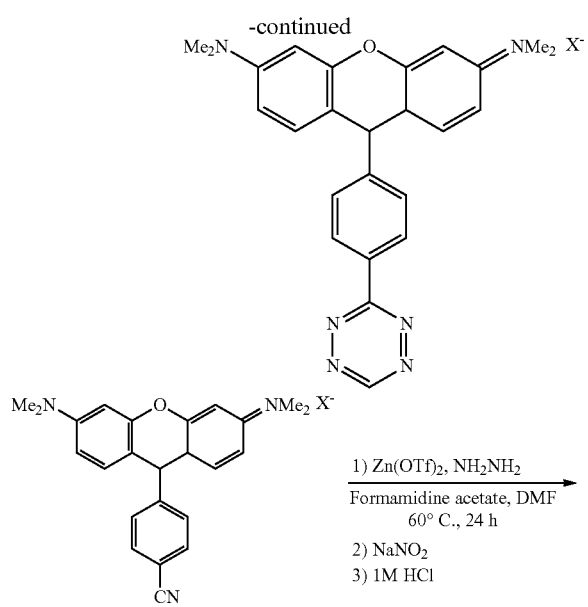
46
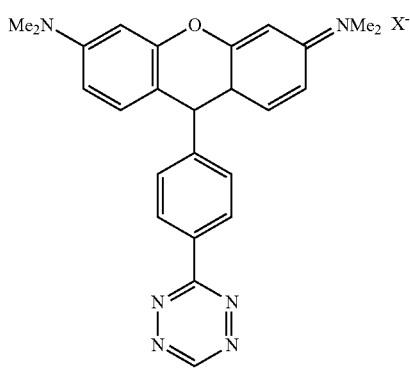
As another example, a compound as provided herein can also be prepared as illustrated in Scheme III.
Scheme III.
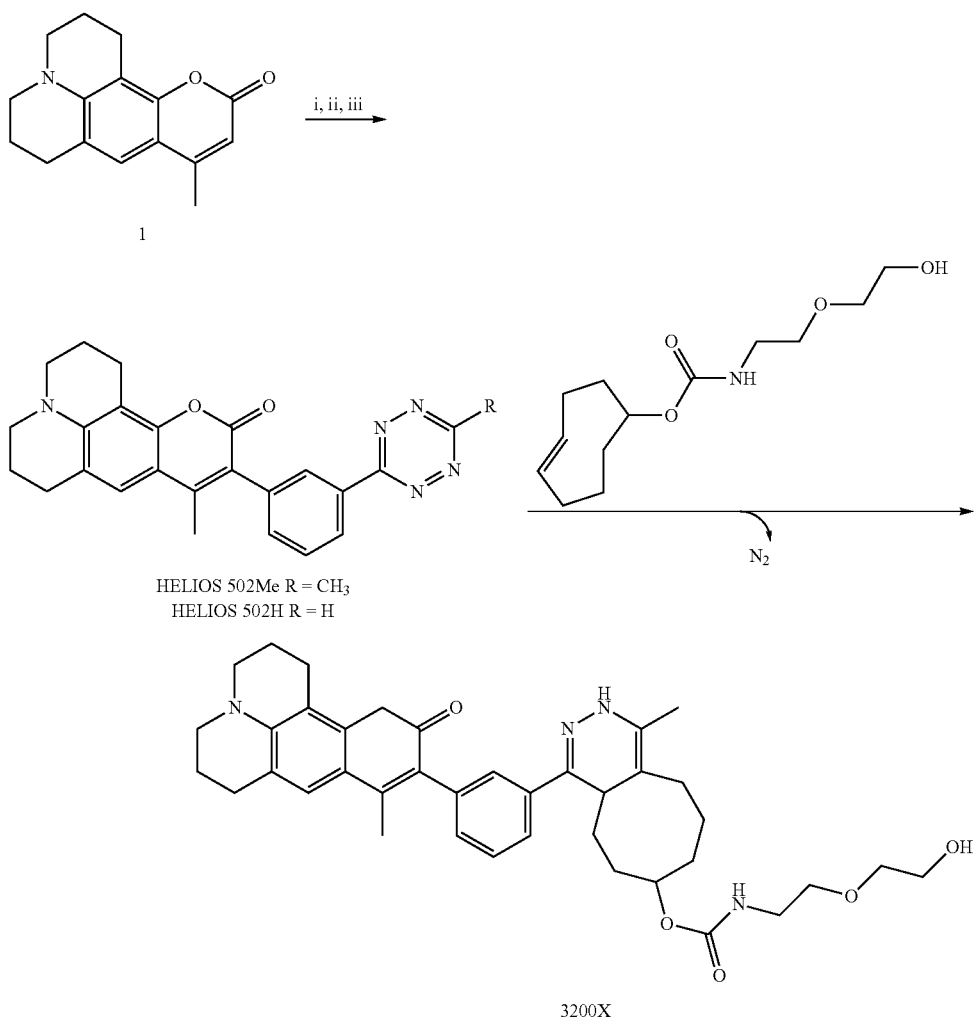

-continued
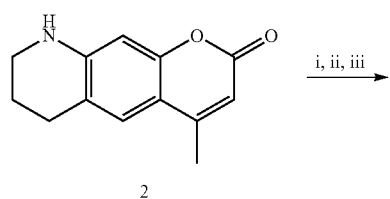
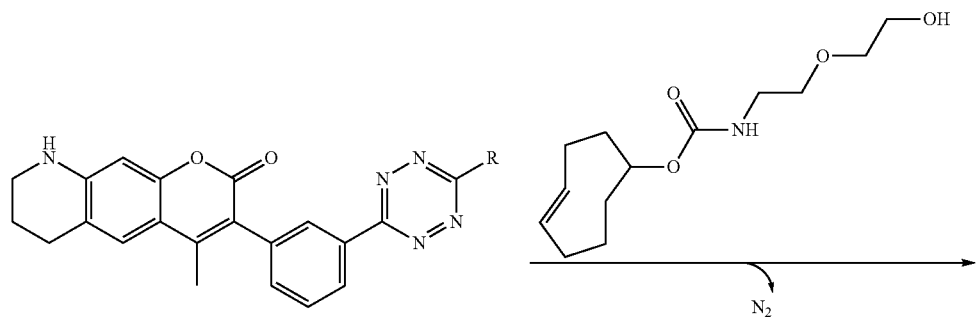
HELIOS 482Me R = CH₃
HELIOS 482H R = H
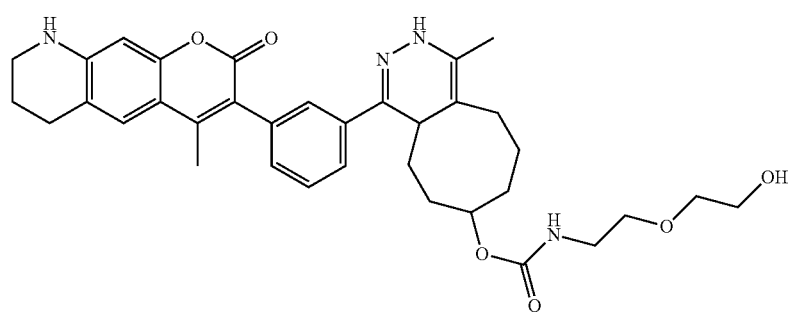
11000X
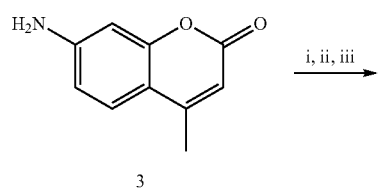
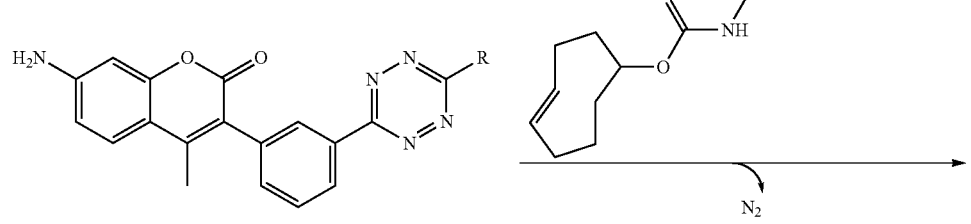
HELIOS 455Me R = CH₃
HELIOS 455H R = H

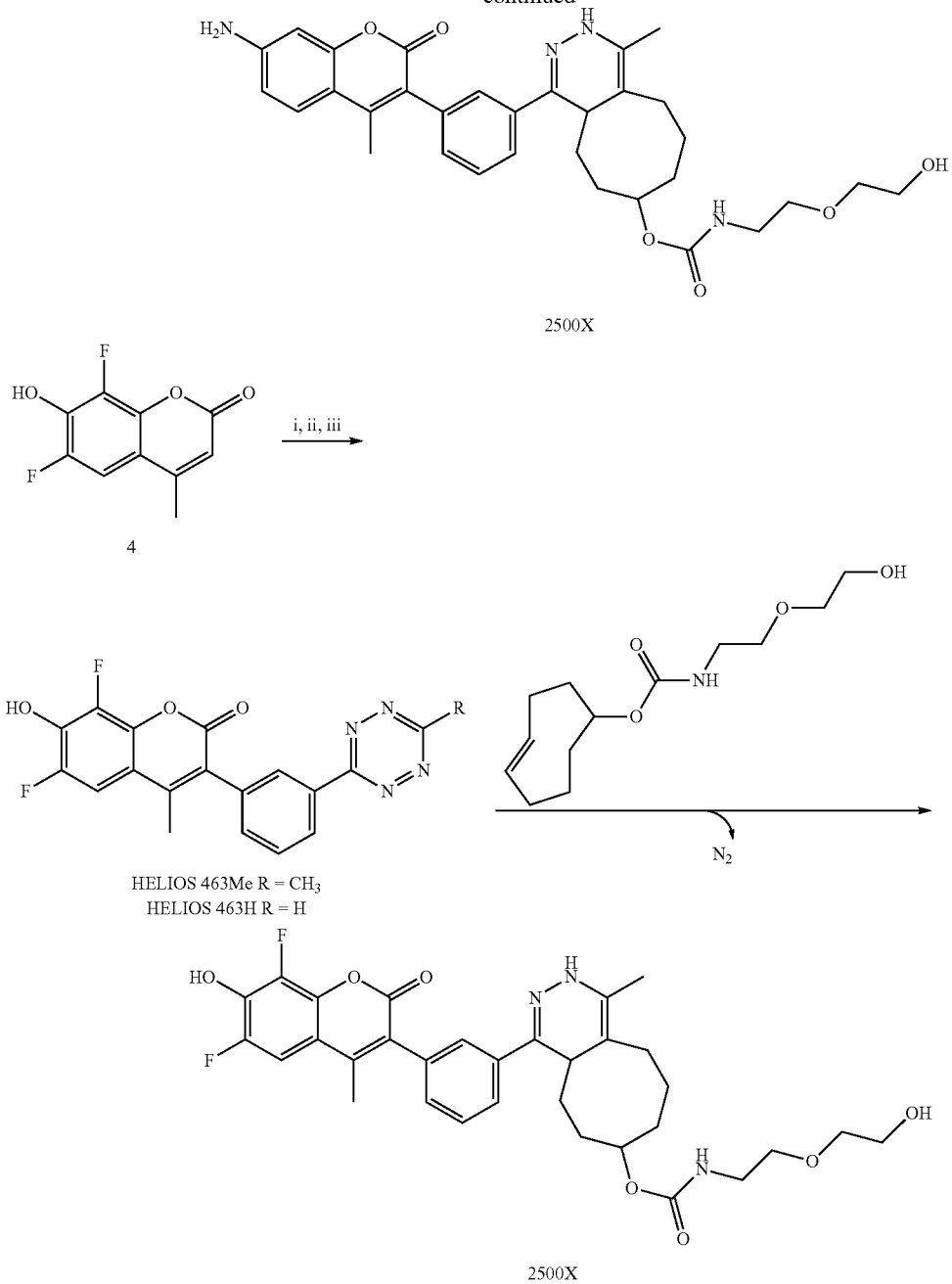

Reaction conditions: i) N-Bromosuccinimide in acetonitrile, ii) 3-cyanophenylboronic acid, Pd(OAc)$_2$(PPh$_3$)$_2$, K$_2$CO$_3$ in 75% dioxane(aq) at 100° C., iii) hydrazine, Zn(OTf)$_2$, acetonitrile/dioxane (Me-Tz) or formamidine hydrochloride/DMF (H-Tz) at 60° C. for 15 hours followed by NaNO$_2$ and HCl.

Pharmaceutical Compositions

Pharmaceutical compositions can include any of the compounds described herein, and can be formulated as a pharmaceutical composition in accordance with routine procedures. As used herein, pharmaceutical compositions can include pharmaceutically acceptable salts or derivatives thereof. "Pharmaceutically acceptable" means that the agent can be administered to an animal without unacceptable adverse effects. A "pharmaceutically acceptable salt or derivative" means any pharmaceutically acceptable salt, ester, salt of an ester, or other derivative of composition that, upon administration to a recipient, is capable of providing (directly or indirectly) a composition of the present disclosure. Other derivatives are those that increase the bioavailability when administered to a mammal (e.g., by allowing an orally administered compound to be more readily absorbed into the blood) or which enhance delivery of the parent compound to a biological compartment (e.g., the brain or lymphatic system) thereby increasing the exposure relative to the parent species. Pharmaceutically acceptable salts of the therapeutic or diagnostic compositions or compositions of this disclosure include counter ions derived from pharmaceutically acceptable inorganic and organic acids and bases known in the art, e.g., sodium, calcium, N-methylglutamine, lithium, magnesium, potassium, etc.

Pharmaceutical compositions can be administered by any route, including oral, intranasal, inhalation, or parenteral administration. Parenteral administration includes, but is not limited to, subcutaneous, intravenous, intraarterial, interstitial, intrathecal, and intracavity administration. When administration is intravenous, pharmaceutical compositions may be given as a bolus, as two or more doses separated in time, or as a constant or non-linear flow infusion. Thus, compositions can be formulated for any route of administration.

Typically, compositions for intravenous administration are solutions in sterile isotonic aqueous buffer. Where necessary, the composition may also include a solubilizing agent, a stabilizing agent, and a local anesthetic such as lidocaine to ease pain at the site of the injection. Generally, the ingredients will be supplied either separately, e.g. in a kit, or mixed together in a unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection," saline, or other suitable intravenous fluids. Where the composition is to be administered by injection, an ampule of sterile water for injection or saline may be provided so that the ingredients may be mixed prior to administration. Pharmaceutical compositions comprise the therapeutic or diagnostic compositions of the present disclosure and pharmaceutically acceptable salts thereof, with any pharmaceutically acceptable ingredient, excipient, carrier, adjuvant or vehicle.

A pharmaceutical composition is preferably administered to the subject in the form of an injectable composition. The method of administering a therapeutic or diagnostic composition is preferably parenterally, meaning intravenously, intra-arterially, intrathecally, interstitially or intracavitarilly. Pharmaceutical compositions can be administered to mammals including humans in a manner similar to other diagnostic or therapeutic agents. The dosage to be administered, and the mode of administration will depend on a variety of factors including age, weight, sex, condition of the subject and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 µg/kg, preferably between 0.01 to 25.0 µg/kg of host body mass. The optimal dose will be determined empirically following the disclosure herein.

Methods of Use

The compounds described herein can be imaged using methods known in the art. For example, a compound provided herein can be detected by traditional fluorescence imaging techniques allowing for the facile tracking of the compounds by fluorescence microscopy or flow cytometry using methods known in the art, e.g., as described in US 2005/0249668.

The compositions and methods described herein can be imaged using a variety of modalities that are known to one of skill in the art. Detection methods can include both imaging ex vivo and in vivo imaging methods, e.g., fluorescence reflectance imaging, fluorescence microscopy, super-resolution microscopy (see, e.g., M. Bates et al., *Science* 2007, 317: 1749; and G. Patterson et al., *Annu. Rev. Phys. Chem.* 2010, 61: 345), and fluorescence molecular tomographic imaging. In some embodiments, one or more imaging techniques can be used in the methods provided herein.

After a compound has been designed, synthesized, and optionally formulated, it can be tested in vitro by one skilled in the art to assess its biological and performance characteristics. For instance, different types of cells grown in culture can be used to assess the biological and performance characteristics of the compound. Cellular uptake, binding or cellular localization of the agent can be assessed using techniques known in the art, including, for example, fluorescent microscopy and fluorescence-activated cell sorting (FACS) analysis.

By way of example, the compound can be contacted with a sample for a period of time. The sample can then be viewed using an appropriate detection device without the need for washing or clearance steps. A detection device can include a fluorescent microscope equipped with appropriate filters matched to the optical properties of a fluorescent agent. Fluorescence microscopy of cells in culture is also a convenient means for determining whether uptake and binding has occurred. Tissues, tissue sections and other types of samples can also be used in a similar manner to assess the biological and performance characteristics of the compounds.

Formation of a compound of Formula (III) can occur through the reaction of a compound of Formula (I) with the corresponding dienophile. Similarly, the formation of a compound of Formula (IV) can occur through the reaction of a compound of Formula (II) with the corresponding dienophile.

In some embodiments, a compound of Formula (I) or (II) exhibits low or no fluorescence prior to activation upon reaction with a dienophile. For example, the turn-on ratio of a compound of Formula (III) or (IV) (i.e., the reaction product of the corresponding compound of Formula (I) or (II) with the corresponding dienophile) can be greater than 50 (e.g., greater than 60, greater than 75, greater than 100, greater than 125, greater than 150, greater than 200, greater than 300, greater than 400, greater than 500, greater than 600, greater than 700, greater than 800, greater than 900, greater than 1000, greater than 1500, greater than 2000, greater than 2500, greater than 3000, greater than 3500, greater than 4000, greater than 4500, greater than 5000, greater than 5500, greater than 6000, greater than 6500, greater than 7000, greater than 7500, greater than 8000, greater than 8500, greater than 9000, greater than 9500, greater than 10,000, greater than 11,000, greater than 12,000, greater than 14,000, greater than 15,000, greater than 16,000, greater than 18,000, greater than 20,000, greater than 22,000, greater than 24,000, greater than 26,000, greater than 28,000, greater than 30,000). In some embodiments, the turn-on ratio of a compound of Formula (III) or (IV) can range from about 100 to about 2000 (e.g., from about 100 to about 1800; from about 100 to about 1600; from about 100 to about 1250; from about 100 to about 1000; from about 100 to about 800; from about 100 to about 750; from about 100 to about 500; from about 100 to about 400; from about 100 to about 300; from about 200 to about 2000; from about 400 to about 2000; from about 600 to about 2000; from about 800 to about 2000; from about 1000 to about 2000; from about 1200 to about 2000; from about 1500 to about 2000; from about 200 to about 1800; from about 400 to about 1600; from about 500 to about 1500; and from about 750 to about 1250). In some embodiments, the turn-on ratio of a compound of Formula (III) or (IV) can range from about 1000 to about 30,000 (e.g., from about from about 1000 to about 25,000; from about 1000, to about 22,000; from about 1000 to about 18,000; from about 1000 to about 16,000; from about 1000 to about 12,500; from about 1000 to about 10,000; from about 1000 to about 8,000; from about 1000 to about 7,500; from about 1000 to about 5000; from about 1000 to about 4000; from about 1000 to about 3000; from about 2000 to about 30,000; from about 4000 to about 30,000; from about 6000 to about 30,000; from about 8000 to about 30,000; from about 10,000 to about 30,000; from about 12,000 to about 30,000; from about 15,000 to about 30,000; from about 20,000 to about 30,000; from about 2000 to about 12,000; from about 4,000 to about 16,000; from about 2500 to about 17,500; from about from about 10,000 to about 20,000; from about 5000 to about 15,000; and from about 7,500 to about 12,500). Such low or no fluorescence prior to activation can lead to a background signal which is zero or very near the detection limit of the fluorescence instrument.

The bioorthogonal inverse electron demand Diels-Alder reaction can be tailored to provide a straightforward method for the rapid, specific covalent labeling and imaging with ligands such as small molecules and other biomolecules inside living cells. Despite numerous developments in the application of various selective chemistries to extracellular live cell labeling, to date, no method has been universally adapted to intracellular labeling. For example, described herein are a series of "turn-on" tetrazine-linked fluorescent probes that react rapidly via an inverse electron demand Diels-Alder reaction to strained dienophiles such as trans-cyclooctene. Upon cycloaddition, the fluorescence intensity increases dramatically, in some cases by ~20 fold. This fluorescence "turn-on" significantly lowers background signal. These novel probes for live cell imaging of a ligand such as an antibody, small molecule, or other biomolecule modified with a strained alkene can provide a general method for labeling and imaging a ligand bound to a specific target. For example, this bioorthogonal inverse electron demand Diels-Alder reaction can be applied to an asymmetric tetrazine and a strained alkene, which is physically coupled to a small molecule, i.e. a trans-cyclooctene modified taxol analog and can be used to label and image this small molecule bound to intracellular tubules. The rapid reaction rate coupled with fluorescence "turn-on" makes this a nearly ideal method for revealing small molecules inside living cells.

In some embodiments, the ligand, e.g., an antibody, small molecule therapeutic agent (e.g., a drug), nanoparticles, polymers, or other biomolecule, is physically attached (conjugated) to the dienophile. In some embodiments, the ligand carries a functional group such as an amine, alcohol, carboxylic acid or ester, or other group of atoms on the ligand that can undergo a chemical reaction allowing attachment to the dienophile. Alternatively or in addition, the dienophile possesses a reactive functional group for attachment to the ligand. Thus, the reactive functional group on the ligand and/or dienophile undergoes a chemical reaction to form a link between the two. In some embodiments, e.g., where the ligand is a biopolymer such as a nucleic acid, peptide, or polypeptide, the functional group on the ligand can be a non-natural nucleoside or amino acid, e.g., as described in Xie and Schultz, *Nat. Rev. Mol. Cell Biol.* 7:775-782 (2006); for example, the diene or dienophile can be incorporated into a non-natural amino acid as the side chain. One of skill in the art could readily synthesize such compounds. For example, a compound as provided herein can be modified to include a reactive moiety (A):

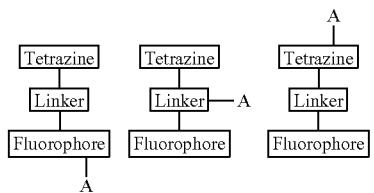

Non-limiting examples of the reactive moiety (A) include a reactive ester (e.g., NHS ester), a primary amine, carboxylic acid, azide, alkyne, a second tetrazine, maleimide, and thiol. The reactive moiety can be used to couple the compound to additional groups, including small molecules (e.g., drugs and therapeutic agents) and nanoparticles. In the case of a small molecule drug, the fluorescent compounds provided herein could be used to monitor delivery of the drug following administration.

In some embodiments, a compound as provided herein is imaged in vivo using fluorescent imaging. For example, the use of such methods permits the facile, real-time imaging and localization of cells or tissues labeled with a compound provided herein. In some embodiments, a compound provided herein is imaged in vivo using laparoscopy and/or endomiscroscopy. For example, the use of laparoscopy permits the facile, real-time imaging and localization of cells or tissues labeled with a compound provided herein. In some embodiments, a compound can be imaged using fiber optic endomicroscopy.

A number of preclinical and clinical applications for a compound provided herein can be envisioned. For example, a compound described here can be used: 1) for the early detection cancers; 2) as an aid to surgeons during surgery (e.g., by allowing for real-time detection of cancer cells); and 3) as a method for monitoring the progress of a cancer treatment (e.g., by quantifying the cancer cells present before, during, and after treatment).

For example, the compounds provided herein can be administered to a subject in combination with surgical methods, for example, resection of tumors. The compounds can be administered to the individual prior to, during, or after surgery. The compounds can be administered parenterally, intravenous or injected into the tumor or surrounding area after tumor removal, e.g., to image or detect residual cancer cells. For example, the compound may be used to detect the presence of a tumor and to guide surgical resection. In some embodiments, the compound can be used to detect the presence of residual cancer cells and to guide continued surgical treatment until at least a portion (e.g., all) such cells are removed from the subject. Accordingly, there is provided a method of guided surgery to remove at least a portion of a tumor from a subject comprising providing a compound provided herein; causing the compound to be present in at least some cancer cells; observing the image following activation of the compound (e.g., fluorescence); and performing surgery on the subject to remove at least a portion of the tumor that comprises detected cancer cells.

With respect to in vitro imaging methods, the compounds and compositions described herein can be used in a variety of in vitro assays. An exemplary in vitro imaging method comprises: contacting a sample, for example, a biological sample (e.g., a cell), with one or more compounds provided herein; allowing the compound to interact with a biological target in the sample; illuminating the sample with light of a wavelength absorbable by a fluorophore of the agents; and detecting a signal emitted from fluorophore thereby to determine whether the agent has been activated by or bound to the biological target. In some embodiments, the compounds provided herein may be used without requiring clearance of unbound fluorophore prior to imaging.

EXAMPLES

The invention is further described in the following examples, which do not limit the scope of the invention described in the claims.

General Methods

Materials and Methods

All reagents were purchased from Sigma-Aldrich and used without further purification unless otherwise noted. Proton and carbon nuclear magnetic resonance ($^1$H & $^{13}$C NMR) spectra were recorded on either a Varian AS-400 (400 MHz) spectrometer or a Varian 500 MHz spectrometer. Silica Gel 60 (40-63 μm) was used for purification. High performance liquid chromatography-mass spectrometry analysis (HPLC-MS) was performed with on a Waters instrument equipped with a Waters 2424 ELS Detector, Waters 2998 UV-Vis Diode array Detector, Waters 2475 Multi-wavelength Fluorescence Detector, and a Waters 3100 Mass Detector. Separations employed Waters XTerra RP Cis 5 μm or Waters Atlantis RP 5 μm columns, with a water:acetonitrile solvent gradient (0.1% formic acid added). Fluorescence measurements were conducted with a Perkin Elmer LS50B Luminescence Spectrometer, and UV-VIS absorption spectra on an Agilent Technologies Cary 100 UV-Vis Spectrophotometer.

Fluorescence Assays

Figure 2:
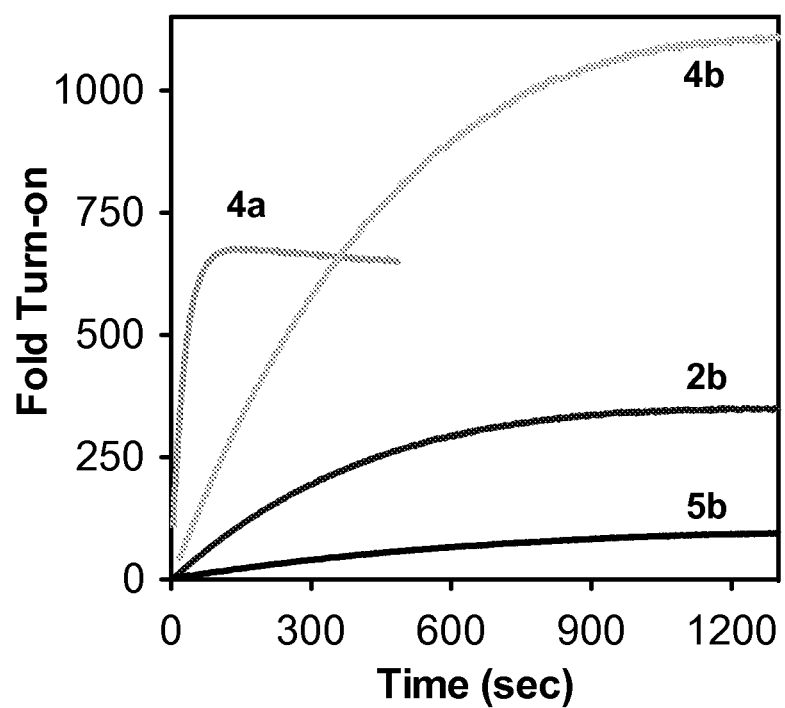
FIG. 2 illustrates normalized fluorescence turn-on after addition of TCO (240 µM) to a solution of the indicated fluorophore (1 µM) in acetonitrile; initial intensity 1.0 a.u.
Figure 3:
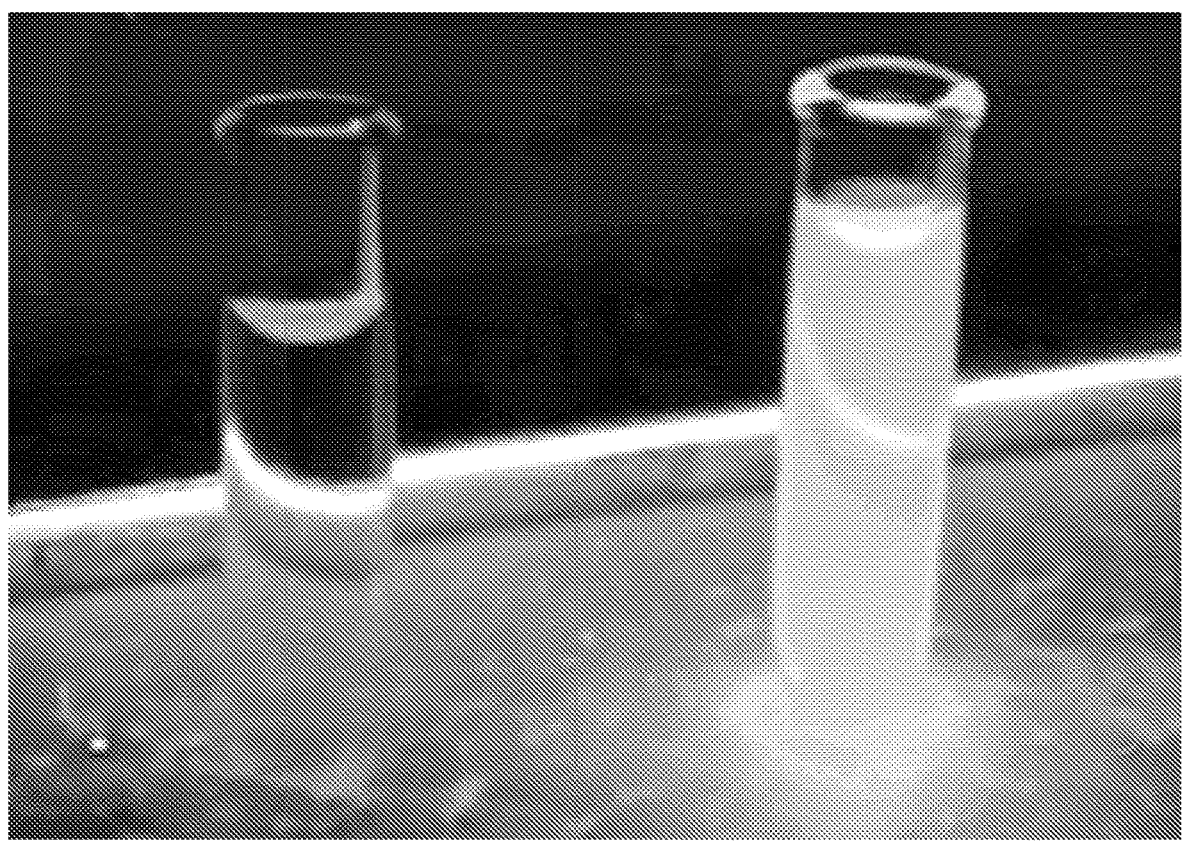
FIG. 3 is a photograph showing equimolar solutions of compound 2a (at left) and 2a plus TCO (at right) under excitation by a handheld UV lamp.
Figure 4:
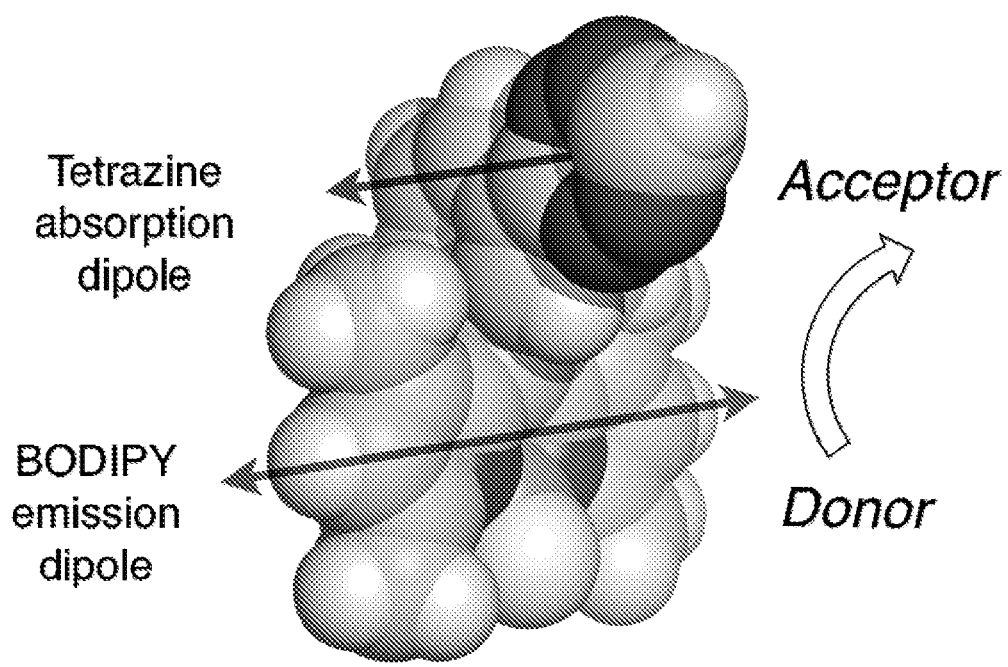
FIG. 4 is a 3D model of compound 4a, illustrating a twisted phenyl linker between the BODIPY and Tz chromophores and the orientation of the donor and acceptor transition dipoles (gray arrows).

The purity of all compounds was verified by LCMS prior to quantitative activation experiments and a fresh aliquot of the fluorophore collected from the analytical HPLC elution. Stock solutions in acetonitrile were diluted into 2 mL or 3 mL of the appropriate solvent in a 1 cm×1 cm quartz cuvette. Measurements of solvent and pre-activation emission spectra for baseline values were made in at least triplicate, prior to addition of transcyclooctenol (TCO) to initiate the fluorogenic reaction. Activation ratios were calculated from the peak emission intensity of the reacted dihydropyridazine product and the corresponding baseline intensity. Integration of the area under the emission intensity curves was used to validate the activation ratios. For the time-course experiments (FIG. 2), the normalized baseline was calculated from the mean emission intensity during 30-60 seconds of observation of the solvent blank followed by the pre-TCO fluorophore solution. After addition of TCO, the fluorescence emission intensity was monitored until a plateau was reached. The rate of activation of 5b was attenuated relative to the other methyltetrazines (2b,4b); a 2.5-fold additional excess of TCO was added for facile comparison of the magnitude of fluorescence turn on.

For quantum yield determinations, fluorescein in 0.1M NaOH was used as a reference, with an excitation wavelength of 470 or 480 nm (ex slit 2.5 nm); a value of 0.925 was assigned to the quantum yield of fluorescein (Magde, D., Wong, R., & Seybold, P. G. *Photochemistry and Photobiology*, 2002, 75(4), 327-334), and calculations made according to the methods described by Crosby and Demas (*Chemical Reviews*, 1971, 75(8), 991-1024).

Example 1—Preparation of Compounds 2a and 2b

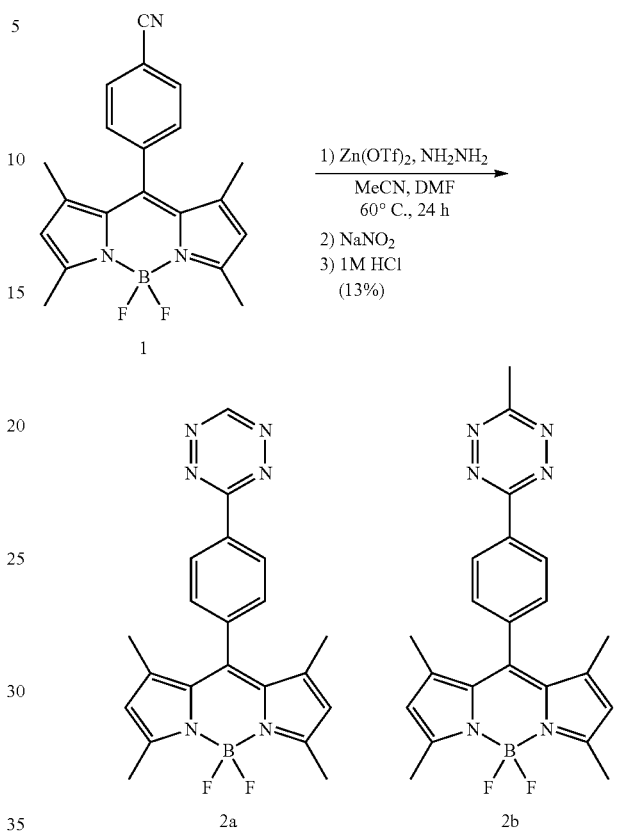

To p-cyanophenyl-BODIPY 1 (100 mg, 0.28 mmol) in a microwave reaction tube under a stream of argon was added Zn(OTf)$_2$ (52.3 mg, 0.14 mmol), MeCN (0.16 mL, 3.0 mmol), DMF (0.34 mL) and NH$_2$NH$_2$ (0.55 mL, 16.0 mmol). The vessel was sealed and allowed to stir at 60° C. for 24 hours after which it was allowed to cool and the septum removed. To the reaction mixture was added NaNO$_2$ (300 mg, 4.34 mmol) in 10 mL of water followed by 1 M HCl until the pH=3. The aqueous phase was extracted three times with CH$_2$Cl$_2$ (100 mL). The combined organic extracts were dried with MgSO$_4$ and concentrated using a rotary evaporator. The crude mixture was purified using flash column chromatography (toluene:hexane gradient 3:1, 4:1, 100% toluene) to give 2a and 2b. Compounds 2a and 2b were further purified using flash column chromatography (hexanes:ethyl acetate gradient 6:1, 4:1) to give H-tetrazine 2a (6.2 mg, 0.015 mmol, 5.5%) and Me-tetrazine 2b (9.5 mg, 0.022 mmol, 8.1%) as dark red solids. In sharp contrast to the parent compound 1, both 2a and 2b are modestly soluble in aqueous solution and almost completely non-fluorescent.

Compound 2a: $^1$H NMR (400 MHz, CD$_2$Cl$_2$) δ 10.29 (s, 1H), 8.80 (d, J=8.4 Hz, 2H), 7.64 (d, J=8.0 Hz, 2H), 6.07 (s, 2H), 2.55 (s, 6H), 1.50 (s, 6H); $^{13}$C NMR (100 MHz, CD$_2$Cl$_2$) δ 166.1, 158.1, 155.9, 143.1, 140.3, 139.8, 132.6, 130.8, 129.4, 128.9, 121.4, 14.4 (4C). ESIMS [M+H]+ calcd for C$_{21}$H$_{20}$BF$_2$N$_6$ 405.18. found 405.23.

Compound 2b: $^1$H NMR (400 MHz, CD2Cl2) δ 8.76 (d, J=8.8 Hz, 2H), 7.61 (d, J=8.8 Hz, 2H), 6.10 (s, 2H), 3.11 (s, 3H), 2.54 (s, 6H), 1.50 (s, 6H); $^{13}$C NMR (100 MHz, CD2Cl2) δ 167.7, 163.7, 155.9, 143.2, 140.5, 139.1, 132.8, 130.9, 129.2, 128.5, 121.4, 21.0, 14.3 (4C). ESIMS [M+H]+ calcd for $C_{22}H_{22}BF_2N_6$ 419.20. found 419.29.

Example 2—Preparation of Compound 3

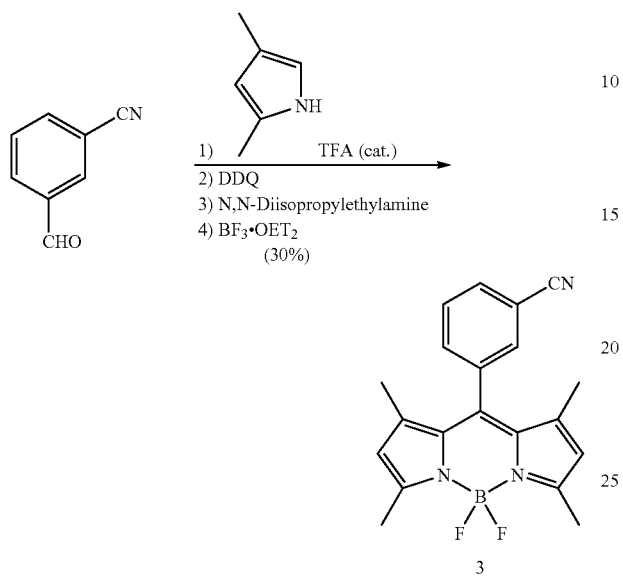

To 3-formylbenzonitrile (1.0 g, 7.6 mmol) and 2,4-dimethylpyrrole (1.7 mL, 16.5 mmol) in 200 mL of $CH_2Cl_2$ under argon atmosphere was added four drops of TFA and allowed to stir at room temperature. After 30 minutes thin layer chromatography showed the disappearance of 3-formylbenzonitrile after which 2,3-dichloro-5,6-dicyano-1,4-benzoquinone (DDQ) (1.73 g, 7.6 mmol) in $CH_2Cl_2$ (200 mL) was added followed by N,N-diisopropylethylamine (15.5 mL, 88.9 mmol) and $BF_3$·$OEt_2$ (15.5 mL, ~45% $BF_3$ content). The reaction was allowed to stir overnight after which water (100 mL) was added and the aqueous phase was extracted three times with $CH_2Cl_2$ (300 mL). The combined organic extracts were dried with $MgSO_4$ and concentrated using a rotary evaporator. The crude mixture was purified using flash column chromatography (toluene:hexane gradient 3:1, 100% toluene) to give 3 (822.7 mg, 2.3 mmol, 30.2%) as a red solid. $^1H$ NMR (500 MHz, $(CD_3)_2SO$) δ 8.04 (m, 1H), 7.98 (m, 1H), 7.75 (m, 2H), 6.19 (s, 2H), 2.45 (s, 6H), 1.32 (s, 6H)); $^{13}C$ NMR (125 MHz, (CD3)2SO) δ 155.9, 144.5, 143.0, 139.5, 135.6, 133.7, 133.5, 132.2, 131.0, 122.2, 121.1, 112.9, 14.7 (4C). ESIMS [M+H]+ calcd for $C_{20}H_{19}BF_2N_3$ 350.16. found 350.22.

Example 3—Preparation of Compounds 4a and 4b

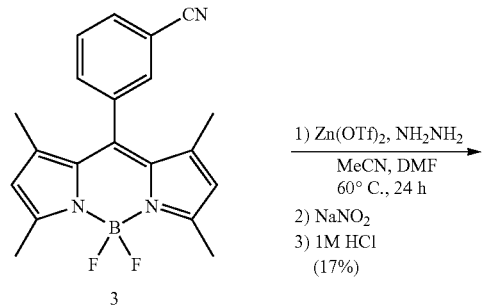

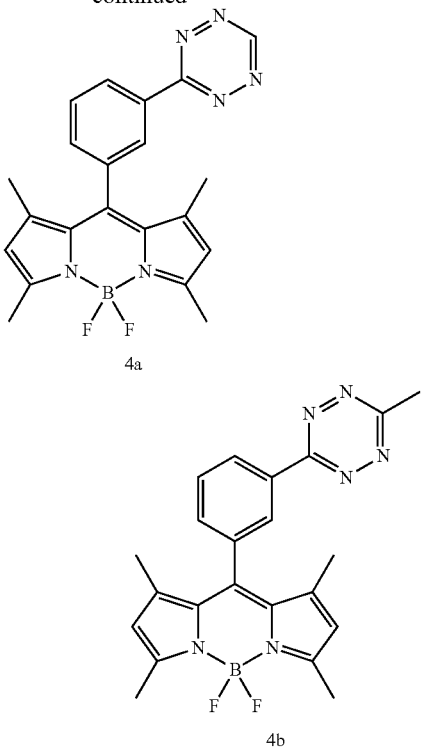

To 3 (100 mg, 0.28 mmol) in a microwave reaction tube under a stream of argon was added $Zn(OTf)_2$ (52.3 mg, 0.14 mmol), MeCN (0.16 mL, 3.0 mmol), DMF (0.34 mL) and $NH_2NH_2$ (0.55 mL, 16.0 mmol). The vessel was sealed and allowed to stir at 60° C. for 24 hours after which it was allowed to cool and the septum removed. To the reaction mixture was added $NaNO_2$ (300 mg, 4.34 mmol) in 10 mL of water followed by 1 M HCl until the pH=3. The aqueous phase was extracted three times with $CH_2Cl_2$ (100 mL). The combined organic extracts were dried with MgSO4 and concentrated using a rotary evaporator. The crude mixture was purified using flash column chromatography (toluene: acetonitrile gradient 100% toluene, 100:0.5) to give 4a and 4b as dark orange solids. Compounds 4a and 4b were further purified using flash column chromatography (hexanes:ethyl acetate 4:1) to give H-tetrazine 4a (9.6 mg, 0.023 mmol, 8.4%) and Metetrazine 4b (10.1 mg, 0.024 mmol, 8.6%) as dark red solids.

Compound 4a: $^1H$ NMR (500 MHz, $(CD_3)_2SO$) δ 10.63 (s, 1H), 8.67 (d, J=8.0 Hz, 11H), 8.40 (s, 1H), 7.89 (t, J=8.0 Hz, 1H), 7.78 (d, J=8.0 Hz, 1H), 6.21 (s, 2H), 2.47 (s, 6H), 1.41 (s, 6H); $^{13}C$ NMR (125 MHz, $(CD_3)_2SO$) δ 165.6, 158.7, 155.8, 143.1, 140.9, 135.5, 133.6, 132.7, 131.1, 131.0, 129.0, 127.6, 122.1, 14.8 (4C). ESIMS [M+H]+ calcd for $C_{21}H_{20}BF_2N_6$ 405.18. found 405.27.

Compound 4b: $^1H$ NMR (500 MHz, $(CD_3)_2SO$) δ 8.64 (dt, J=8.0, 1.5 Hz, 1H), 8.37 (t, J=2.0 Hz, 1H), 7.87, (J=7.5 Hz, 1H), 7.75 (dt, J=7.5, 1.5 Hz, 1H), 6.21 (s, 2H), 3.00 (s, 3H), 2.47 (s, 6H), 1.40 (s, 6H); $^{13}C$ NMR (125 MHz, $(CD_3)_2SO$) δ 167.8, 163.4, 155.8, 143.0, 140.9, 135.5, 133.6, 132.3, 132.2, 132.0, 129.1, 127.2, 122.1, 21.3, 14.8 (4C). ESIMS [M+H]+ calcd for $C_{22}H_{22}BF_2N_6$ 419.20. found 419.27.

Example 4—Preparation of Compound 6

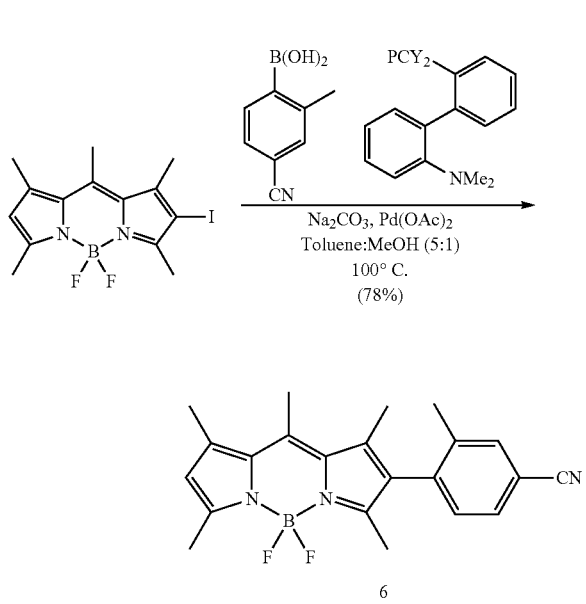

To 2-iodo-pentamethyl BODIPY (800 mg, 2.06 mmol) dissolved in 60 mL of toluene:methanol (5:1) under argon atmosphere was added Na$_2$CO$_3$ (874 mg, 824 mmol), Pd(OAc)$_2$ (46.2 mg, 0.20 mmol), 2-methyl-4-cyanophenylboronicacid (994.8 mg, 6.2 mmol) and 2-dicyclohexylphosphino-2'-(N,N-dimethylamino)biphenyl (121.6 mg, 0.31 mmol). The mixture was heated to 100° C. and stirred. After 2.5 hours, thin layer chromatography showed the disappearance of 2-iodo-pentamethyl BODIPY and the reaction was diluted with 100 mL of water. The aqueous phase was extracted three times with toluene (300 mL). The combined organic extracts were dried with MgSO$_4$ and concentrated using a rotary evaporator. The crude mixture was purified using flash column chromatography (toluene) to give 6 (606.3 mg, 1.6 mmol, 77.7%) as a red solid.

$^1$H NMR (400 MHz, CD$_2$Cl$_2$) δ 7.34 (s, 1H), 7.57 (d, J=7.6 Hz, 1H), 7.25 (d, J=7.6 Hz, 1H), 6.17 (s, 1H), 2.67 (s, 3H), 2.52 (s, 3H), 2.48 (s, 3H), 2.28 (s, 3H), 2.19 (s, 3H), 2.18 (s, 3H); $^{13}$C NMR (100 MHz, CD$_2$Cl$_2$) δ 154.9, 150.2, 142.5, 142.4, 139.6, 138.9, 137.1, 133.5, 132.6, 131.9, 131.6, 130.8, 129.4, 121.8, 118.9, 111.5, 19.4, 17.2, 16.7, 15.0, 14.2, 12.7. ESIMS [M+H]+ calcd for C$_{22}$H$_{23}$BF$_2$N$_3$ 378.20. found 378.27.

Example 5—Preparation of Compounds 5a and 5b

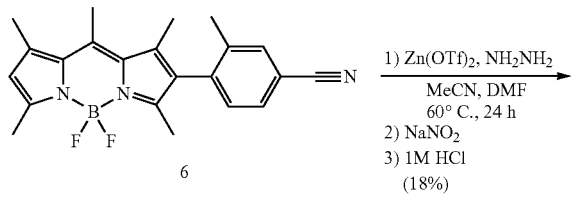

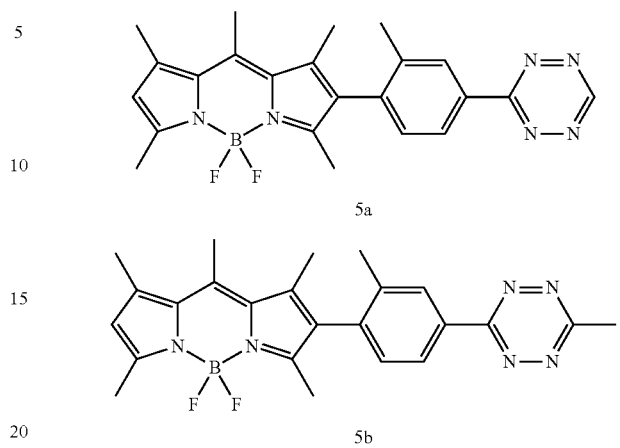

To 6 (100 mg, 0.26 mmol) in a microwave reaction tube under a stream of argon was added Zn(OTf)$_2$ (49.5 mg, 0.13 mmol), MeCN (0.15 mL, 2.8 mmol), DMF (0.32 mL) and NH$_2$NH$_2$ (0.52 mL, 15.1 mmol). The vessel was sealed and allowed to stir at 60° C. for 24 hours after which it was allowed to cool and the septum removed. To the reaction mixture was added NaNO$_2$ (283.8 mg, 4.1 mmol) in 10 mL of water followed by 1 M HCl until the pH=3. The aqueous phase was extracted three times with CH$_2$Cl$_2$ (100 mL). The combined organic extracts were dried with MgSO$_4$ and concentrated using a rotary evaporator. The crude mixture was purified using flash column chromatography (toluene: acetonitrile gradient 100% toluene, 100:0.2) to give 5a and 5b. Compounds 5a and 5b were further purified using flash column chromatography (hexanes:ethyl acetate 4:1) to give H-tetrazine 5a (8.9 mg, 0.023 mmol, 8.0%) and Me-tetrazine 5b (11.6 mg, 0.026 mmol, 10.0%) as dark red solids.

Compound 5a: $^1$H NMR (500 MHz, CD$_2$Cl$_2$) δ 10.20 (s, 1H), 8.61 (s, 1H), 8.51 (dd, J=8.0, 2.0 Hz, 1H), 7.40 (d, J=8.0 Hz, 1H), 6.17 (s, 1H), 2.71 (s, 3H), 2.54 (s, 3H), 2.49 (s, 3H), 2.36 (s, 3H), 2.30 (s, 3H), 2.27 (s, 3H); $^{13}$C NMR (125 MHz, CD$_2$Cl$_2$) δ 166.5, 157.9, 154.4, 150.9, 142.3, 142.1, 139.5, 138.9, 137.5, 132.5, 132.2, 131.8, 131.7, 131.2, 129.6, 125.5, 121.6, 19.8, 17.2, 16.7, 15.2, 14.2, 12.8. ESIMS [M+H]+ calcd for C$_{23}$H$_{24}$BF$_2$N$_6$ 433.2. found 433.26.

Compound 5b: $^1$H NMR (400 MHz, CDCl$_3$) δ 8.54 (s, 1H), 8.46 (dd, J=7.6, 1.6 Hz, 1H), 7.33 (d, J=8.4 Hz, 1H), 6.11 (s, 1H), 3.12 (s, 3H), 2.67 (s, 3H), 2.56 (s, 3H), 2.46 (s, 3H), 2.38 (s, 3H), 2.26 (s, 3H), 2.23 (s, 3H); $^{13}$C NMR (100 MHz, CDCl$_3$) δ 167.2, 164.1, 154.5, 151.2, 141.7, 141.6, 139.2, 138.4, 137.2, 132.6, 132.1, 132.1, 131.8, 131.2, 129.4, 125.3, 121.7, 21.2, 20.1, 17.5, 16.7, 15.4, 14.5, 13.1. ESIMS [M−H]− calcd for C$_{24}$H$_{24}$BF$_2$N$_6$ 445.21. found 445.21.

Example 6—Characterization of TCO-Reacted 2b, 4b and 5b

Characterization of TCO-Reacted 2b

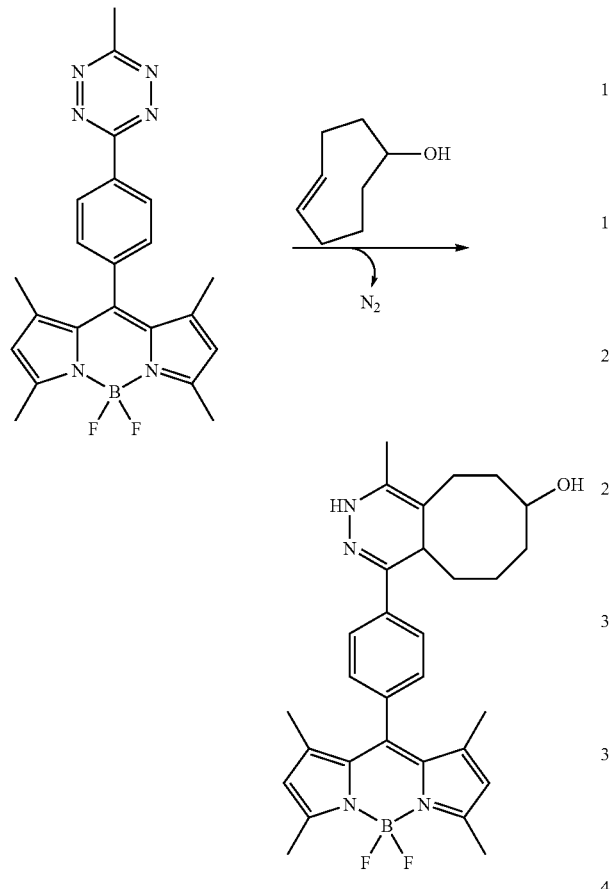

An aliquot of TCO-reacted 2b in MeCN was purified via flash column chromatography to remove excess TCO (dichloromethane:methanol gradient 20:0.1, 20:0.2, 20:0.3). $^1$H NMR (400 MHz, CDCl$_3$) δ 7.50 (d, J=6.4 Hz, 2H), 7.34 (d, J=8.0 Hz, 2H), 7.01 (s, 1H), 6.00 (s, 2H), 3.93 (m, 1H), 3.02 (dd, J=10, 6.4 Hz, 1H), 2.56 (s, 6H), 2.07 (s, 3H), 2.01-1.80 (m, 3H), 1.71-1.59 (m, 4H), 1.40 (s, 6H), 1.35-1.25 (m, 4H).

ESIMS [M+H]+ calcd for C$_{30}$H$_{36}$BF$_2$N$_4$O 517.30. found 517.34.

Characterization of TCO-Reacted 4b

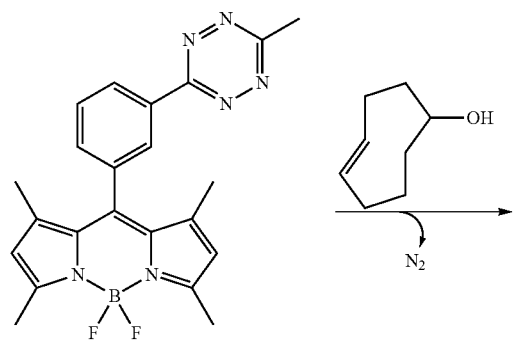

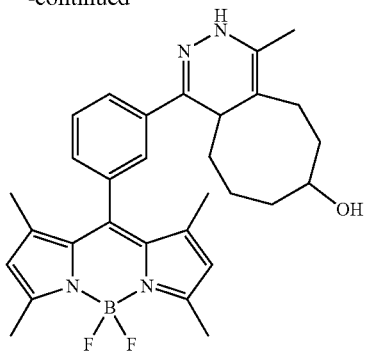

An aliquot of TCO reacted 4b in MeCN was purified via flash column chromatography to remove excess TCO (dichloromethane:methanol gradient 20:0.1, 20:0.2, 20:0.3). $^1$H NMR (400 MHz, CDCl3) δ 7.90 (d, J=8.4 Hz, 1H), 7.63 (t, J=1.6 Hz, 1H), 7.23 (m, 1H), 7.22 (m, 1H), 7.05 (s, 1H), 5.98 (s, 2H), 3.85 (m, 1H), 3.56 (dd, J=11.6, 3.6 Hz, 1H), 2.56 (s, 6H), 2.19 (m, 2H), 1.98-1.89 (m, 2H), 1.85 (s, 3H), 1.60 (m, 3H), 1.41 (s, 6H), 1.31 (m, 4H). ESIMS [M+H]+ calcd for C$_{30}$H$_{36}$BF$_2$N$_4$O 517.30. found 517.32.

Characterization of TCO-Reacted 5b

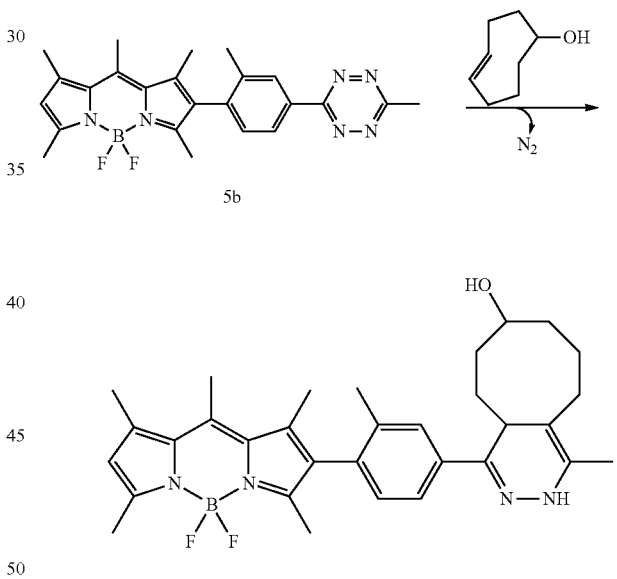

5b

An aliquot of TCO reacted 5b in MeCN was purified via flash column chromatography to remove excess TCO (dichloromethane:methanol gradient 20:0.1, 20:0.2, 20:0.3). $^1$H NMR (400 MHz, CDCl3) δ 7.69 (s, 1H), 7.57 (d, J=8 Hz, 1H), 7.09 (s, 1H), 7.07 (s, 1H), 6.08 (s, 1H), 3.90 (m, 1H), 3.54 (dd, J=9.6, 6.8 Hz, 1H), 2.64, (s, 3H), 2.54 (s, 3H), 2.44 (s, 3H), 2.33 (s, 3H), 2.18 (s, 3H), 2.13 (s, 3H), 1.94 (s, 3H), 1.86 (m, 2H), 1.82-1.75 (m, 4H), 1.64-1.58 (m, 4H), 1.32 (m, 1H). ESIMS [M+H]+ calcd for C$_{32}$H$_{39}$BF$_2$N$_4$O 545.33. found 545.38.

The quantum yield and fluorogenic activation of the compounds were measured and compared to the pre-TCO compounds. As shown in Table 1, the compound exhibited a significant increase in fluorescence as compared to the precursor compounds.

TABLE 1

| Probe | Φ w/TCO in water[a] | Φ w/TCO in MeCN[a] | Fluorescence increase in water[b] | Fluorescence increase in MeCN[b] |
|---|---|---|---|---|
| 2b | 0.80 | 0.23 | 900-fold | 340-fold |
| 4b | 0.73 | 0.58 | 1600-fold | 1100-fold |
| 5b | ND[c] | 0.22 | ND[c] | 120-fold |

[a]Quantum yield for dihydropyridazine product; fluorescein in 0.1M NaOH (pH 13, Φ = 0.925) was used as the standard.
[b]Increase in peak fluorescence intensity at reaction completion; for experiments in water, 400 nM BODIPY-Tz, and 1 μM TCO were used.
[c]Compound 5b is insufficiently soluble in water for this determination.

The exceptional fluorogenic turn-on of 2 and 4—as much as 100-fold greater than flexibly linked fluorophore-Tz conjugates-suggested that FRET may not be the sole quenching mechanism for these compounds.

Example 7—Absorption and Fluorescence of 4b and TCO-Reacted 4b

Figure 5:
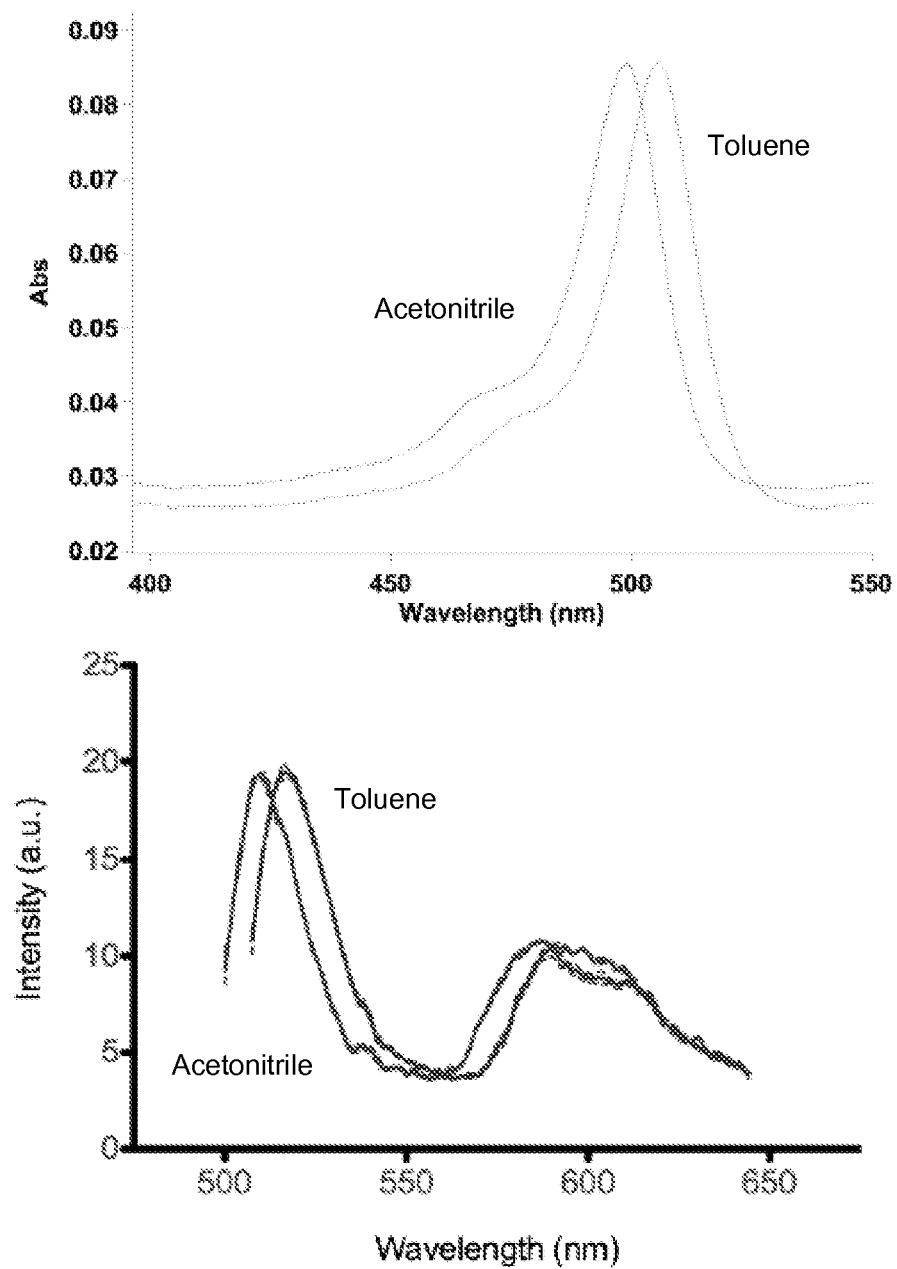
FIG. 5 shows the absorption and fluorescence emission spectra of 4b in toluene and acetonitrile.

FIG. 5 provides the absorption and fluorescence emission spectra of 4b in toluene (dielectric constant 2.4) and acetonitrile (dielectric constant 37.5). Samples were prepared by matched dilutions from a concentrated stock solution of 4b. For the fluorescence spectra, the excitation wavelength was offset from peak absorbance in that solvent by 10 nm; in toluene, the excitation wavelength was 496 nm; in acetonitrile, 489 nm. Emission spectra are the mean of three scans and dashed lines correspond to +/−SEM.

Figure 6:
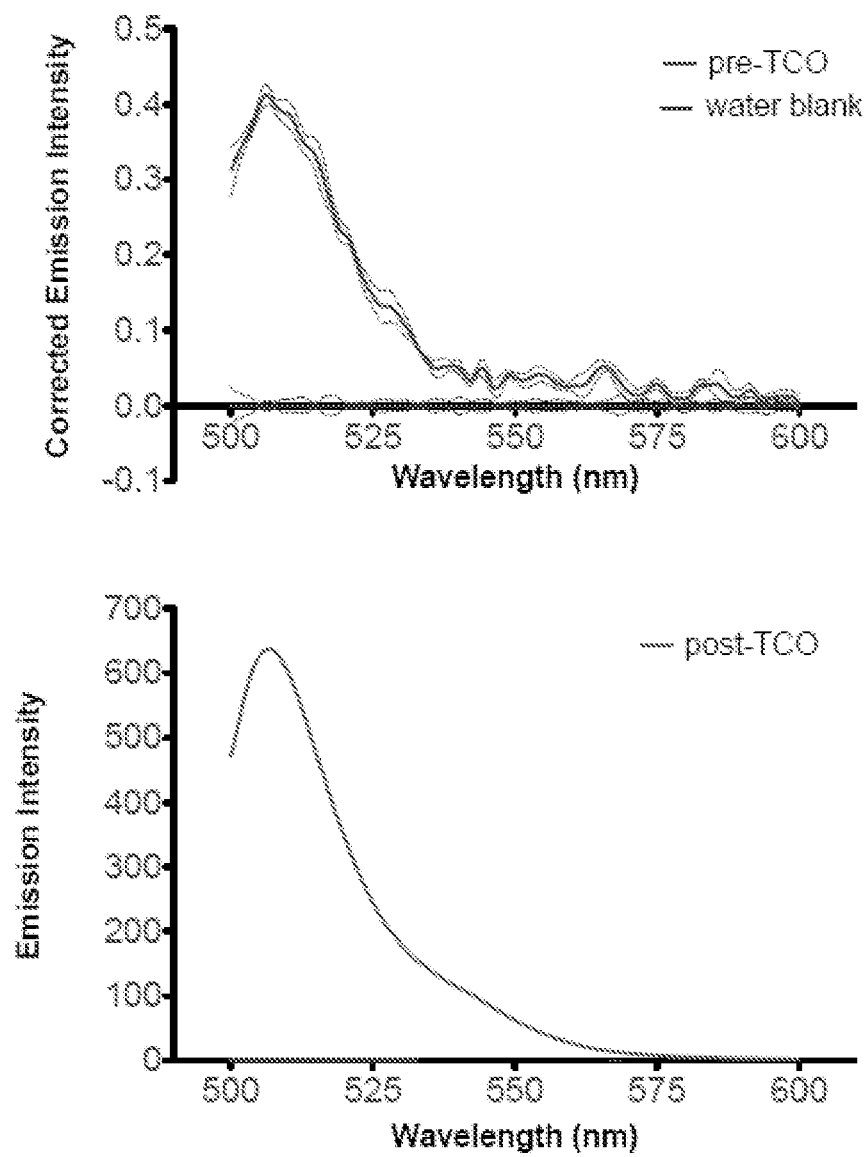
FIG. 6 illustrates the fluorogenic activation of 4b in water.

The activation of 4b upon reaction with TCO is demonstrated in FIG. 6, which shows the emission spectra (excitation 490 nm) of compound 4b in water, before and after addition of TCO. For baseline and pre-TCO spectra, data plotted are means of 3 scans and dashed lines indicate +/−SEM.

Given that the fluorescence emission intensity of 4b was found to be independent of solvent polarity, redox-based quenching, such as via photoinduced-electron transfer (PET) from the excited BODIPY to the relatively electron-poor tetrazine ring, was judged unlikely.

Example 8—Biological Application of Activatable BODIPY

Figure 7:
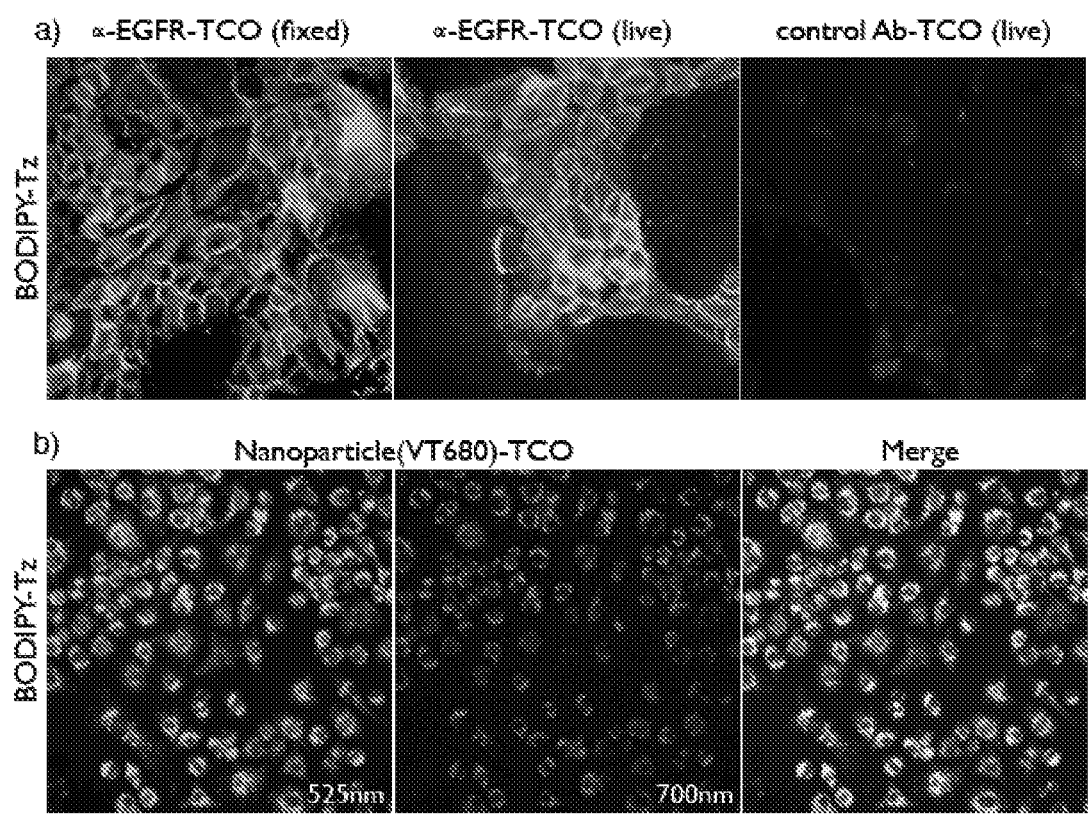
FIG. 7 illustrates the biological application of the compounds provided herein.

Having advanced our understanding of the quenching mechanism, the utility of fluorogenic BODIPY-tetrazines for biological imaging was explored further (see FIG. 7). FIG. 7A shows fluorogenic imaging of EGFR expression on both fixed and live A431 cells. Cells were incubated with TCO-conjugated monoclonal antibodies (see S. S. Agasti et al., Small 2013, 9, 222-227), washed, and then imaged immediately after the addition of 100 nM BODIPY-Tz in PBS. As shown in FIG. 7B, Fluorogenic live-cell imaging of intracellular nanoparticles internalized by RAW 264.7 cells. The nanoparticles are labeled with both TCO and with the near-infrared dye VT680 (see S. S. Agasti et al., Small 2013, 9, 222-227), and were imaged in two channels after addition of 100 nM BODIPY-Tz, demonstrating co-localization. Both extracellular and intracellular TCO-labeled targets were readily visualized, with excellent signal intensity, very low background, and with no washing steps required after addition of the dye solution.

Example 9—Preparation of Compound 7

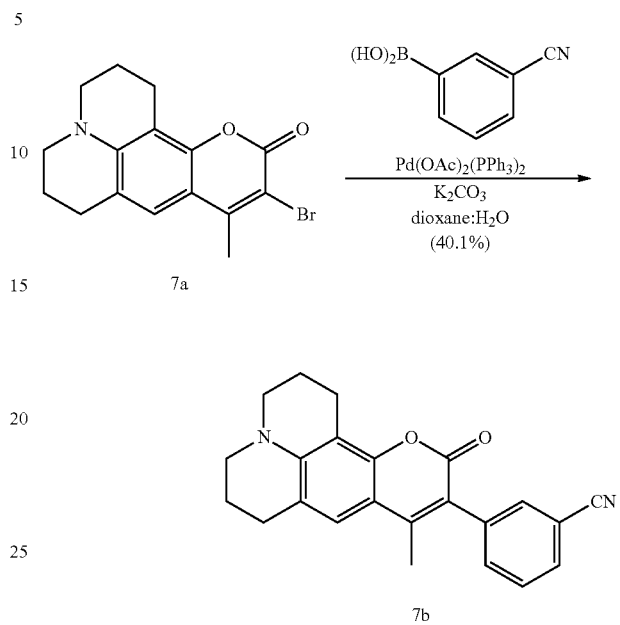

To bromocoumarin 7a (245.0 mg, 0.733 mmol) in 8.0 mL of dioxane:water (3:1) was added 3-cyanophenylboronic acid (215.4 mg, 1.47 mmol), Pd(OAc)$_2$(PPh$_3$)$_2$ (27.4 mg, 0.037 mmol), and K$_2$CO$_3$ (202.6 mg, 1.46 mmol). The reaction mixture was refluxed for 7 hours after which it was concentrated using a rotary evaporator and purified using flash column chromatography (hexanes:ethyl acetate gradient, 6:1 to 4:1) to give 7b (105.0 mg, 0.29 mmol, 40.1%) as a yellow solid.

$^1$H NMR (400 MHz, CDCl$_3$) δ 7.61-7.47 (m, 4H), 7.04 (s, 1H), 3.25 (m, 4H), 2.89 (t, J=6.4 Hz, 2H), 2.76 (t, J=6.0 Hz, 2H), 2.16 (s, 3H), 1.97 (m, 4H); $^{13}$C NMR (100 MHz, CDCl$_3$) δ 161.9, 150.5, 149.5, 146.2, 137.4, 135.6, 134.5, 131.2, 129.2, 122.6, 118.9, 118.5, 118.1, 112.6, 109.0, 106.7, 50.1, 49.7, 27.9, 21.7, 20.8, 20.6, 16.6. ESIMS [M+H]$^+$ calcd for C$_{23}$H$_{21}$N$_2$O$_2$ 357.42. found 357.16.

Bromocoumarin 7a was prepared from literature protocol (Gong, et al., PCT Int. Appl. (2006), WO 2006026368).

Example 10—Preparation of HyperEmissive Ligation-Initiated Orthogonal Sensing (HELIOS) Probe 400 Me

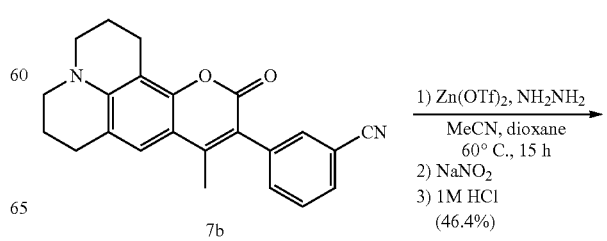

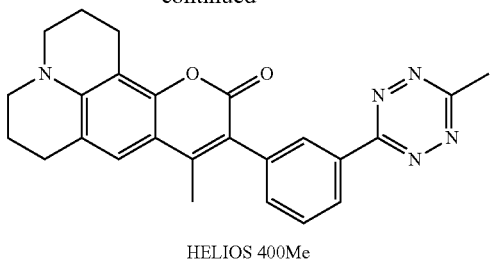

HELIOS 400Me

To nitrile 7b (100.0 mg, 0.28 mmol) in a microwave reaction tube under a stream of argon was added Zn(OTf)$_2$ (51.3 mg, 0.14 mmol), MeCN (0.15 mL, 2.80 mmol), dioxane (0.22 mL) and NH$_2$NH$_2$ (0.44 mL, 14.0 mmol). The vessel was sealed and allowed to stir at 60° C. for hours after which it was allowed to cool and the septum removed. To the reaction mixture was added NaNO$_2$ (386.4 mg, 5.60 mmol) in 10 mL of water followed by 1 M HCl until the pH=3. The aqueous phase was extracted three times with methylene chloride (100 mL). The combined organic extracts were dried with MgSO$_4$ and concentrated using a rotary evaporator. The crude mixture was purified using flash column chromatography (hexanes:ethyl acetate gradient, 5:1 to 1:1) to give HELIOS 400Me (55.3 mg, 0.13 mmol, 46.4%) as an orange solid.

$^1$H NMR (400 MHz, CDCl$_3$) δ 8.55 (d, J=8.0 Hz, 1H), 8.50 (s, 1H), 7.63 (t, J=8.0 Hz, 1H), 7.55 (d, J=7.6 Hz, 1H), 7.06 (s, 1H), 3.26 (m, 4H), 3.07 (s, 3H), 2.93 (t, J=6.4 Hz, 2H), 2.79 (t, J=6.4 Hz, 2H), 2.23 (s, 3H), 1.99 (m, 4H); $^{13}$C NMR (100 MHz, CDCl$_3$) δ 167.4, 164.3, 162.1, 150.4, 149.1, 145.6, 137.2, 135.2, 132.0, 130.3, 129.4, 127.2, 122.6, 119.9, 118.6, 109.7, 107.2, 50.2, 49.8, 27.9, 21.8, 21.3, 20.9, 20.7, 16.7. ESIMS [M+H]+ calcd for C$_{25}$H$_{24}$N$_5$O$_2$ 426.19. found 426.24.

Example 11—Preparation of HELLOS 400H

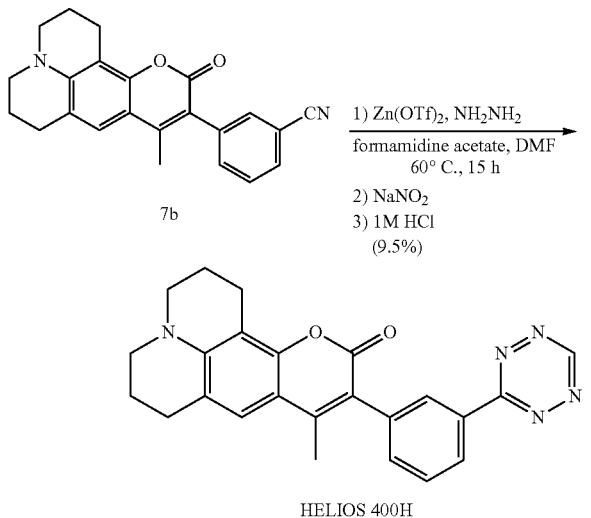

HELIOS 400H

To nitrile 7b (110.4 mg, 0.31 mmol) in a microwave reaction tube under a stream of argon was added Zn(OTf)$_2$ (56.6 mg, 0.15 mmol), formamidine acetate (322.7 mg, 3.10 mmol), DMF (0.24 mL) and NH$_2$NH$_2$ (0.49 mL, 15.5 mmol). The vessel was sealed and allowed to stir at 60° C. for 15 hours after which it was allowed to cool and the septum removed. To the reaction mixture was added NaNO$_2$ (427.8 mg, 6.20 mmol) in 10 mL of water followed by 1 M HCl until the pH=3. The aqueous phase was extracted three times with methylene chloride (100 mL). The combined organic extracts were dried with MgSO$_4$ and concentrated using a rotary evaporator. The crude mixture was purified using flash column chromatography (hexanes:ethyl acetate gradient, 4:1 to 2:1) to give HELIOS 400H (12.1 mg, 0.029 mmol, 9.5%) as an orange solid.

$^1$H NMR (400 MHz, CDCl$_3$) δ 10.19 (s, 1H), 8.60 (d, J=7.6 Hz, 1H), 8.54 (s, 1H), 7.66 (t, J=7.6 Hz, 1H), 7.60 (d, J=8.0 Hz, 1H), 7.08 (s, 1H), 3.28 (m, 4H), 2.94 (t, J=6.4 Hz, 2H), 2.81 (t, J=6.4 Hz, 2H), 2.24 (s, 3H), 2.01 (m, 4H); $^{13}$C NMR (100 MHz, CDCl$_3$) δ 166.5, 161.9, 157.8, 150.3, 148.9, 145.6, 137.2, 135.6, 131.6, 130.6, 129.4, 127.4, 122.4, 119.6, 118.4, 109.4, 106.9, 50.0, 49.6, 27.8, 21.6, 20.7, 20.5, 16.5. ESIMS [M+H]+ calcd for C$_{24}$H$_{22}$N$_5$O$_2$ 412.17. found 412.18.

Example 12—Preparation of 7c

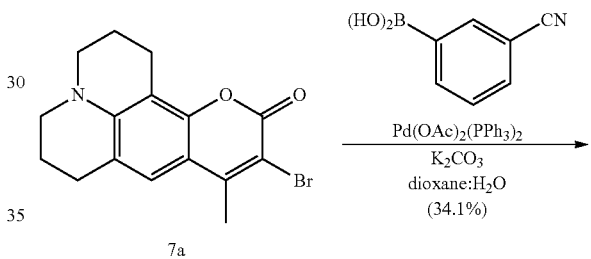

7a

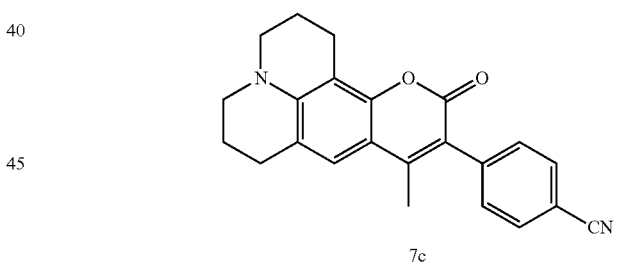

7c

To bromocoumarin 7a (105.5 mg, 0.31 mmol) in 4.0 mL of dioxane:water (3:1) was added 3-cyanophenylboronic acid (91.1 mg, 0.62 mmol), Pd(OAc)$_2$(PPh$_3$)$_2$ (11.6 mg, 0.015 mmol), and K$_2$CO$_3$ (85.6 mg, 0.62 mmol). The reaction mixture was refluxed for 7 hours after which it was concentrated using a rotary evaporator and purified using flash column chromatography (hexanes:ethyl acetate gradient, 6:1 to 4:1) to give 1c (37.7 mg, 0.10 mmol, 34.1%) as a yellow solid.

$^1$H NMR (400 MHz, (CD$_3$)$_2$SO) δ 7.86 (d, J=8.0 Hz, 2H), 7.48 (d, J=8.0 Hz, 2H), 7.20 (s, 1H), 3.25 (m, 4H), 2.75 (m, 4H), 2.14 (s, 3H), 1.89 (m, 4H); $^{13}$C NMR (100 MHz, (CD3)$_2$SO) δ 160.2, 149.7, 149.3, 145.6, 140.8, 131.8 (2C), 122.8, 118.8, 118.0, 117.3, 109.9, 108.0, 105.2, 49.2, 48.6, 27.0, 20.9, 20.1, 19.9, 16.1. ESIMS [M+H]$^+$ calcd for C$_{23}$H$_{21}$N$_2$O$_2$ 357.16. found 357.16.

Example 13—Preparation of HELIOS 400pMe

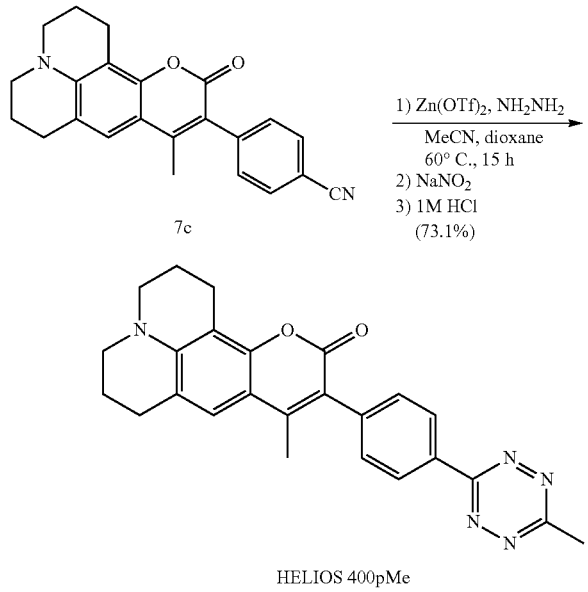

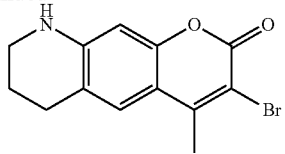

To nitrile 7c (37.7 mg, 0.10 mmol) in a microwave reaction tube under a stream of argon was added Zn(OTf)$_2$ (19.3 mg, 0.52 mmol), MeCN (0.055 mL, 1.05 mmol), dioxane (0.083 mL) and NH$_2$NH$_2$ (0.16 mL, 5.28 mmol). The vessel was sealed and allowed to stir at 60° C. for 15 hours after which it was allowed to cool and the septum removed. To the reaction mixture was added NaNO$_2$ (145.9 mg, 2.11 mmol) in 10 mL of water followed by 1 M HCl until the pH=3. The aqueous phase was extracted three times with methylene chloride (100 mL). The combined organic extracts were dried with MgSO$_4$ and concentrated using a rotary evaporator. The crude mixture was purified using flash column chromatography (hexanes:ethyl acetate gradient, 4:1 to 2:1) to give HELIOS 400pMe (31.1 mg, 0.073 mmol, 73.1%) as an orange solid.

$^1$H NMR (400 MHz, CDCl$_3$) δ 8.63 (d, J=8.0 Hz, 2H), 7.51 (d, J=8.0 Hz, 2H), 7.06 (s, 1H), 3.26, (m, 4H), 3.08 (s, 3H), 2.93 (t, J=6.0 Hz, 2H), 2.79 (t, J=6.4 Hz, 2H), 2.34 (s, 3H), 1.99 (m, 4H); $^{13}$C NMR (100 MHz, CDCl$_3$) δ 167.4, 164.2, 161.9, 150.5, 149.0, 145.8, 140.7, 131.9 (2C), 130.9, 127.9 (2C), 122.6, 119.7, 118.5, 109.4, 106.9, 50.2, 49.8, 28.0, 21.8, 21.4, 20.9, 20.7, 16.7. ESIMS [M+H]$^+$ calcd for C$_{25}$H$_{24}$N$_5$O$_2$ 426.19. found 426.19.

Example 14—Preparation of 8a

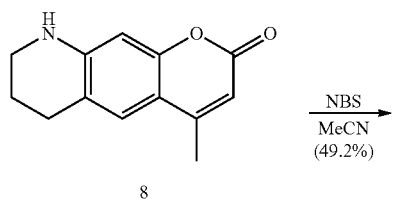

To coumarin 339 (8) (410.6 mg, 1.90 mmol) dissolved in 25 mL of acetonitrile was added NBS (373.7 mg, 2.10 mmol) and the reaction mixture allowed to stir for 2 hours. The crude mixture was concentrated using a rotary evaporator and purified using flash column chromatography (methylene chloride to methylene chloride:methanol 250:1) to give 8a (276.4 mg, 0.94 mmol, 49.4%) as a yellow solid.

$^1$H NMR (400 MHz, (CD$_3$)$_2$SO) δ 7.27 (s, 1H), 6.93 (bs, 1H), 6.29 (s, 1H), 3.24 (t, J=4.8 Hz, 2H), 2.72 (t, J=5.6 Hz, 2H), 2.44 (s, 3H), 1.79 (m, 2H); $^{13}$C NMR (100 MHz, (CD$_3$)$_2$SO) δ 156.9, 152.2, 152.1, 149.4, 125.6, 118.1, 107.9, 103.2, 97.0, 40.3, 26.3, 20.6, 18.9. ESIMS [M+H]$^+$ calcd for C$_{13}$H$_{13}$BrNO$_2$ 294.01. found 294.00. Coumarin 339 (8) was prepared from literature protocol (R. L. Atkins, D. E. Bliss, J. Org. Chem. 1978, 43, 1975).

Example 15—Preparation of 8b

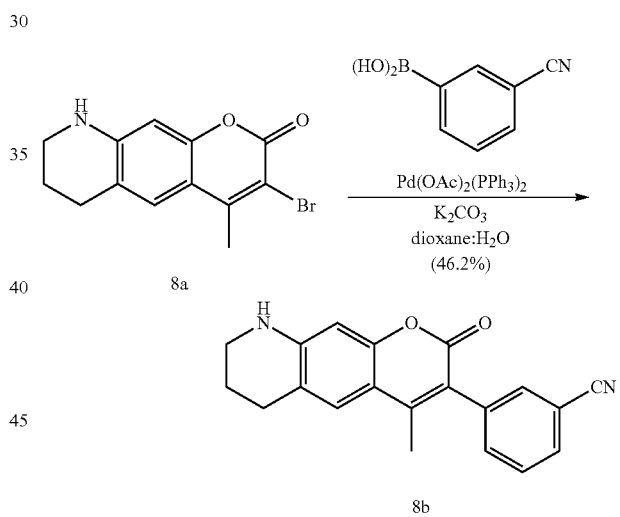

To bromocoumarin 8a (150 mg, 0.51 mmol) in 5.2 mL of dioxane:water (3:1) was added 3-cyanophenylboronic acid (151.6 mg, 1.01 mmol), Pd(OAc)$_2$(PPh$_3$)$_2$ (19.1 mg, 0.025 mmol), and K$_2$CO$_3$ (140.9 mg, 1.01 mmol). The reaction mixture was refluxed for 7 hours after which it was concentrated using a rotary evaporator and purified using flash column chromatography (hexanes:ethyl acetate gradient, 4:1 to 2:1) to give 8b (74.5 mg, 0.23 mmol, 46.2%) as a yellow solid.

$^1$H NMR (400 MHz, CD$_3$OD) δ 7.72 (m, 1H), 7.67 (s, 1H), 7.60 (m, 2H), 7.33 (s, 11H), 6.36 (s, 1H), 3.36 (t, J=5.6 Hz, 2H), 2.83 (t, J=6.4 Hz, 2H), 2.23 (s, 3H), 1.93 (quin, J=5.6 Hz, 2H); $^{13}$C NMR (100 MHz, (CD$_3$)$_2$SO) δ 160.4, 152.9, 149.5, 149.1, 136.9, 135.7, 134.2, 131.0, 129.2, 125.7, 118.7, 117.7, 116.9, 111.1, 108.2, 97.1, 40.4, 26.4, 20.7, 16.1. ESIMS [M+H]$^+$ calcd for C$_{20}$H$_{17}$N$_2$O$_2$ 317.12. found 317.18.

Example 16—Preparation of HELIOS 388Me

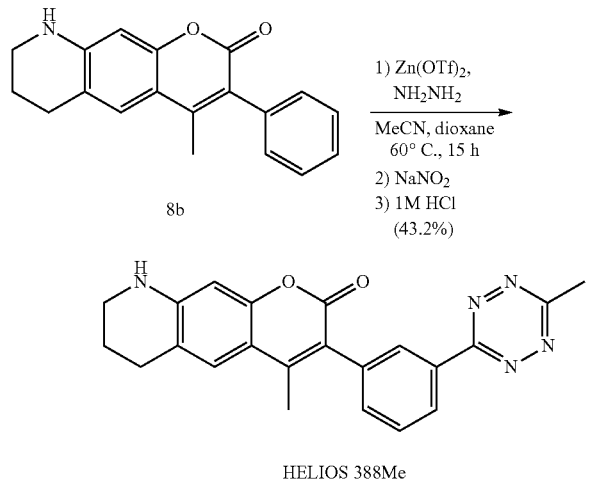

HELIOS 388Me

To nitrile 8b (64.8 mg, 0.20 mmol) in a microwave reaction tube under a stream of argon was added Zn(OTf)$_2$ (37.4 mg, 0.10 mmol), MeCN (0.11 mL, 2.10 mmol), dioxane (0.16 mL) and NH$_2$NH$_2$ (0.32 mL, 10.20 mmol). The vessel was sealed and allowed to stir at 60° C. for 15 hours after which it was allowed to cool and the septum removed. To the reaction mixture was added NaNO$_2$ (276.0 mg, 4.0 mmol) in 10 mL of water followed by 1 M HCl until the pH=3. The aqueous phase was extracted three times with methylene chloride (100 mL). The combined organic extracts were dried with MgSO$_4$ and concentrated using a rotary evaporator. The crude mixture was purified using flash column chromatography (hexanes:ethyl acetate gradient, 3:1 to 1:1) to give HELIOS 388Me (33.3 mg, 0.086 mmol, 43.2%) as an orange solid.

$^1$H NMR (400 MHz, CDCl$_3$) δ 8.56 (d, J=8.0 Hz, 1H), 8.50 (s, 1H), 7.64 (t, J=7.6 Hz, H), 7.56 (d, J=7.6 Hz, 1H), 7.18 (s, 1H), 6.37 (s, 1H), 4.55 (s, 1H), 3.37 (m, 2H), 3.07 (s, 3H), 2.80 (t, J=6.0 Hz, 2H), 2.25 (s, 3H), 1.95 (quin, J=5.6 Hz, 2H); $^{13}$C NMR (100 MHz, CDCl$_3$) δ 167.5, 164.3, 162.1, 153.6, 149.1, 148.3, 136.9, 135.1, 132.1, 130.3, 129.5, 127.3, 125.7, 120.5, 118.5, 110.6, 99.2, 41.8, 27.2, 21.7, 21.4, 16.7. ESIMS [M+H]$^+$ calcd for C$_{22}$H$_{20}$N$_5$O$_2$ 386.16, found 386.13.

Example 17—Preparation of HELIOS 388H

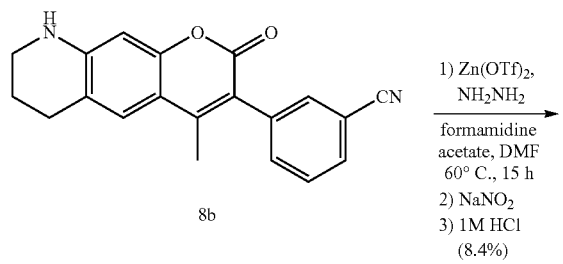

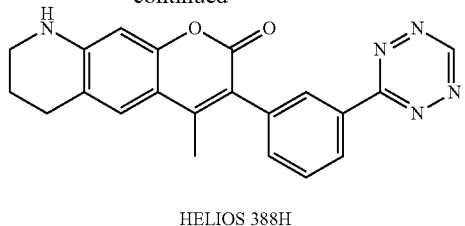

HELIOS 388H

To nitrile 8b (76.7 mg, 0.24 mmol) in a microwave reaction tube under a stream of argon was added Zn(OTf)$_2$ (44.3 mg, 0.12 mmol), formamidine acetate (251.9 mg, 2.42 mmol), DMF (0.19 mL) and NH$_2$NH$_2$ (0.38 mL, 12.1 mmol). The vessel was sealed and allowed to stir at 60° C. for 15 hours after which it was allowed to cool and the septum removed. To the reaction mixture was added NaNO$_2$ (333.9 mg, 4.84 mmol) in 10 mL of water followed by 1 M HCl until the pH=3. The aqueous phase was extracted three times with methylene chloride (100 mL). The combined organic extracts were dried with MgSO$_4$ and concentrated using a rotary evaporator. The crude mixture was purified using flash column chromatography (hexanes:ethyl acetate gradient, 3:1 to 1:1) to give HELIOS 388H (7.48 mg, 0.020 mmol, 8.4%) as an orange solid.

$^1$H NMR (400 MHz, (CD$_3$)$_2$SO) δ 10.62 (s, 1H), 8.50 (d, J=8.0 Hz, 1H), 8.38 (s, 1H), 7.74 (t, J=7.6 Hz, 1H), 7.62 (d, J=7.6 Hz, 1H), 7.33 (s, 1H), 6.86 (s, 1H), 6.36 (s, 1H), 3.28 (m, 2H), 2.76 (t, J=6.0 Hz, 2H), 2.23 (s, 3H), 1.82 (m, 2H); $^{13}$C NMR (100 MHz, (CD$_3$)$_2$SO) δ 165.4, 160.6, 158.1, 152.9, 149.2, 149.0, 136.8, 135.1, 131.7, 129.9, 129.2, 126.7, 125.7, 118.1, 117.7, 108.4, 97.2, 40.4, 26.5, 20.8, 16.2. ESIMS [M+H]$^+$ calcd for C$_{21}$H$_{18}$N$_5$O$_2$ 372.14. found 372.12.

Example 18—Preparation of 9b

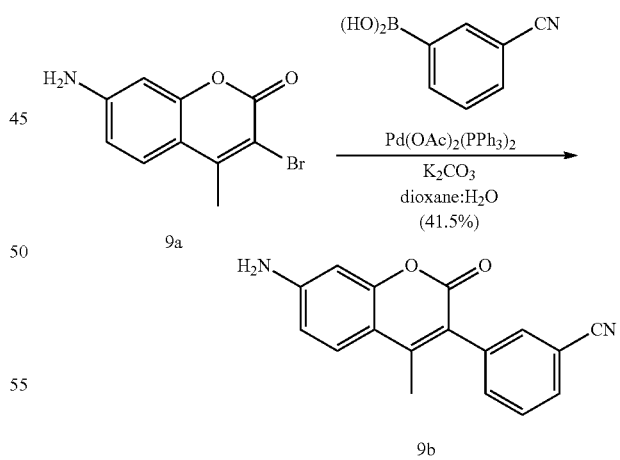

To bromocoumarin 9a (5.25 g, 20.7 mmol) in 133.0 mL of dioxane:water (3:1) was added 3-cyanophenylboronic acid (4.56 g, 31.0 mmol), Pd(OAc)$_2$(PPh$_3$)$_2$ (775.3 mg, 1.03 mmol), and K$_2$CO$_3$ (5.71 g, 41.4 mmol). The reaction mixture was refluxed for 2 hours after which it was concentrated using a rotary evaporator. The crude was partitioned between water and methylene chloride and extracted 3 times (250 mL), concentrated using a rotary evaporator and purified using flash column chromatography (methylene chloride:methanol, 10:0.05) to give 3b (2.38 g, 8.6 mmol, 41.5%) as a white solid.

$^1$H NMR (400 MHz, (CD$_3$)$_2$SO) δ 7.82 (m, 1H), 7.78 (s, 1H), 7.64 (m, 2H), 7.50 (d, J=8.4 Hz, 1H) 6.63 (d, J=8.8 Hz, 1H), 6.46 (s, 1H), 6.19 (s, 2H), 2.15 (s, 3H); $^{13}$C NMR (100 MHz, (CD$_3$)$_2$SO) δ 160.4, 154.6, 153.1, 149.6, 136.7, 135.7, 134.2, 131.1, 129.3, 126.9, 118.7, 117.6, 111.6, 111.2, 108.9, 99.3, 16.2. ESIMS [M+H]$^+$ calcd for C$_{17}$H$_{13}$N$_2$O$_2$ 277.09. found 277.06.

Bromocoumarin 9a was prepared from literature protocol (M. S. Schiedel, C. A. Briehn, P. Bauerle, Angew. *Chem. Int. Ed.* 2001, 40, 4677-4680).

Example 19—Preparation of HELIOS 327Me

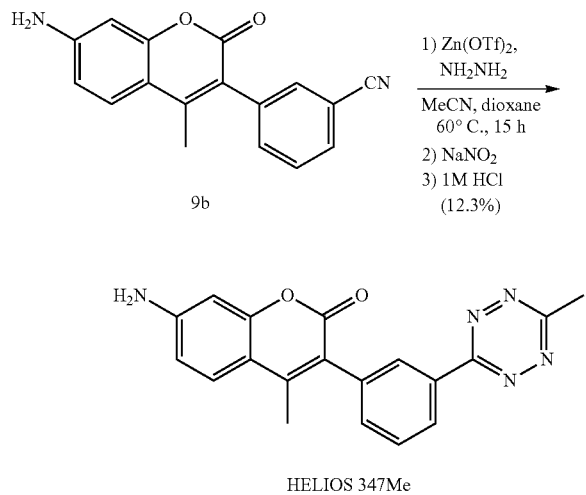

HELIOS 347Me

To nitrile 9b (39.0 mg, 0.14 mmol) in a microwave reaction tube under a stream of argon was added Zn(OTf)$_2$ (25.8 mg, 0.070 mmol), MeCN (0.073 mL, 1.40 mmol), dioxane (0.11 mL) and NH$_2$NH$_2$ (0.22 mL, 7.00 mmol). The vessel was sealed and allowed to stir at 60° C. for 15 hours after which it was allowed to cool and the septum removed. To the reaction mixture was added NaNO$_2$ (193.2 mg, 2.80 mmol) in 10 mL of water followed by 1 M HCl until the pH=3. The aqueous phase was extracted three times with methylene chloride (100 mL). The combined organic extracts were dried with MgSO$_4$ and concentrated using a rotary evaporator. The crude mixture was purified using flash column chromatography (hexanes:ethyl acetate gradient, 2:1 to 1:1) to give HELIOS 347Me (5.94 mg, 0.017 mmol, 12.3%) as a red solid.

$^1$H NMR (400 MHz, (CD$_3$)$_2$SO) δ 8.46 (d, J=7.6 Hz, 1H), 8.35 (s, 1H), 7.72 (t, J=8.0 Hz, 1H), 7.60 (d, J=7.6 Hz, 1H), 7.52 (d, J=8.4 Hz, 1H), 6.62 (d, J=8.4 Hz, 1H), 6.48 (s, 1H), 6.16 (s, 2H), 3.00 (s, 3H), 2.22 (s, 3H); $^{13}$C NMR (100 MHz, (CD$_3$)$_2$SO) δ 167.1, 163.2, 160.6, 154.6, 152.9, 149.2, 136.5, 134.6, 131.8, 129.5, 129.2, 126.9, 126.4, 118.7, 111.5, 109.0, 98.3, 20.8, 16.2. ESIMS [M+H]+ calcd for C$_{19}$H$_{16}$N$_5$O$_2$ 346.13. found 346.11.

Example 20—Preparation of HELIOS 347H

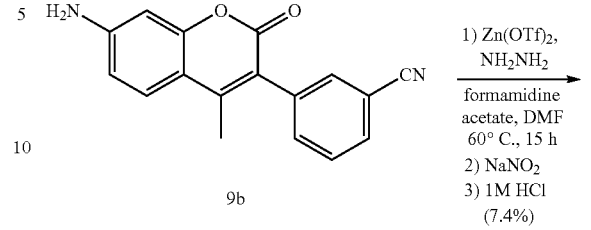

HELIOS 347H

To nitrile 9b (200.0 mg, 0.72 mmol) in a microwave reaction tube under a stream of argon was added Zn(OTf)$_2$ (132.2 mg, 0.36 mmol), formamidine acetate (749.6 mg, 7.2 mmol), DMF (0.56 mL) and NH$_2$NH$_2$ (1.13 mL, 36.0 mmol). The vessel was sealed and allowed to stir at 60° C. for 15 hours after which it was allowed to cool and the septum removed. To the reaction mixture was added NaNO$_2$ (993.6 mg, 14.4 mmol) in 15 mL of water followed by 1 M HCl until the pH=3. The aqueous phase was extracted three times with methylene chloride (150 mL). The combined organic extracts were dried with MgSO$_4$ and concentrated using a rotary evaporator. The crude mixture was purified using flash column chromatography (hexanes:ethyl acetate gradient, 2:1 to 1:1) to give HELIOS 347H (17.6 mg, 0.053 mmol, 7.4%) as a red solid.

$^1$H NMR (400 MHz, (CD$_3$)$_2$SO) δ 10.61 (s, 1H), 8.50 (d, J=8.0 Hz, 1H), 8.39 (s, 1H), 7.75 (t, J=8.0 Hz, 1H), 7.63 (d, J=7.6 Hz, 1H), 7.52 (d, J=8.4 Hz, 1H), 6.62 (dd, J=8.8, 2.4 Hz, 1H), 6.48 d (J=2.0 Hz, 1H), 6.16 (s, 2H), 2.23 (s, 3H); $^{13}$C NMR (100 MHz, (CD$_3$)$_2$SO) δ 165.4, 160.6, 158.1, 154.6, 152.9, 149.2, 136.6, 135.0, 131.8, 129.8, 129.2, 126.9, 126.7, 118.6, 111.5, 109.0, 98.3, 16.2. ESIMS [M+H]$^+$ calcd for C$_{18}$H$_{14}$N$_5$O$_2$ 332.11. found 332.09.

Example 21—Preparation of 10a

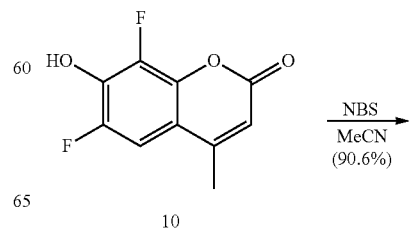

-continued

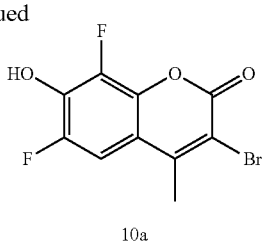

10a

To difluorinated hydroxycoumarin (Marina Blue®) (10) (1.06 g, 4.99 mmol) dissolved in 50 mL of acetonitrile was added NBS (0.93 g, 5.24 mmol) and the reaction mixture allowed to stir for 1 hour. The crude mixture was concentrated using a rotary evaporator and purified using flash column chromatography (hexanes:ethyl acetate, 2:1) to give 10a (1.32 g, 4.52 mmol, 90.6%) as a white solid.

$^1$H NMR (400 MHz, MeOD) δ 7.30 (d, J=11.2 Hz, 1H), 2.51 (s, 3H); $^{13}$C NMR (100 is MHz, MeOD) δ 147.9, 143.3 (t, J=2.8 Hz), 141.0 (dd, J=234.7, 5.0 Hz), 131.3 (dd, J=216.0, 6.4 Hz), 129.9 (m, 2C), 102.7 (d, J=9.1 Hz), 101.7, 97.7 (dd, J=19.0, 3.3), 10.4. ESIMS [M–H]$^-$ calcd for $C_{10}H_4BrF_2O_3$ 288.93. found 288.88.

Example 21—Preparation of 10b

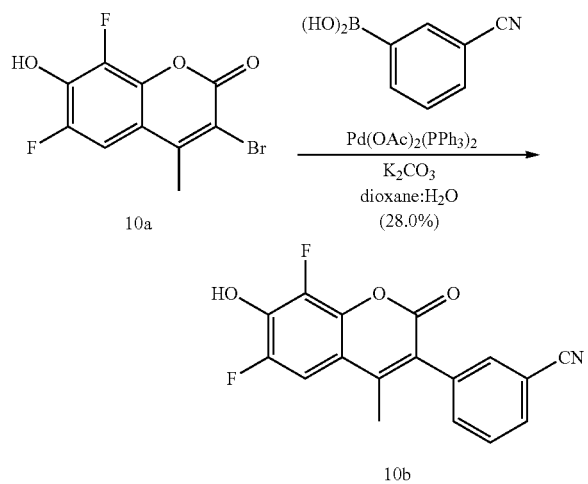

To bromocoumarin 10a (475.9 mg, 1.63 mmol) in 15.0 mL of dioxane:water (3:1) was added 3-cyanophenylboronic acid (479.0 mg, 3.26 mmol), Pd(OAc)$_2$(PPh$_3$)$_2$ (61.2 mg, 0.082 mmol), and K$_2$CO$_3$ (225.3 mg, 3.26 mmol). The reaction mixture was refluxed for 7 hours after which it was concentrated using a rotary evaporator and purified using flash column chromatography (hexanes:ethyl acetate gradient, 2:1 to 1:1) to give 4b (142.9 mg, 0.45 mmol, 28.0%) as a white solid.

$^1$H NMR (400 MHz, (CD$_3$)$_2$SO) δ 7.89 (t, J=3.6 hz, 1H), 7.83 (s, 1H), 7.69 (m, 2H), 7.60 (d. J=11.6 Hz, 1H), 2.21 (s, 3H); $^{13}$C NMR (100 MHz, (CD$_3$)$_2$SO) δ 158.7, 148.8 (t, J=2.6 Hz), 148.6 (dd, J=232.6, 5.2 Hz), 139.1 (dd, J=235.8, 6.8 Hz), 138.5 (dd, J=7.6, 1.8 Hz), 137.6 (dd, J=12.7, 5.3 Hz), 135.7, 135.3, 133.8, 131.8, 129.5, 122.6, 118.5, 111.4, 111.1 (d, J=8.9 Hz), 107.0 (dd, J=18.6, 2.9 Hz), 16.6. ESIMS [M+H]$^+$ calcd for $C_{17}H_{10}F_2NO_3$ 314.06. found 314.01.

Example 22—Preparation of 4c

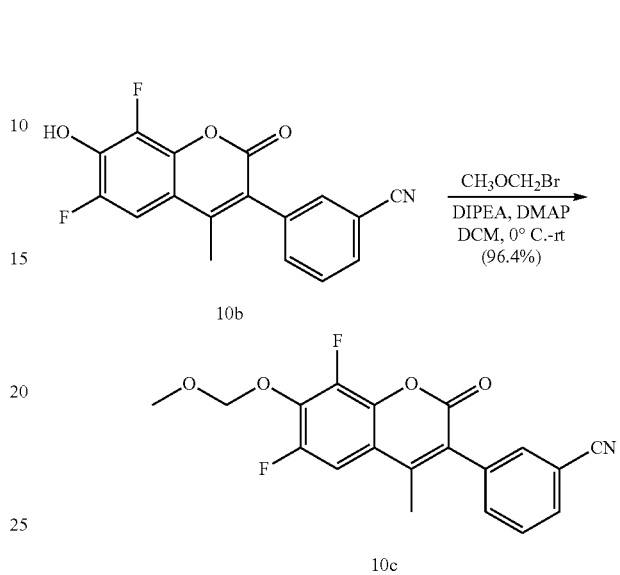

To nitrile 10b (91.1 mg, 0.29 mmol) in 3.0 mL of methylene chloride was added N,N-Diisopropylethylamine (0.15 mL, 0.87 mmol) and DMAP (1.77 mg, 0.014 mmol). The mixture was then cooled to 0° C. and bromomethyl methyl ether (0.059 mL, 0.72 mmol) was added dropwise. The ice bath was removed and the reaction was allowed to stir at room temperature for one hour after which it was concentrated using a rotary evaporator and purified using flash column chromatography (hexanes:ethyl acetate 4:1) to give 10c (99.9 mg, 0.28 mmol, 96.4%) as a white solid.

$^1$H NMR (400 MHz, CDCl$_3$) δ 7.71 (d, J=7.6 Hz, 1H), 7.58 (s, 1H), 7.54 (m, 2H), 7.20 (dd, J=8.8, 2.0 Hz, 1H), 5.28 (s, 2H), 3.59 (s, 3H), 2.25 (s, 3H); $^{13}$C NMR (100 MHz, CDCl$_3$) δ 159.0, 152.5 (dd, J=241.0, 4.0 Hz), 147.8 (t, J=2.6 Hz), 144.1 (dd, J=246.7, 5.8 Hz), 139.1 (dd, J=8.1, 2.4 Hz), 136.4 (dd, J=11.2, 4.7 Hz), 135.4, 134.8, 133.9, 132.3, 129.7, 125.7, 118.5, 116.1 (d, J=8.8 Hz), 113.2, 106.5 (dd, J=18.6, 3.8 Hz), 99.3 (t, J=3.8 Hz), 57.6, 17.1. ESIMS [M+H]$^+$ calcd for $C_{19}H_{14}F_2NO_4$ 358.08. found 358.04.

Example 23—Preparation of HELIOS 370Me

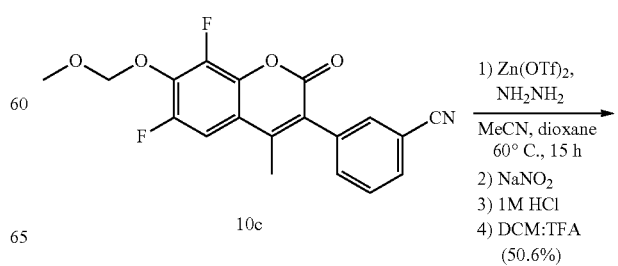

75 -continued

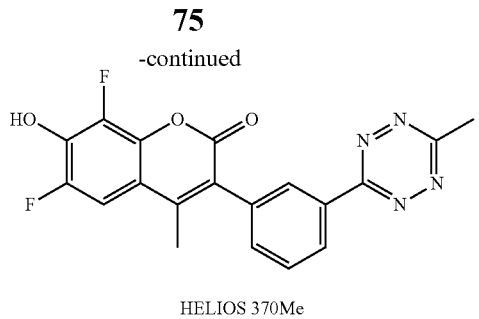

HELIOS 370Me

76 -continued

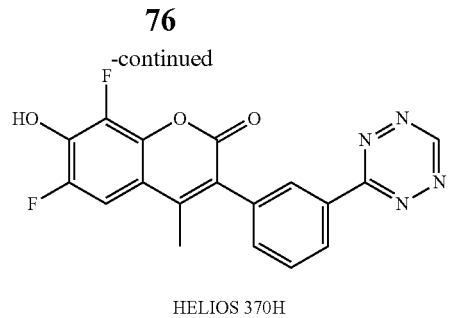

HELIOS 370H

To nitrile 10c (144.0 mg, 0.40 mmol) in a microwave reaction tube under a stream of argon was added Zn(OTf)$_2$ (73.6 mg, 0.201 mmol), MeCN (0.21 mL, 4.03 mmol), dioxane (0.32 mL) and NH$_2$NH$_2$ (0.63 mL., 20.1 mmol). The vessel was sealed and allowed to stir at 60° C. for hours after which it was allowed to cool and the septum removed. To the reaction mixture was added NaNO$_2$ (556.1 mg, 8.06 mmol) in 10 mL of water followed by 1 M HCl until the pH=3. The aqueous phase was extracted three times with methylene chloride (100 mL). The combined organic extracts were dried with MgSO$_4$ and concentrated using a rotary evaporator. The crude mixture was filtered through 10 g of silica (methylene chloride:methanol, 100:0.5, 100 mL) and concentrated using a rotary evaporator. This mixture was then dissolved in 8 mL of methylene chloride and TFA (1 mL) was added and the reaction was allowed to stir at room temperature for 30 minutes, after which it was concentrated under a stream of nitrogen. The crude mixture was purified using flash column chromatography (methylene chloride:methanol, 10:0.1) to give HELIOS 370Me (77.4 mg, 0.20 mmol, 50.6%) as a red solid.

$^1$H NMR (400 MHz, (CD$_3$)$_2$SO) δ 8.50 (d, J=7.60 Hz, 1H), 8.40 (s, 1H), 7.76 (t, J=7.6 Hz, 1H), 7.64 (d, J=8.0 Hz, 1H), 7.55 (m, 1H), 3.01 (s, 3H), 2.26 (s, 3H); $^{13}$C NMR (100 MHz, (CD$_3$)$_2$SO) δ 167.2, 163.1, 158.9, 148.6 (dd, J=233.0, 5.3 Hz), 148.3 (t, J=2.6 Hz), 139.1 (dd, J=233.1, 9.3 Hz), 138.5 (dd, J=7.5, 2.0 Hz), 137.4 (m), 135.5, 134.2, 131.9, 129.4, 129.1, 126.9, 123.6, 111.3 (d, J=9.3 Hz), 107.0 (dd, J=19.0, 2.7 Hz), 20.8, 16.7. ESIMS [M–H]$^-$ calcd for C$_{19}$H$_{11}$F$_2$N$_4$O$_3$ 381.08. found 381.06.

To nitrile 10c (144.0 mg, 0.40 mmol) in a microwave reaction tube under a stream of argon was added Zn(OTf)$_2$ (73.6 mg, 0.201 mmol), formamidine acetate (419.6 mg mL, 4.03 mmol), DMF (0.32 mL) and NH$_2$NH$_2$ (0.63 mL, 20.1 mmol). The vessel was sealed and allowed to stir at 60° C. for 15 hours after which it was allowed to cool and the septum removed. To the reaction mixture was added NaNO$_2$ (556.1 mg, 8.06 mmol) in 10 mL of water followed by 1 M HCl until the pH=3. The aqueous phase was extracted three times with methylene chloride (100 mL). The combined organic extracts were dried with MgSO$_4$ and concentrated using a rotary evaporator. The crude mixture was filtered through 10 g of silica (methylene chloride:methanol, 100: 0.5, 100 mL) and concentrated using a rotary evaporator. This mixture was then dissolved in 8 mL of methylene chloride and TFA (1 mL) was added and the reaction was allowed to stir at room temperature for 30 minutes, after which it was concentrated under a stream of nitrogen. The crude mixture was purified using flash column chromatography (methylene chloride:methanol, 10:0.1) to give HELIOS 370H (26.9 mg, 0.073 mmol, 18.3%) as a red solid.

$^1$H NMR (400 MHz, (CD$_3$)$_2$SO) δ 10.61 (s, 1H), 8.53 (d, J=8.0 Hz, 1H), 8.44 (s, 1H), 7.78 (t, J=7.6 Hz, 1H), 7.67 (d, J=7.6 Hz, 1H), 7.60 (d, J=11.6 Hz, 1H), 2.27 (s, 3H); $^{13}$C NMR (100 MHz, (CD$_3$)$_2$SO) δ 165.3, 158.9, 158.2, 148.5 (dd, J=232.0, 5.1 Hz), 148.5 (t, J=2.4 Hz), 139.1 (dd, J=235.6, 7.2 Hz), 138.5 (dd, J=9.4), 137.4 (m), 135.5, 134.6, 131.9, 129.5 (2C), 127.3, 123.6, 111.3 (d, J=8.9 Hz), 107.0 (dd, J=21.8, 2.8 Hz), 16.7. ESIMS [M–H]$^-$ calcd for C$_{18}$H$_9$F$_2$N$_4$O$_3$ 367.06. found 366.96.

Example 24—Preparation of HELIOS 370H

Example 25—Preparation of TCOc

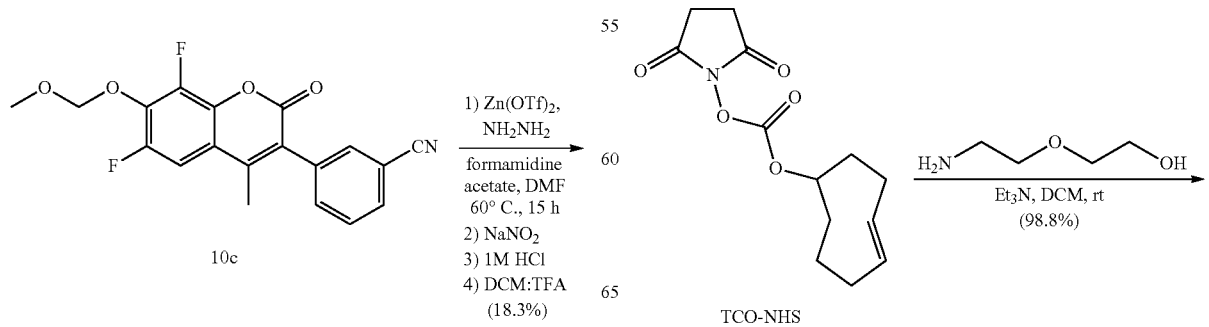

TCO-NHS

-continued

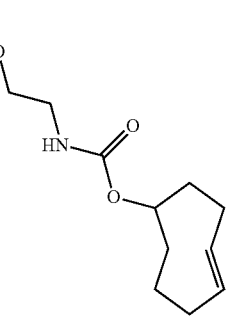

TCOc

To TCO-NHS (45.4 mg, 0.17 mmol) dissolved in 2 mL of methylene chloride was added triethylamine (0.05 mL, 0.35 mmol), and 2-(2-Aminoethoxy)ethanol (0.07 mL, 0.71 mmol). The mixture was allowed to stir at room temperature for thirty minutes after which it was concentrated under a stream of nitrogen. The crude mixture was purified using flash column chromatography (hexanes:ethyl acetate gradient, 1:1 to 100% ethyl acetate) to give TCOc (43.3 mg, 0.073 mmol, 98.8%) as a clear oil.

$^1$H NMR (400 MHz, CDCl$_3$) δ 5.50 (m, 2H), 5.03 (m, 1H), 4.31 (dd, J=9.6, 6.0 Hz, 1H), 3.71 (m, 2H), 3.53 (m, 4H), 3.33 (m, 2H), 2.31 (m, 4H), 2.01-1.85 (m, 4H), 1.77-166 (m, 2H), 1.55-1.51 (m, 1H); $^{13}$C NMR (100 MHz, CDCl$_3$) δ 156.6, 135.1, 133.2, 80.9, 72.4, 70.4, 61.9, 41.3, 40.9, 38.8, 34.5, 32.7, 31.1. ESIMS [M+H]$^+$ calcd for C$_{13}$H$_{24}$NO$_4$ 258.17. found 258.37.

Example 26—Preparation of Phalloidin-TCO

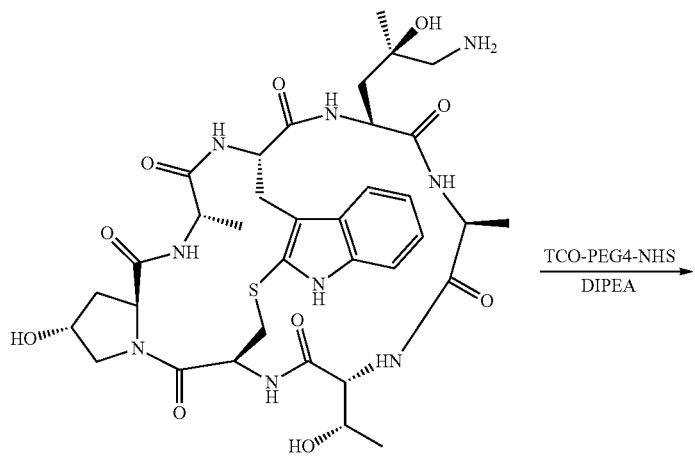

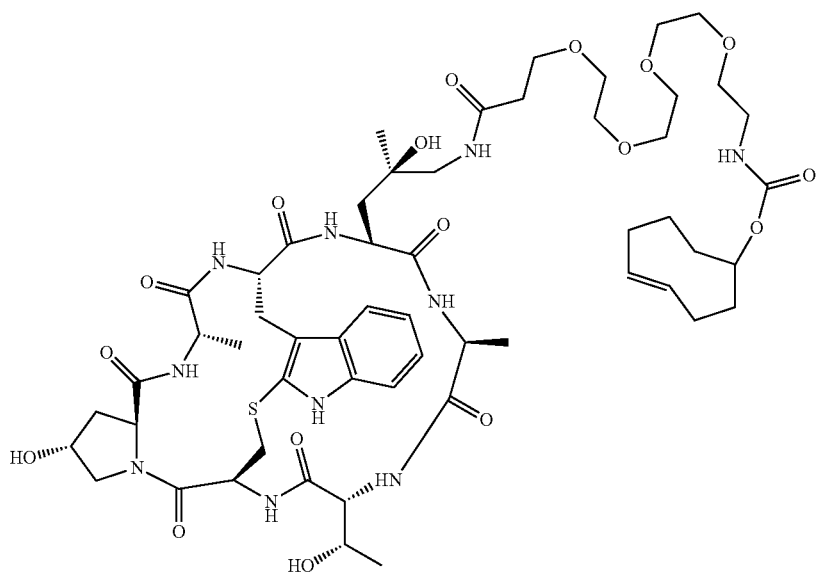

To a 10 mM solution of TCO-PEG4-NHS (70 µL, 0.7 µmoles, Click Chemistry Tools, Scottsdale, Ariz.) in DMF in a microvial was added amino-phalloidin (60 µg, 0.07 µmoles, American Peptide Company, Sunnyvale, Calif.) and diisopropylethylamine (DIPEA, 0.2 µL, 1.1 µmole). After 30 minutes at room temperature with occasional vortex agitation, the reaction mixture was purified by reverse phase chromatography on a Waters Xterra C18, 2.5 µm, 10 mm×50 mm, column (water:acetonitrile, both with 0.1% formic acid; gradient elution from 5% to 75% acetonitrile) to give phalloidin TCO (58 µg, 0.05 µmoles, 70%). The amounts of aminophalloidin and phalloidin-TCO product were determined spectrophotometrically, based on the known extinction coefficient of phalloidin at 291 nm (13,500). Reverse phase LCMS characterization of the purified material: ESI-MS [M+H]$^+$ calculated for $C_{55}H_{82}N_{10}O_{17}S$ 1187.56. found 1187.43.

Example 27—Preparation of Marina Blue-Tz

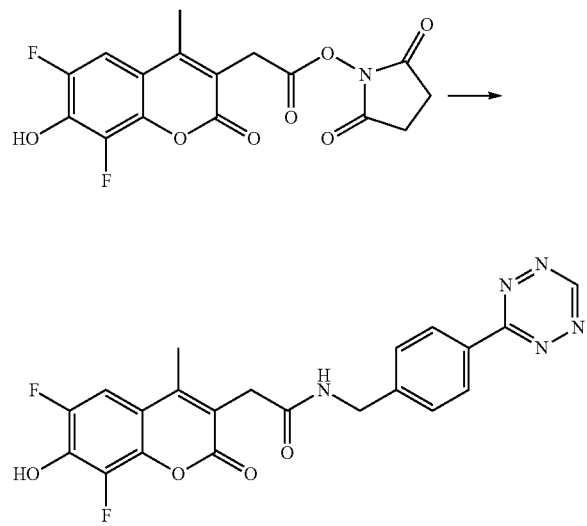

To a solution of Marina Blue—succcinimidyl ester (LifeTechnologies, M10165, Grand Island, N.Y.) at 10 mM in DMF (50 µL, 0.5 µmoles) was added 1 uL of diisopropylethylamine, followed by a small aliquot of dry benzylaminotetrazine-HCl (MW 223.06). After 30 minutes at room temperature with occasional vortex agitation, the reaction mixture was purified by reverse phase chromatography on a Waters Xterra C18, 2.5 µm, 10 mm×50 mm, column (water:acetonitrile, both with 0.1% formic acid; gradient elution from 5% to 75% acetonitrile) to give Marina Blue-Tz (yield not determined). Reverse phase LCMS characterization of the purified material: ESI-MS [M−H]$^-$ calculated for $C_{21}H_{15}F_2N_5O_4$ 438.11. found 438.01.

Example 28—Fluorogenic Characterization of HELIOS Probes

As described above, the fluorescence purity of all HELIOS compounds was verified by LCMS prior to quantitative activation experiments, for which a fresh aliquot of the fluorophore collected from the analytical HPLC elution was used. Exceptionally pure material is required to obtain the peak measured turn-on ratios, as the presence of trace bright contaminants limits the maximum observable ratio.

Stock solutions of the freshly-purified tetrazine dyes were prepared in MeCN and stored in the dark at 4° C. during experiments. For fluorescence measurements, the probes diluted into 2 mL or 3 mL of phosphate buffered saline (PBS), pH 7.4 (Corning, cellgro) in a standard 10 mm quartz cuvette. Working at peak excitation and emission wavelengths for each probe, data were collected as a continuous time series to enable accurate measurement of the baseline intensity values and optimize signal to noise. Fluorescence experiments were conducted at a range of dye concentrations spanning 100 nM-750 nM, with 500 nM being a typical working concentration. The time to peak turn on ratio (but not the final magnitude) is a function of the added TCOc (see Example 25) concentration; for the time courses presented herein, 10 µM TCOc was used. Measurements of solvent and pre-activation emission intensity for baseline values were collected serially over at least 30 seconds, prior to addition of TCOc to initiate the fluorogenic reaction. After addition of TCOc (typically a 20-fold excess, as above), the fluorescence emission intensity was monitored until a plateau was reached. Activation ratios were calculated from the peak emission intensity of the dihydropyridazine product and the corresponding baseline intensity over background. Data were normalized to set the initial background fluorescence of the HELIOS probe to one unit over background, as plotted in FIG. 9 in the main text.

Quantum yield determinations: quinine sulfate dihydrate (Fluorescence Reference Standard grade, AnaSpec, Inc) in 0.5 M $H_2SO_4$ was used as a reference, with an excitation wavelength of 370 nm; a value of 0.546 was used for the reference quantum yield (Eaton, D. F., *Pure and Applied Chemistry*, 1988 60(7), 1107-1114). Calculations were made according to the methods described by Crosby and Demas (*Chemical Reviews*, 1971, 75(8), 991-1024).

Figure 9:
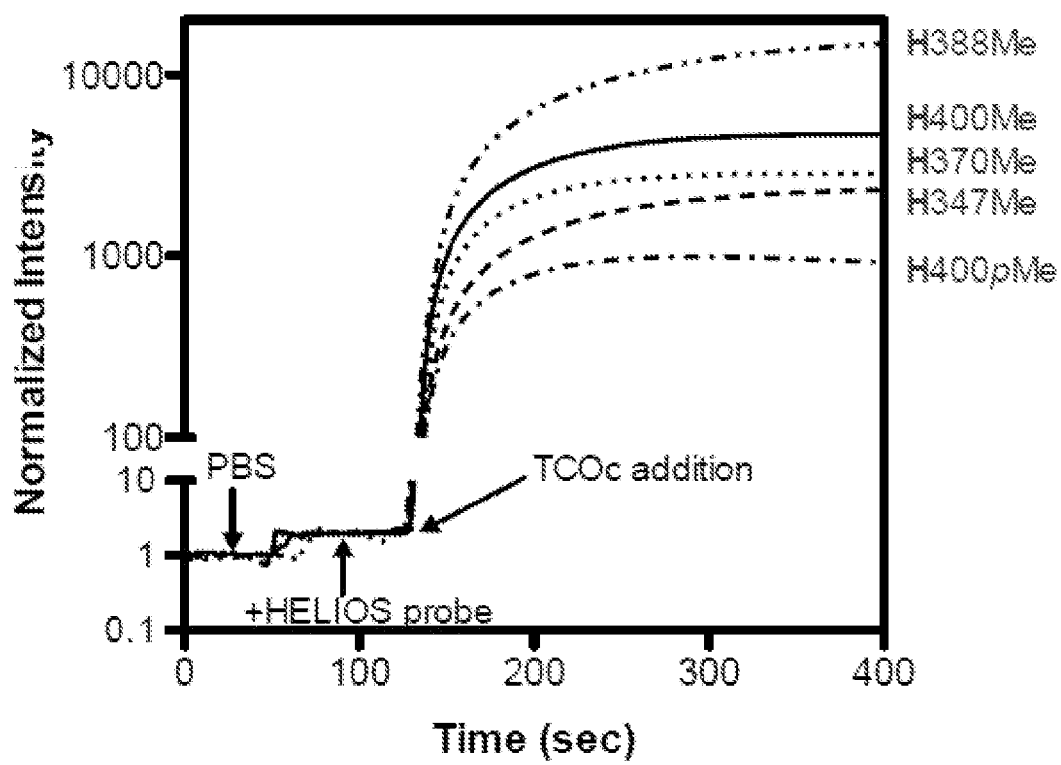
FIG. 9 shows the fluorogenic activation of HELIOS probes upon reaction with TCOc (H=HELIOS).

HELIOS 400Me and HELIOS 400pMe were both soluble in phosphate buffered saline (PBS) at micromolar concentrations and negligibly fluorescent in their native state. After rigorous purification to remove trace fluorescent impurities, the fluorogenic properties of these new coumarin-Tz conjugates was evaluated on reaction with TCOc, a novel trans-cyclooctene derivative (TCOc) that incorporates a carbamate-linked PEG$_2$ side chain for improved water solubility. Addition of TCOc to HELIOS 400Me in PBS yielded a 4,000-fold peak turn-on ratio (FIG. 9). Reaction of HELIOS 400pMe with TCOc yielded a turn on ratio of 1,000-fold, four-fold lower than its meta-linked counterpart. Mechanistically, the observation of 1000-fold turn-on in a perpendicular-dipole configuration argues against FRET playing a significant role in the energy transfer mechanism. As shown below, HELIOS 388Me in PBS yielded a remarkable 11,000-fold turn-on upon reaction with TCOc, the highest turn-on ratio reported to date. When ligated to TCOc in PBS, HELIOS 347Me and HELIOS 370Me displayed 2,500-fold and 2,900-fold turn-on ratios, respectively, in spite of minimal spectral overlap with the tetrazine absorption band at 520 nm. By comparison, FRET-based coumarin-tetrazine interactions are dramatically less efficient: a flexibly linked analogue of HELIOS 370H displayed only a 60-fold turn-on (Marina Blue-Tz), corroborating the dipole-orientation analysis described previously. All four HELIOS probes exhibit very good postclick quantum yields in PBS, in agreement with structurally similar coumarins (Table 2).

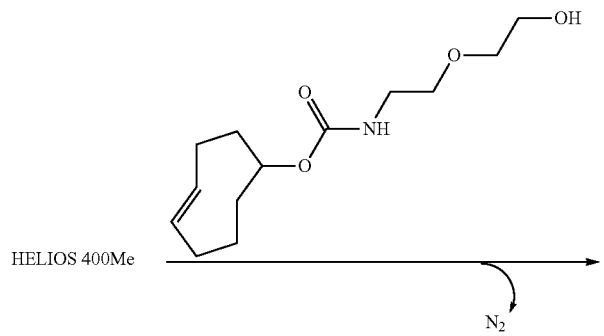
HELIOS 400Me ⟶ (−N₂)
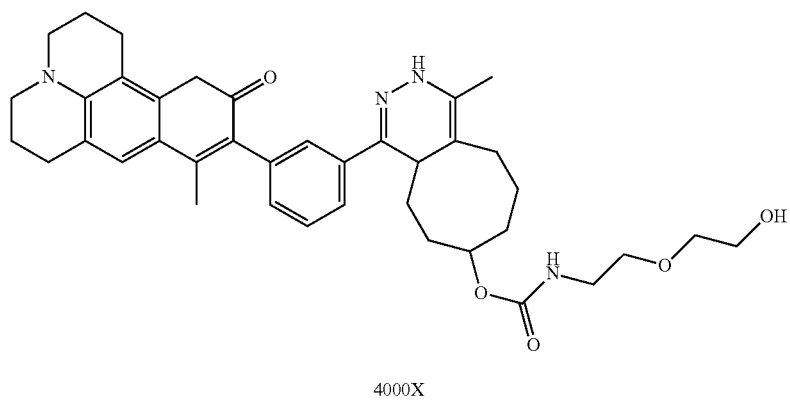
4000X
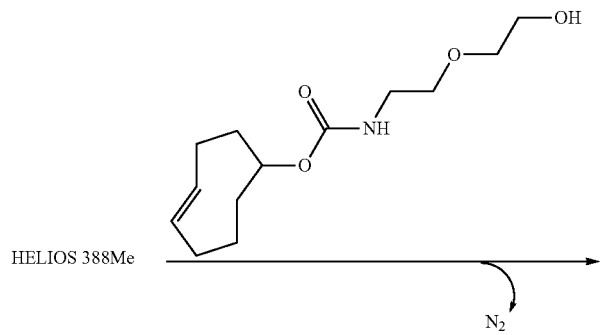
HELIOS 388Me ⟶ (−N₂)
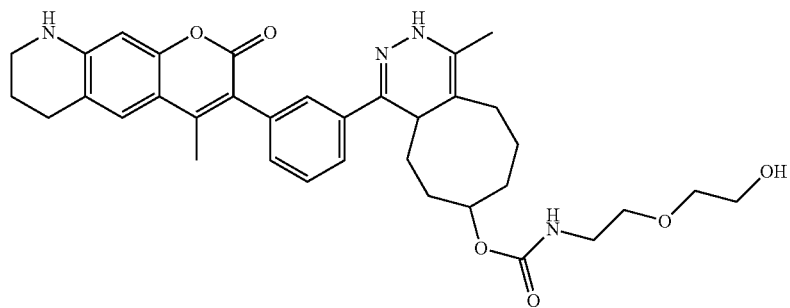
11000X

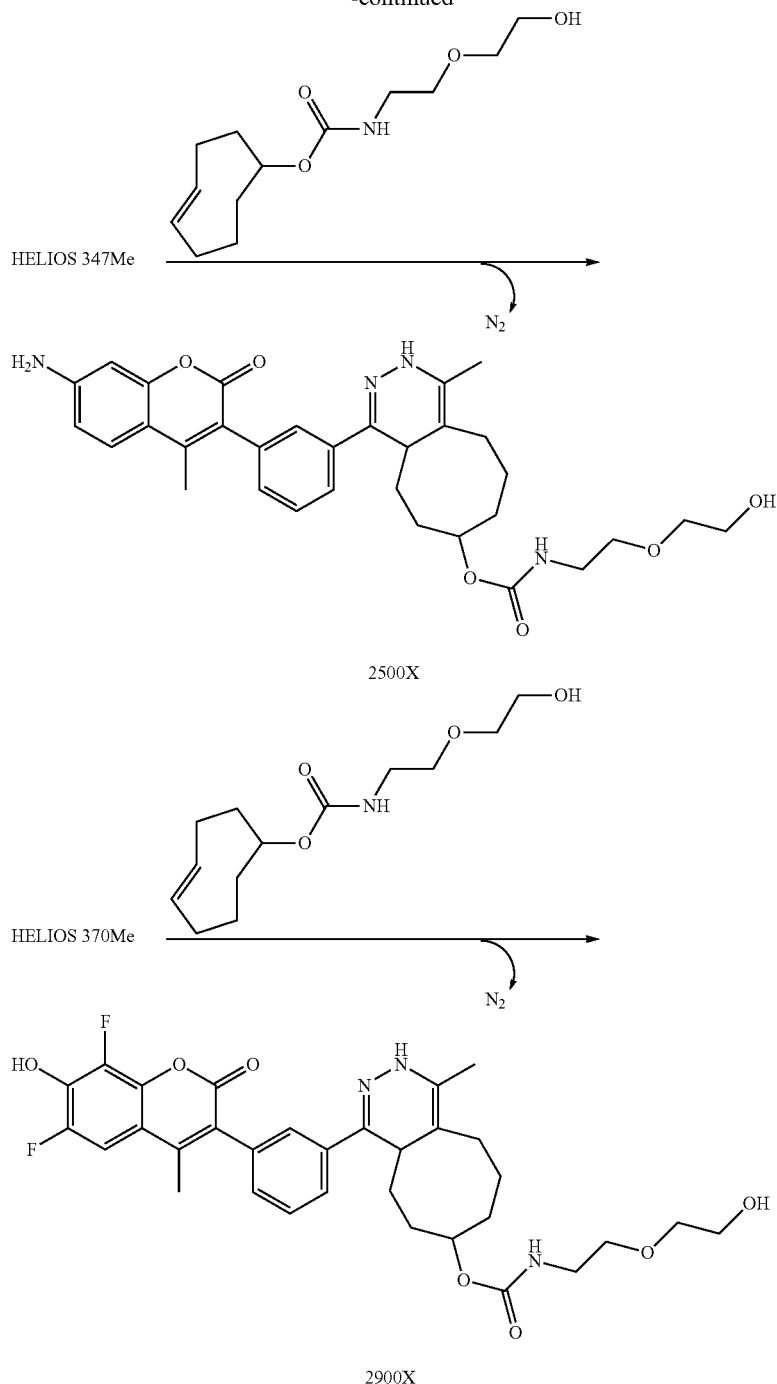

TABLE 2

| Probe | Peak Ex/Em Wavelengths | ε[a] | Φ w/TCOc[b] | Fluorescence Enhancement[c] |
| --- | --- | --- | --- | --- |
| HELIOS 400 | 400/502 | 16,000 | 0.41 | 4,000-fold |
| HELIOS 388 | 388/482 | 20,000 | 0.38 | 11,000-fold |
| HELIOS 370 | 370/463 | 19,000 | 0.49 | 2,900-fold |
| HELIOS 347 | 347/455 | 18,500 | 0.29 | 2,500-fold |
| Marina Blue-Tz | 362/459 | ND | ND | 60-fold |

[a] At peak excitation wavelength in PBS, pH 7.4.
[b] Quantum yield for the dihydropyridazine product after complete reaction of the indicated compound with TCOc in PBS at pH 7.4; quinine sulfate in $H_2SO_4$ (0.5M., Φ = 0.546) was used as the standard.
[c] Fluorogenic turn-on ratio of the Me-tetrazines upon reaction with TCOc.

Example 29—Solvent Polarity Effects

Figure 10:
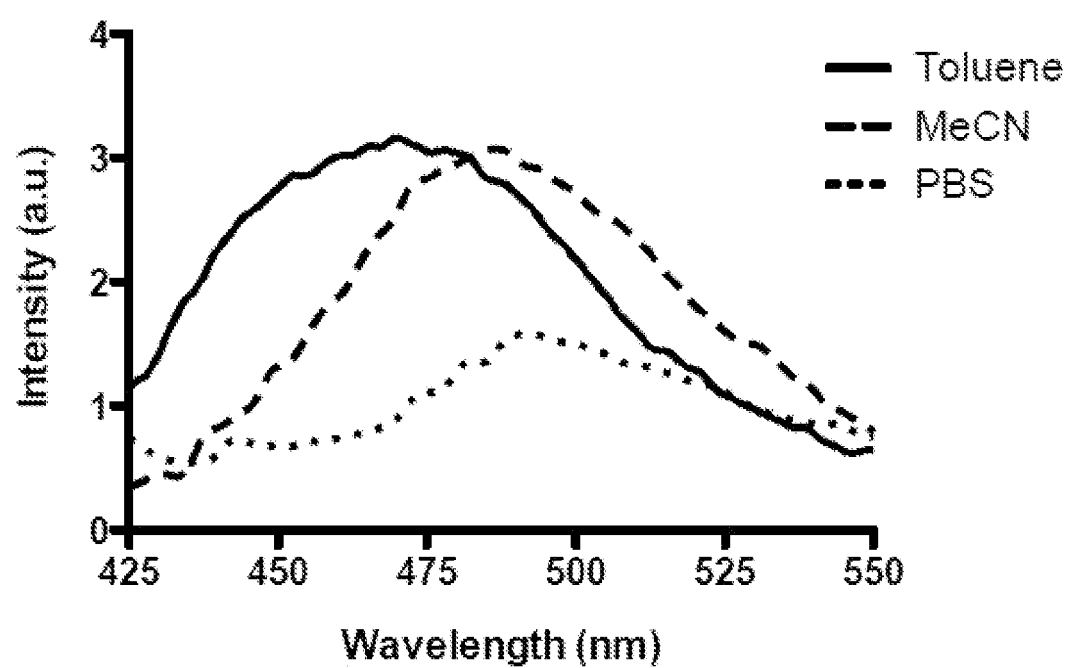
FIG. 10 shows the fluorescence emission spectra of HELIOS 400Me in PBS (pH 7.4), acetonitrile (dielectric constant 37.5), and toluene (dielectric constant 2.4).

Fluorescence emission spectra of HELIOS 400Me in PBS (pH 7.4), acetonitrile (dielectric constant 37.5), and toluene (dielectric constant 2.4) was measured (see FIG. 10). Emission spectra are the mean of 2 or 3 scans and the dashed lines represent +/−SEM. Instrument settings were adjusted to optimize sensitivity given the minimal fluorescence of the native HELIOS probe, and samples were prepared by matched dilution of a concentrated stock solution of HELIOS 400Me into the respective solvents. Redox-based quenching, such as through photoinduced electron transfer (PET) from the excited coumarin to the relatively electron-poor tetrazine ring, was judged unlikely to contribute significantly, because the fluorescence emission intensity was largely independent of solvent polarity, with less than a twofold change between PBS and the organic solvents, and no intensity difference between toluene ($\varepsilon$=2.4) and acetonitrile ($\varepsilon$=37.5). PET is characteristically enhanced by the relative stabilization of charge separated states in polar solvents [E. E. Neuteboom, S. C. J. Meskers, E. H. A. Beckers, S. Chopin, R. A. J. Janssen, *J. Phys. Chem. A* 2006, 110, 12363].

Example 30—In Vitro Imaging

General Methods

Microscope: Multichannel images were collected on an Olympus Fluoview FV1000 confocal laser microscope. Coumarin probes were excited with a 405 nm laser, with alternate excitation sources used as relevant for reference channels, paired with appropriate emission filter sets.

Cell culture: A-431 cells (ATCC CRL-1555) and COS-1 cells (ATCC CRL-1650) were cultivated in Dulbecco's Modified Eagle's Medium (DMEM), supplemented with 10% fetal bovine serum and grown in standard culture conditions in 10 cm dishes. OVCA-429 cells were cultivated in RPMI-1640 supplemented with 10% fetal bovine serum under standard culture conditions. For imaging experiments cells were plated on Millicell EZ slides (EMD Millipore, Inc, Billerica, Mass.).

Antibody reagents: Monoclonal antibody-TCO conjugates were prepared by incubation of commercially available monoclonal antibodies TCO-PEG4-NHS (Click Chemistry Tools, Scottsdale, Ariz.). Anti EGFR (Cetuximab, Imclone). Anti cytochrome c oxidase (COXIV, Cell signaling Technology, #4844, Danvers, Mass.).

An aliquot of antibody in the manufacturer-supplied storage solution was buffer exchanged into PBS with 10 mM sodium bicarbonate, pH 8.0, on a 40K ZebaSpin desalting column (0.5 mL, Thermo Fisher Scientific, Rockford, Ill.). To this solution was added 20 equivalents of TCO-PEG4-NHS; the mixture was allowed to react at 25° C. for 30 minutes, with continuous shaking. The reaction mix was loaded onto a 40K ZebaSpin column to remove organic solvent and small molecule fractions; this eluate was loaded onto a second 40K ZebaSpin column to ensure comprehensive removal of any excess TCO.

EGFR Imaging: Fixed A431 cells were prepared by treatment with 4% paraformaldehyde solution (10 min, room temperature), followed by 3 washes with PBS. Fixed cells were stored at 4° C. until the time of imaging, when they were incubated for 20 minutes with 20 µg/mL cetuximab-TCO, then rinsed three times with PBS.

For optimal image quality, HELIOS 370H probe must be purified on the day of imaging by reversed phase HPLC-MS. The concentration of stock solutions in PBS were calculated by absorbance spectrometry, based on the measured extinction coefficient of 19000 $M^{-1}$ $cm^{-1}$. Prior to imaging, the purified stock solutions were subjected to turn-on testing, verifying a fluorogenic turn-on ratio of >1000-fold for HELIOS 370H. For imaging experiments, the acetonitrile stocks were diluted into PBS to yield a 100 nM solution. Image acquisition: Immediately prior to imaging, buffer was replaced with a 100 nM solution of HELIOS 370H probe in PBS. Specific staining was evident within 10 seconds and reached maximum signal/background intensity over a time course of 3-5 minutes.

Mitochondria Imaging: At ~70% confluence, OVCA-429 cells were incubated with 3% v/v of CellLight Fluorescent mitochondria-targeted red fluorescent protein BacMam reagent, reconstituted according to the manufacturer's guidelines (C10601, Invitrogen, Carsbad, Calif.), in complete medium for 24 h. Following incubation, cells were washed in PBS and incubated in growth media a further 24 hrs before fixation.

The cells were fixed with 4% paraformaldehyde and permeabilized with 0.5% Triton-X-100 in PBS. Cells were incubated with anti-COX IV-TCO (10 g/mL) for 40 minutes, then washed twice with PBS prior to imaging. HELIOS 388H was freshly purified as described above and added to cells at 100 nM concentration. Mitochondrial labeling was evident within 2 minutes and stable target to background ratios were observed on serial images collected up to an hour from dye addition.

Actin Cytoskeleton Imaging: carried out per procedures developed by Mitchison and coworkers (e.g. Cramer, L., and Mitchison, T. J., *J Cell Biol.* 1993 August; 122(4):833-43, http://mitchison.med.harvard.edu/protocols.html). In brief, phalloidin-TCO was dissolved in methanol to prepare a stock solution at 250-1000 µg/mL (stored at −80° C.); this stock was diluted into the labeling buffer to give a final staining solution at 1 µg/mL. Labeling buffer: 10 mM Tris buffered saline, pH 7.4 (TBS), with 0.1% triton X-100 and 2% bovine serum albumin.

COS-1 cells were grown in standard culture conditions as described above and then fixed and permeabilized per the procedures of Mitchison and coworkers (vide supra). In brief, cells were fixed in 4% formaldehyde in cytoskeleton buffer for 20 minutes, and then permeabilized with 0.1% Triton-X-100 in TBS. Cytoskeleton buffer: 10 mM MES, pH6.1, 138 mM KCl, 3 mM MgCl, 2 mM EGTA, 0.32M sucrose. Nuclear staining was performed by incubating the fixed and permeabilized cells with DRAQ5 (Biostatus, DR50050) diluted to a final concentration of 1 M for 3-5 minutes at room temperature. After 20-40 minutes incubation with phalloidin-TCO (1 µg/mL), cells were washed once with PBS and then imaged after addition of 100 nM HELIOS 388H or HELIOS 370H.

Results

Figure 11:
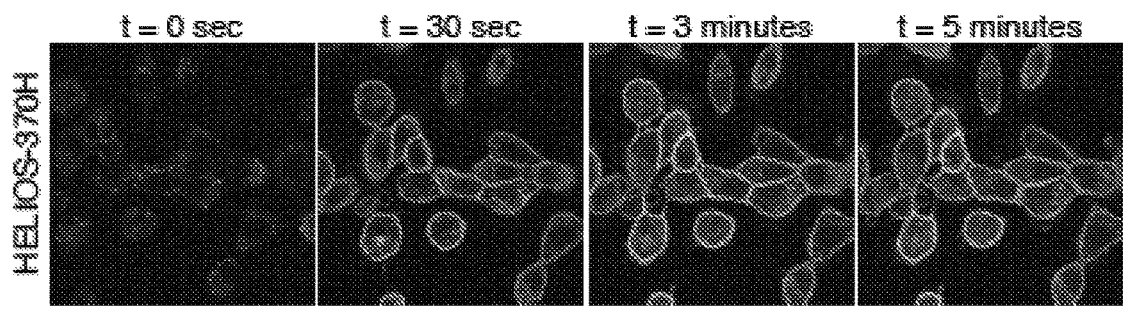
FIG. 11A shows no wash fluorogenic imaging of EGFR expression on A431 cells using HELIOS 370H. Bright, membrane specific staining is visible within seconds, peaks within 3 minutes and is stable thereafter.
FIG. 11B shows cells imaged with HELIOS 370H (left) and control cells (right) exhibiting autofluorescence at baseline, prior to addition of dye.
Figure 11:
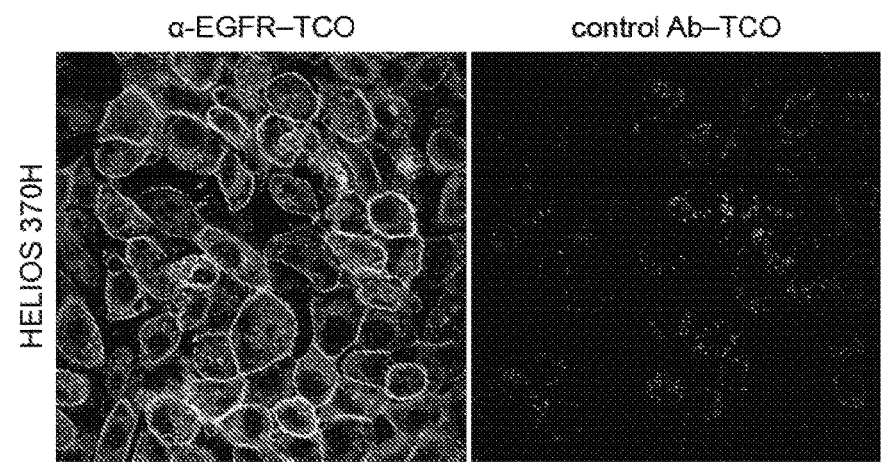

HELIOS 370H was used as a model to determine the applicability of the HELIOS probes as a native bioorthogonal fluorogenic imaging agent. This model system was used to assess HELIOS probe kinetics in the extracellular context: imaging of the epidermal growth factor receptor (EGFR) on the surface of cancer cells. EGFR overexpression plays a critical role in the most common molecularly-defined subtype of lung cancer, where it is a key treatment target, and drives proliferation in other epithelial malignancies, including colon cancer and pancreatic cancer. As noted above, A431 cells were incubated with a TCO labeled anti-EGFR antibody (20 µg/mL, Cetuximab, ImClone) for 20 minutes and then washed briefly with PBS. Addition of 100 nM HELIOS 370H in PBS revealed bright, membrane specific staining coinciding with the known distribution of the receptor (FIG. 11A). Images were generated within seconds of dye addition and exhibited no nonspecific binding even after extended incubation, nor any membrane staining in the presence of a control antibody-TCO conjugate (FIG. 11B).

Figure 12:
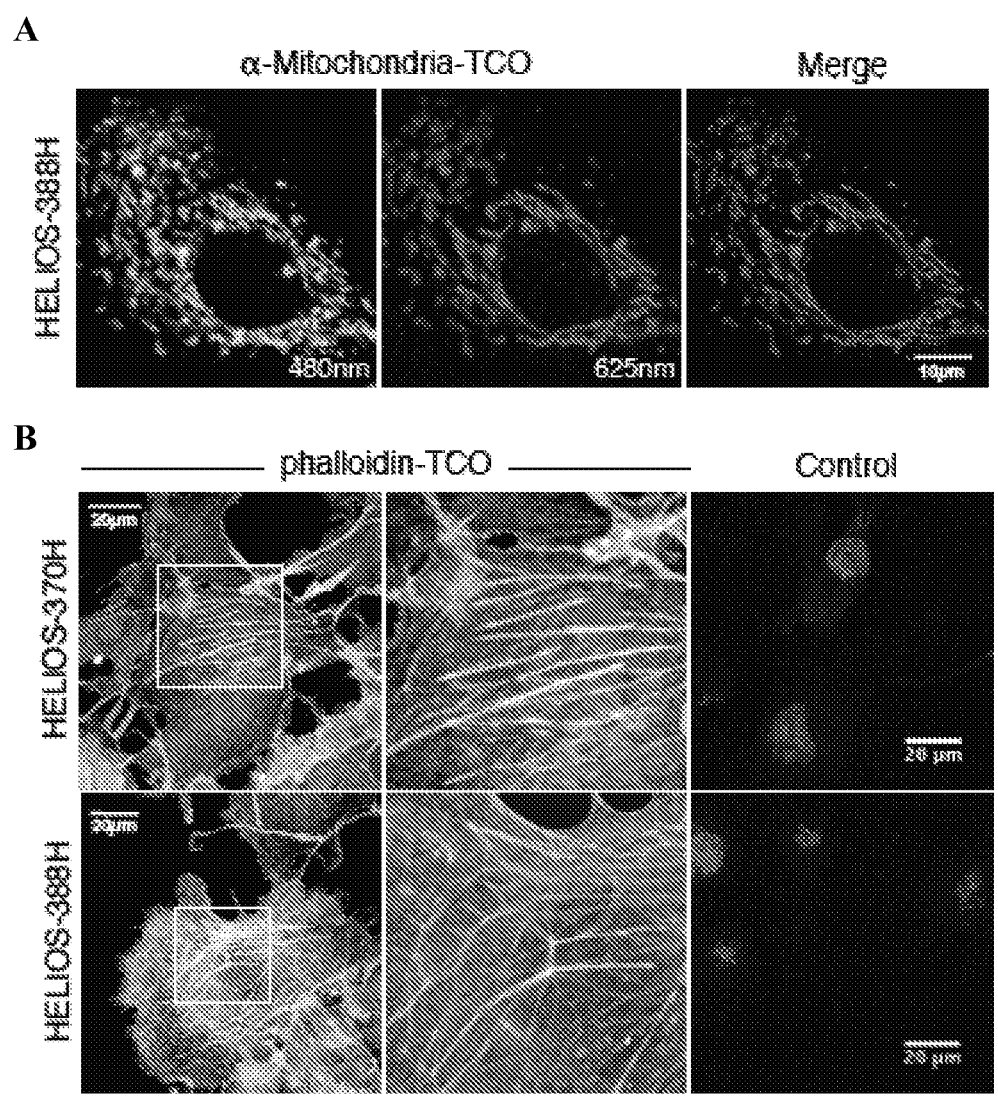
FIG. 12 illustrates no-wash fluorogenic imaging of intracellular targets.

To further explore the imaging potential of HELIOS probes, mitochondria were selected as a target; their structures have features at the diffraction limit of conventional light microscopy. OVCA-429 cells expressing mitochondria-specific red fluorescent protein (RFP) were incubated with an anti-mitochondria antibody-TCO conjugate and visualized with HELIOS 388H, yielding high spatial resolution images with good colocalization (FIG. 12A). Intracellular imaging of small molecule targets is another area of intense interest, given the potential applications in drug development, chemical biology, and optical pharmacology. To demonstrate the utility of HELIOS probes in this context with a structurally validated model system, the ability of the probes to image the actin cytoskeleton was tested with a phalloidin-TCO conjugate (Example 26). Sequential addition of phalloidin-TCO and several HELIOS probes produced vivid fluorogenic images of the cytoskeleton; control experiments revealed negligible background (FIG. 12B).

Example 31—In Vivo Imaging with HELIOS Probes

Nude mice (Cox7, Massachusetts General Hospital) were surgically implanted with a dorsal skin window chamber. A-431 cells (ATCC CRL-1555, Manassas, Va.), a human epidermoid carcinoma cell line with overexpression of the epidermal growth factor receptor (EGFR), were then implanted into the window chamber as a suspension of 2-3 million cells in a 1:1 mixture of phosphate buffered saline (PBS) and matrigel. Tumors were allowed to develop for ~2 weeks, by which time they had become vascularized and attained a diameter of 2-3 mm.

In parallel, a TCO conjugated anti-EGFR antibody was prepared as previously reported (Haun et al., *Nat. Nanotech.*, 2010, 5, 660-665). 24 hours prior to imaging mice were injected via tail vein IV catheter with 100 μL of a 1 mg/mL solution of the antibody in PBS. On the day of imaging, a derivative of compound 2a:

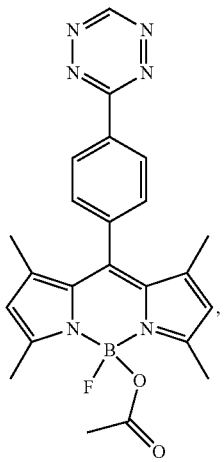

was purified by HPLC. The pure dye was dried by evaporation and formulated by dissolving the dry powder in 20 μL of a 1:1 mixture of dimethylacetamide:solutol HS-15, followed by slow dilution in PBS to a final volume of 300 μL. The concentration of the clear orange solution was determined spectrophotometrically (between 100-200 μM) and stored at 4° C. until imaging.

Figure 13:
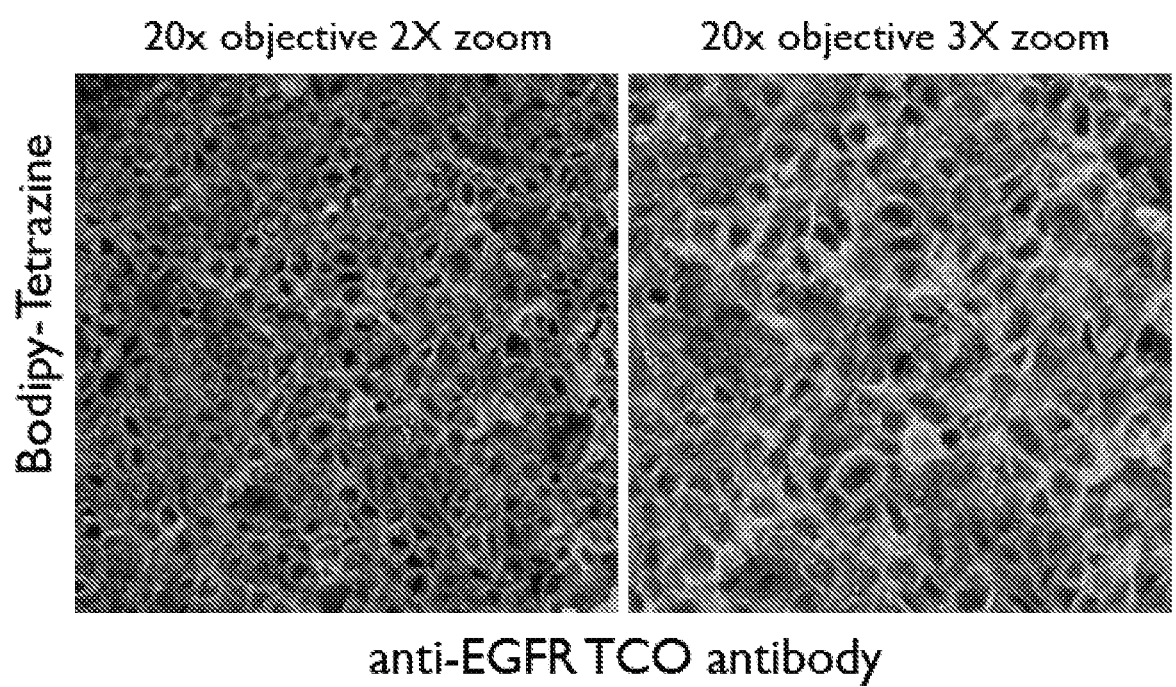
FIG. 13 illustrates in vivo imaging of a HELIOS probe as described herein.

Mice were anesthetized with 2% isoflurane in 2 L/min oxygen on a heated microscope stage and a tail vein catheter was placed. In some instances, Angiosense-680 (Perkin Elmer, Waltham, Mass., USA) was injected to delineate the vasculature. Static and time series images were collected using a customized Olympus FV1000 confocal microscope (Olympus America). A XLUMPLFLN 20× water immersion objective (NA 1.0) water immersion objective was used for data collection (Olympus America). Pre-treatment images of the tumor cells were collected, and then time-lapse imaging was initiated synchronously with injection of 150 μL of the fluorogenic BODIPY-tetrazine dye by tail vein IV, followed by a second 150 μL injection of dye ten minutes later. Images in FIG. 13 illustrate bright membrane-specific staining of tumor cells within the window chamber, consistent with the known distribution of EGFR, as well as punctate foci within the cells at site of endocytic receptor internalization, all with excellent target to background ratios.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound, which is:

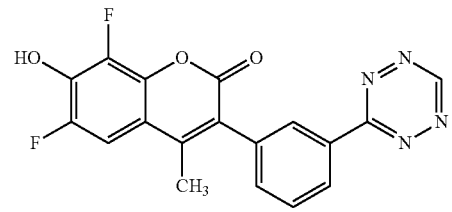 [SMILES: Cc1c(-c2cccc(-c3nncnn3)c2)c(=O)oc2c(F)c(O)c(F)cc12]

or a salt thereof.

2. A method for imaging a subject, the method comprising:
a) administering to the subject an effective amount of a dieneophile conjugated to one or more of a small molecule therapeutic agent, antibody, nanoparticle, polymer, and mixtures thereof;
b) administering to the subject an effective amount of a compound which is:

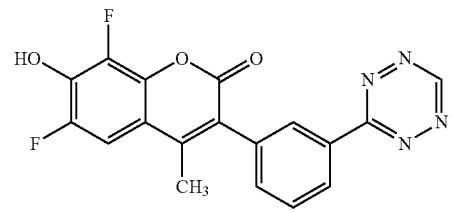 [SMILES: Cc1c(-c2cccc(-c3nncnn3)c2)c(=O)oc2c(F)c(O)c(F)cc12]

or a salt thereof;
and
c) imaging the subject.

3. A pharmaceutical composition, comprising the compound which is:
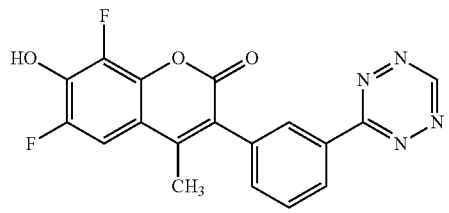 [SMILES: Cc1c(-c2cccc(-c3nncnn3)c2)c(=O)oc2c(F)c(O)c(F)cc12]
or a salt thereof, and a pharmaceutically acceptable excipient.
* * * * *

UNITED STATES PATENT AND TRADEMARK OFFICE
CERTIFICATE OF CORRECTION

PATENT NO. : 10,517,965 B2
APPLICATION NO. : 14/889647
DATED : December 31, 2019
INVENTOR(S) : Labros Meimetis, Jonathan Carlson and Ralph Weissleder Page 1 of 1

It is certified that error appears in the above-identified patent and that said Letters Patent is hereby corrected as shown below:

In Column 88, Line 49, Claim 2, delete "dieneophile" and insert -- dienophile --

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*